(12) United States Patent
Goix et al.

(10) Patent No.: US 8,685,711 B2
(45) Date of Patent: *Apr. 1, 2014

(54) METHODS AND COMPOSITIONS FOR HIGHLY SENSITIVE DETECTION OF MOLECULES

(75) Inventors: Philippe J. Goix, Oakland, CA (US); Robert Puskas, Manchester, MO (US); John Todd, Lafatette, CA (US); Richard A. Livingston, Webster Groves, MO (US); Douglas Held, Ballwin, MO (US)

(73) Assignee: Singulex, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/731,500

(22) Filed: Mar. 25, 2010

(65) Prior Publication Data

US 2010/0329929 A1  Dec. 30, 2010

Related U.S. Application Data

(60) Continuation of application No. 11/830,762, filed on Jul. 30, 2007, now abandoned, which is a division of application No. 11/784,211, filed on Apr. 4, 2007, now Pat. No. 7,572,640, which is a continuation-in-part of application No. 11/048,660, filed on Jan. 28, 2005, now abandoned, said application No. 11/830,762 is a division of application No. 11/784,211, filed on Apr. 4, 2007, now Pat. No. 7,572,640.

(60) Provisional application No. 60/613,881, filed on Sep. 28, 2004, provisional application No. 60/624,785, filed on Oct. 29, 2004, provisional application No. 60/636,158, filed on Dec. 16, 2004, provisional application No. 60/789,304, filed on Apr. 4, 2006, provisional application No. 60/872,986, filed on Dec. 4, 2006, provisional application No. 60/861,498, filed on Nov. 28, 2006, provisional application No. 60/808,662, filed on May 26, 2006, provisional application No. 60/793,664, filed on Apr. 19, 2006.

(51) Int. Cl.
*C12M 1/34* (2006.01)

(52) U.S. Cl.
USPC .................................. 435/287.1; 435/288.7

(58) Field of Classification Search
USPC ........................................... 435/287.1, 288.7
See application file for complete search history.

(56) References Cited

U.S. PATENT DOCUMENTS

| | | | |
|---|---|---|---|
| 4,071,298 A | 1/1978 | Falconer | |
| 4,172,227 A | 10/1979 | Tyrer et al. | |
| 4,243,318 A | 1/1981 | Stohr | |
| 4,251,733 A | 2/1981 | Hirleman, Jr. | |
| 4,452,773 A | 6/1984 | Molday | |
| 4,768,879 A | 9/1988 | McLachlan et al. | |
| 4,770,183 A | 9/1988 | Groman et al. | |
| 4,793,705 A | 12/1988 | Shera | |
| 4,927,265 A | 5/1990 | Brownlee | |
| 4,979,824 A | 12/1990 | Mathies et al. | |
| 5,002,389 A | 3/1991 | Benser | |
| 5,041,733 A | 8/1991 | Noguchi et al. | |
| 5,094,594 A | 3/1992 | Brennan | |
| 5,108,179 A | 4/1992 | Myers | |
| 5,138,170 A | 8/1992 | Noguchi et al. | |
| 5,209,834 A | 5/1993 | Shera | |
| 5,230,997 A | 7/1993 | Frenkel | |
| 5,269,937 A | 12/1993 | Dollinger et al. | |
| 5,274,240 A | 12/1993 | Mathies et al. | |
| 5,385,707 A | 1/1995 | Miltenyi et al. | |
| 5,480,614 A | 1/1996 | Kamahori | |
| 5,540,494 A | 7/1996 | Purvis, Jr. et al. | |
| 5,543,838 A | 8/1996 | Hosier et al. | |
| 5,547,849 A | 8/1996 | Baer et al. | |
| 5,571,410 A | 11/1996 | Swedberg et al. | |
| 5,603,351 A | 2/1997 | Cherukuri et al. | |
| 5,605,662 A | 2/1997 | Heller et al. | |
| 5,633,503 A | 5/1997 | Kosaka | |
| 5,645,702 A | 7/1997 | Witt et al. | |
| 5,653,859 A | 8/1997 | Parton et al. | |
| 5,653,939 A | 8/1997 | Hollis et al. | |
| 5,658,413 A | 8/1997 | Kaltenbach et al. | |
| 5,681,751 A | 10/1997 | Begg et al. | |
| 5,682,038 A | 10/1997 | Hoffman | |
| 5,716,825 A | 2/1998 | Hancock et al. | |

(Continued)

FOREIGN PATENT DOCUMENTS

| | | |
|---|---|---|
| DE | 3720844 A1 | 1/1989 |
| JP | 2001-021565 | 1/2001 |

(Continued)

OTHER PUBLICATIONS

LeCaptain et al. "Characterization of DNA-protein complexes by capillary electrophoresis-single molecule fluorescence correlation spectroscopy", Analyst, 2001, 126:1279-1284.*
Wilson et al. "Validation of mitochondrial DNA sequencing for forensic casework analysis", Int J Legal Med., 1995, 108:68-74.*
Laser output data sheet: 4 pages, 2000.*
Ambrose, et al. Single molecule fluorescence spectroscopy at ambient temperature. Chemical Reviews. 1999; 99(10): 2929-56.
Anazawa, et al. Electrophoretic quantitation of nucleic acids without amplification by single molecule imaging. Anal. Chem. 2002; 74(19): 5033-38.

(Continued)

*Primary Examiner* — Bin Shen
(74) *Attorney, Agent, or Firm* — McDonnell Boehnen Hulbert & Berghoff LLP

(57) ABSTRACT

Disclosed are methods, kits, and compositions for the highly sensitive detection of molecules. The methods, kits, and compositions are useful in determining concentrations of molecules in samples to levels of 1 femtomolar, 1 attomolar, or lower. The methods, kits, and compositions also allow the determination of concentration over a wide range, e.g., 7-log range, without need for sample dilution.

23 Claims, 21 Drawing Sheets

(56) References Cited

U.S. PATENT DOCUMENTS

| | | | |
|---|---|---|---|
| 5,730,187 A | 3/1998 | Howitz et al. | |
| 5,746,901 A | 5/1998 | Balch et al. | |
| 5,755,942 A | 5/1998 | Zanzucchi et al. | |
| 5,770,029 A | 6/1998 | Nelson et al. | |
| 5,793,485 A | 8/1998 | Gourley | |
| 5,795,158 A | 8/1998 | Warinner | |
| 5,798,222 A | 8/1998 | Goix | |
| 5,807,677 A | 9/1998 | Eigen et al. | |
| 5,858,195 A | 1/1999 | Ramsey | |
| 5,863,801 A | 1/1999 | Southgate et al. | |
| 5,949,532 A | 9/1999 | Schrof et al. | |
| 5,955,028 A | 9/1999 | Chow | |
| 5,989,402 A | 11/1999 | Chow et al. | |
| 5,999,250 A | 12/1999 | Hairston et al. | |
| 6,033,628 A | 3/2000 | Kaltenbach et al. | |
| 6,041,515 A | 3/2000 | Ally et al. | |
| 6,049,380 A | 4/2000 | Goodwin et al. | |
| 6,071,478 A | 6/2000 | Chow | |
| 6,114,180 A | 9/2000 | Doth et al. | |
| 6,131,101 A | 10/2000 | Maitino et al. | |
| 6,132,580 A | 10/2000 | Mathies et al. | |
| 6,140,048 A | 10/2000 | Muller et al. | |
| 6,143,152 A | 11/2000 | Simpson et al. | |
| 6,177,277 B1 | 1/2001 | Soini | |
| 6,208,815 B1 | 3/2001 | Seidel et al. | |
| 6,211,955 B1 | 4/2001 | Basiji et al. | |
| 6,242,266 B1 | 6/2001 | Schleifer et al. | |
| 6,249,341 B1 | 6/2001 | Basiji et al. | |
| 6,280,960 B1 | 8/2001 | Carr | |
| 6,309,886 B1 | 10/2001 | Ambrose et al. | |
| 6,355,420 B1 | 3/2002 | Chan | |
| 6,361,671 B1 | 3/2002 | Mathies et al. | |
| 6,386,219 B1 | 5/2002 | Barth et al. | |
| 6,388,746 B1 | 5/2002 | Eriksson et al. | |
| 6,394,305 B1 | 5/2002 | Sydlosky et al. | |
| 6,403,338 B1 | 6/2002 | Knapp et al. | |
| 6,403,947 B1 | 6/2002 | Hoyt et al. | |
| 6,473,176 B2 | 10/2002 | Basiji et al. | |
| 6,495,104 B1 | 12/2002 | Unno et al. | |
| 6,506,609 B1 | 1/2003 | Wada et al. | |
| 6,532,067 B1 | 3/2003 | Chang et al. | |
| 6,533,553 B2 | 3/2003 | Caren | |
| 6,537,437 B1 | 3/2003 | Galambos et al. | |
| 6,554,744 B2 | 4/2003 | Schmidt | |
| 6,582,903 B1 | 6/2003 | Rigler et al. | |
| 6,599,436 B1 | 7/2003 | Matzke et al. | |
| 6,608,680 B2 | 8/2003 | Basiji et al. | |
| 6,623,613 B1 | 9/2003 | Mathies et al. | |
| 6,689,323 B2 | 2/2004 | Fisher et al. | |
| 6,710,871 B1 | 3/2004 | Goix | |
| 6,741,344 B1 | 5/2004 | Stern et al. | |
| 6,749,734 B1 | 6/2004 | Simpson et al. | |
| 6,766,817 B2 | 7/2004 | Da Silva | |
| 6,783,992 B2 | 8/2004 | Robotti et al. | |
| 6,802,342 B2 | 10/2004 | Fernandes et al. | |
| 6,811,668 B1 | 11/2004 | Berndt et al. | |
| 6,816,257 B2 | 11/2004 | Goix | |
| 6,918,404 B2 | 7/2005 | Dias Da Silva | |
| 6,977,305 B2 * | 12/2005 | Leung et al. | 548/450 |
| 7,056,427 B2 | 6/2006 | Yamamoto et al. | |
| 7,066,586 B2 | 6/2006 | Da Silva | |
| 7,476,545 B2 | 1/2009 | Kinjo et al. | |
| 7,572,640 B2 * | 8/2009 | Goix et al. | 436/172 |
| 2001/0040093 A1 | 11/2001 | Yamamoto et al. | |
| 2002/0030812 A1 | 3/2002 | Ortyn et al. | |
| 2002/0167665 A1 * | 11/2002 | Yeung et al. | 356/344 |
| 2003/0029995 A1 | 2/2003 | Mullins et al. | |
| 2003/0078737 A1 | 4/2003 | Keys et al. | |
| 2003/0124592 A1 | 7/2003 | Puskas | |
| 2003/0222007 A1 | 12/2003 | Gu et al. | |
| 2004/0166514 A1 | 8/2004 | Puskas | |
| 2004/0214211 A1 | 10/2004 | Gilmanshin et al. | |
| 2005/0164205 A1 | 7/2005 | Puskas | |
| 2005/0221408 A1 | 10/2005 | Nalefski et al. | |
| 2006/0003333 A1 | 1/2006 | Puskas | |
| 2006/0004188 A1 | 1/2006 | Leung et al. | |
| 2006/0078915 A1 | 4/2006 | Fuchs et al. | |
| 2006/0078998 A1 | 4/2006 | Puskas et al. | |
| 2006/0099638 A1 | 5/2006 | Leung et al. | |
| 2006/0160209 A1 | 7/2006 | Larson et al. | |
| 2006/0228747 A1 | 10/2006 | Fuchs et al. | |
| 2008/0003685 A1 | 1/2008 | Goix et al. | |
| 2008/0064113 A1 | 3/2008 | Goix et al. | |
| 2008/0158543 A1 | 7/2008 | Puskas et al. | |
| 2008/0171352 A1 | 7/2008 | Goix et al. | |
| 2009/0171590 A1 | 7/2009 | Puskas et al. | |
| 2010/0329929 A1 | 12/2010 | Goix et al. | |

FOREIGN PATENT DOCUMENTS

| | | |
|---|---|---|
| WO | WO 90/10876 A1 | 9/1990 |
| WO | WO 99/55461 A1 | 11/1999 |
| WO | WO 99/58955 | 11/1999 |
| WO | WO 0222883 | 3/2002 |
| WO | WO 2005/033283 | 4/2005 |
| WO | WO 2005051967 | 6/2005 |
| WO | WO 2005/089524 A2 | 9/2005 |
| WO | WO 2005/089524 A3 | 4/2006 |

OTHER PUBLICATIONS

Becker, et al. Three-dimensional photogrammetric particle-tracking velocimetry. Preparing for the Future. 1995; 5(3). Available at http://esapub.esrin.esa.it/pff/pffv5n3/beckv5n3.htm (7 pages).

Bieschke, et al., Ultrasensitive detection of pathological prion protein aggregates by dual-color scanning for intensely fluorescent targets. Proc Natl Acad Sci USA. 2000; 97(10): 5468-5473.

Bouchon, et al. Cutting edge: inflammatory responses can be triggered by TREM-1, a novel receptor expressed on neutrophils and monocytes. *The Journal of Immunology*. 2000; 164(10): 4991-1995.

Brinkmeier, et al. Two-beam cross-correlation: a method to characterize transport phenomena in micrometer-sized structures. *Anal. Chem.* 1999; 71(3): 609-616.

Castro, et al. Fluorescence detection and size measurement of single DNA molecules. *Anal. Chem.* 1993; 65(7): 849-852.

Castro, et al. Single molecule detection: applications to ultrasensitive biochemical analysis. *Applied Optics*. 1995; 34(18): 3218-3222.

Castro, et al. Single-molecule detection of specific nucleic acid sequences in unamplified genomic DNA. *Anal. Chem.* 1997; 69(19): 3915-3920.

Castro, et al. Single-molecule electrophoresis. *Anal. Chem.* 1995; 67(18):3181-3186.

Castro, et al. Ultrasensitive, direct detection of a specific DNA sequence of *Bacillus antracis* in solution. *The Analyst*. 2000; 125: 9-11.

Chan, et al. DNA mapping using microfluidic stretching and single-molecule detection of fluorescent site-specific tags. Genome Res. 2004; 14(6):1137-46.

Chen, et al. Single-molecule detection in capillary electrophoresis: molecular shot noise as a fundamental limit to chemical analysis. *Anal. Chem.* 1996; 68(4): 690-696.

Cohen, et al. Rapid separation and purification of oligonucleotides by high-performance capillary gel electrophoresis. *Proc Natl Acad Sci USA*. 1988; 85(24): 9660-9663.

Colonna, M. Trems in the immune system and beyond. *Nature Reviews: Immunology*. 2003; 3(6): 445-453.

Dovichi, et al. Laser-induced fluorescence of flowing samples as an approach to single-molecule detection in liquids. *Anal. Chem.* 1984; 56(3): 348-354.

Effenhauser, et al. Integrated capillary electrophoresis on flexible silicone microdevices: analysis of DNA restriction fragments and detection of single DNA molecules on microchips. *Anal. Chem.* 1997; 69(17): 3451-3457.

Etzioni, et al. The case for early detection. *Nature Reviews: Cancer*. 2003; 3(4): 243-252.

Fister, et al. Counting single chromphore molecules for ultrasensitive analysis and separations on microchip devices. *Anal. Chem.* 1998; 70(3): 431-437.

Gibot, et al. Plasma level of a triggering receptor expressed on myeloid cells-1: its diagnostic accuracy in patients with suspected sepsis. *Annals of Internal Medicine*. 2004; 141(1): 9-15.

(56) References Cited

OTHER PUBLICATIONS

Gibot, et al. Soluble triggering receptor expressed on myeloid cells and the diagnosis of pneumonia. *The New England Journal of Medicine.* 2004; 350(5): 451-458.

Golde, T. Alzheimer disease therapy: can the amyloid cascade be halted? *The Journal of Clinical Investigation.* 2003; 11(1): 11-18.

Guenard, et al. Two-channel sequential single-molecule measurement. *Anal. Chem.* 1997; 69(13): 2426-2433.

Haab, et al. Single molecule florescence burst detection of DNA fragments separated by capillary electrophoresis. *Anal Chem.* 1995; 67(18): 3253-3260.

Haab, et al. Single-molecule detection of DNA separations in microfabricated capillary electrophoresis chips employing focused molecular streams. *Anal Chem.* 1999; 71(22): 5137-5145.

Haugland, R. P., *Molecular Probes Handbook of Fluorescent Probes and Research Product, Ninth Edition*, 2002, Molecular Probes, Inc.

Keller, et al. Analytical applications of single-molecule detection. *Analytical Chemistry.* 2002; 74(11): 317A-324A.

Klee. Human anti-mouse antibodies. Arch Pathol Lab Med. 2000; 124(6):921-3.

Lecaptain, et al. Two-beam fluorescence cross-correlation spectroscopy in an electrophoretic mobility shift assay. *Anal Chem.* 2002; 74(5): 1171-1176.

Li, et al. Ultrasensitive coincidence fluorescence detection of single DNA molecules. *Anal Chem.* 2003; 75(7): 1664-1670.

Loscher, et al. Counting of single protein molecules at interfaces and application of this technique in early-stage diagnosis. Anal Chem. 1998; 70(15): 3202-5.

Lucey, et al. Type 1 and type 2 cytokine dysregulation in human infectious, neoplastic, and inflammatory diseases. *Clinical Biology Reviews.* 1996; 9(4): 532-562.

Ma, et al. Single-molecule immunoassay and DNA diagnosis. *Electrophoresis.* 2001; 22(3): 421-426.

Nguyen, et al. Detection of single molecules of phycoerythrin in hydrodynamically focused flows by laser-induced fluorescence. *Anal Chem.* 1987; 59(17): 2158-2161.

Peck, et al. Single-molecule fluorescence detection: autocorrelation criterion and experimental realization with phycoerythrim. *Proc Natl Acad Sci USA.* 1989; 86(11): 4087-4091.

Puskas, R. U.S. Appl. No. 10/718,194, entitled "Preparation of defined highly labeled probes", filed Nov. 19, 2003.

Puskas, R. U.S. Appl. No. 10/720,047, entitled "Charge and mass tags for detection and analysis", filed Nov. 19, 2003.

Sauer, et al. Detection and identification of individual antigen molecules in human serum with pulsed semiconductor lasers. Appl. Phys. B. 1997; 65: 427-431.

Shera, et al. Detection of single fluorescent molecules. *Chemical Physics Letters.* 1990; 174(6): 553-557.

Shortreed, et al. High-throughput single-molecule DNA screening based on electrophoresis. *Anal Chem.* 2000; 72(13): 2879-2885.

Sidransky, D. Emerging molecular markers of cancer. *Nature Reviews: Cancer.* 2002; 2(3): 210-219.

Soper, et al. Photon burst detection of single near-infrared fluorescent molecules. *Anal Chem.* 1993; 65(6): 740-747.

Soper, et al. Single-molecule detection in the near-IR using continuous wave diode laser excitation with an avalanche photon detector. Applied Spectroscopy. 1998; 52(1): 1-6.

Tanaka, et al. Protein and polymer analyses up to m/z 100 000 by laser ionization time-of-flight mass spectrometry. Rapid Commun. Mass. Spect. 1988; 2:151-153.

Upatnieks, et al. A kilohertz frame rate cinemagraphic PIV system for laboratory-scale turbulent and unsteady flows. *Experiments in Fluids.* 2002; 32: 87-98.

Van Orden, et al. Single-molecule identification in flowing sample streams by fluorescence burst size and intraburst fluorescence decay rate. *Anal Chem.* 1998; 70(7): 1444-1451.

Wabuyele, et al. Single molecule detection of double-stranded DNA in poly(methylmethacrylate) and polycarbonate microfluidic devices. *Electrophoresis*, Oct. 2001; 22(18): 3939-3948.

Willneff, J. A spatio-temporal matching algorithm for 3D particle tracking velocimetry: a dissertation submitted to the Swiss Federal Institute of Technology Zurich for the degree of Doctoral of Technical Sciences (abstract). Sep. 2003, Diss. ETH No. 15276. Available at http://e-collection.ethbib.ethz.ch/ecol-pool/diss/abstracts/p15276.pdf.

Zhu, et al. Fluorescence multiplexing with time-resolved and spectral discrimination using a near-Ir detector. *Anal Chem.* 2003; 75(10): 2280-2291.

Puskas, et al. U.S. Appl. No. 11/838,114, entitled "System and methods for sample analysis," filed Aug. 13, 2007.

Alexa Fluor Dyes Handbook. Simply the Best and Brightest: Fluorescent Dyes and Conjugates. Invitrogen. Copyright 2005. Molecular Probes 1-33.

Alexa Fluor Succinimidyl Esters. Invitrogen. Revised Jan. 4, 2006; 1-5.

Cohen at al,: "The renal TGF-beta system in the db/db mouse model of diabetic nephropathy," Exp. Nephrol. (1998) vol. 6. pp. 226-233.

D'Antoni ar ail., Rapid quantitative a talysis using a single molecule counting, nal. Chem., 352:97-109 (2006).

Dunbar et al.: Quantitative multiplexed detection of bacterial pathogens: DNA and protein applications of Lurninex LabMap system, J. Microbiol Methods. 2003; 53(2): 245-252.

Eder of al.: "Transforming growth factor-beta1 and beta2 in serum and urine from patients with bladder carcinoma," The J. of Urology (1996) vol. 156, pp. 953-957.

Eskelinen et al.: "A new tumor marker MCA in breast cancer diagnosis," Anticancer Res. (1938), vol. 8, pp. 665-668.

Goix. Slides>from presentation at clinical Biomarkers Summit. Mar. 29-31, 2006. Coronado, CA.

Goix. Fulfilling the promise of biomarkers in drug discovery and development, Drug Discovery + International. Apr./May 6-7, 2007.

Guide to Amine-Reactive Probes., Revise Oct. 13, 2005.

Guide to Labeling Antibodies with Alexa Fluor Dyes, 24-28 (2004).

Kaiser et al.: "Capillary electrophoresis coupled to mass spectrometer for automated and robust polypeptide determination in body fluids for clinical use." Electrophoresis (2004) V. 25, pp. 2044-2055.

Koerbin et al. The Comparative analytical performance of four troponin I assays at low concentration, Ann Clin. Biochem., 42:19-23 (2005).

Nalefski at al.: Single-molecule counting of macromolecular complexes in real time: a novel approach to quantify transcription factor—DNA and antibody-antigen interactions. Faseb Journal (2004) vol. 18, No. 8: C176.

Panchlik-Voloshina et al.: "Alexa dyes, a series of new fluorescent dyes that yield exceptionally bright, phostotabie conjugates," J. Histochem Cytochem (Sep. 1999) vol. 47, No. 9, pp. 1179-1188.

Park. Addressing Unmet Needs in Assay Development. Medical Device Link 1-4, Mar. 2007.

Phillips et al.: "Application of single molecule technology to rapidly map long DNA and study the conformation of stretched DNA," Nucleic Acids Research, vol. 33, pp. 5829-5837 (2005).

Rigler: "Fluorescence correlations, single-molecule detection and large number screening," Applications in Biotechnology. J. Biotechnol. (1995) vol. 41 (2-3): pp. 177-186.

Schiffer et al.: "High resolution proteome/peptidome analysis of body fluids by capillary electrophoresis coupled with MS," Proteomics (2006) V. 6, pp. 5615-5627.

U.S. Appl. No. 11/048,660, entitled: "System and Methods for Sarnple Analysis," filed Jan. 28, 2005, Puskas, Robert S. et al.

U.S. Appl. No. 11/784,186, entitled "Methods and Coimipositlons for Highly Sensitive Analysis of Markers," filed Apr. 4, 2007, Goix, Philippe J.

U.S. Appl. No. 11/784,211 entitled: "Methods and compositions for highly sensitive detection of molecules" filed Apr. 4, 2007, Goix et al.

U.S. Appl. No. 11/1767,196, entitled: "System and Method for Sample Analysis," filed Jun. 22, 2007, Goix, Philippe J et al.

U.S. Appl. No. 12/060,997, entitled: "Methods and Compositions for Highly Sensitive Analysis of Markers," filed Apr. 2, 2008, Goix, Philippe J. et al.

U.S. Appl. No. 12/276,277, entitled: "System and Method for Sample Analysis," filed Nov. 21, 2008, Ruskas, Robert S. et al.

(56) References Cited

OTHER PUBLICATIONS

U.S. Appl. No. 11/830,762, entitled: "Methods and Compositions for Highly Sensitive Detection of Molecules," filed Jul. 30, 2007, Goix, Philippe J. et al.

U.S. Appl. No. 11/838,114, entitled: "System and Method for Sample Analysis," filed Aug. 13, 2007, Puskas, Robert S. et al.

U.S. Appl. No. 60/613,881, entitled "Continuous wave single particle detector," filed Sep. 28, 2004, Puskas.

U.S. Appl. No. 60/624,785, entitled "Sandwich assay for etection of individual molecules," filed Oct. 29, 2004, Puskas.

Von zur Muhlen et al.: "Evaluation of Urine Proteome Pattern Analysis for Its Potential to Refect Coronary Artery Atheroscierosis in Symptomatic Patients," J. Proteom. Res. (2009) V. 8, pp. 335-345.

Wu et al.: Development and preliminary clinical validation of a high sensitivity assay or cardiac troponin using a capillary flow (single molecule) fluorescence detector. Poster presented at Oak Ridge conference. Apr. 22-22, 2006; 52:2157-2159.

Wu, et al., Development and Preliminary Clinical Validation of a High Sensitivity Assay for Cardiac Tropoin Using a Capillary Flow (Single Molecule) Fluorescence Detector. Clinical Chemistry 52:2157-2159 (2006).

Young: Singules Developing Troponin Test for earlier detection of AMI. Medical Device Daily, Dec. 13, 2006.

Zimmerli et al.: in "Urinary Proteomic Biomarkers in Coronary Artery Disease," Mol. Cell Proteomics (Feb. 2008), V. 7, No. 2, pp. 290-298. First Published on Oct. 19, 2007.

DeJong, et al., "Receptor-ligand binding assays: Technologies and Applications", Journal of Chromatography B: Biomedical Sciences & Applications, 829:1-25 (2005).

Piston, D., "Choosing Objective Lenses: The importance of Numerical Aperture and Magnification in Digital Optical Microscopy", Bio9logical bulletin, 195:1-4 (1998).

Wang, et al., "Single-Molecule Tracing on a Fluidic Microchip for Quantitative Detection of Low-Abundance Nucleic Acids", Journal of the American Chemical Society, 127;5354-5359 (2005).

Berlier, et al., "Quantitative Comparison of long-wavelength Alexa Fluor Dyes to Cy Dyes: Fluorescence of the Dyes and their Bioconjugates". The Journal of Histochemistry and Cytochemistry, 51:1699-1712 (2003).

Microscope Technical Info, Numerical Aperture (N.A.), Condenser Lenses and Immersion Oil; Microbus (2007).

Pupil Diameter and Beam Spot Diameter of Objective Lens; Olympus Corporation; Knowledge (2013).

* cited by examiner

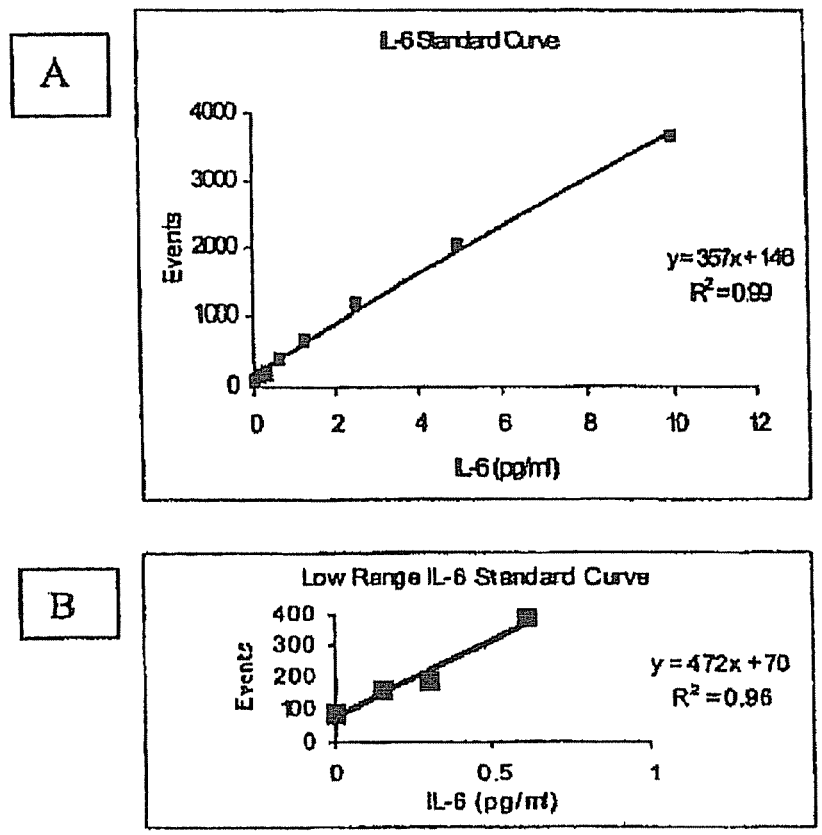
Figure 14 A-B

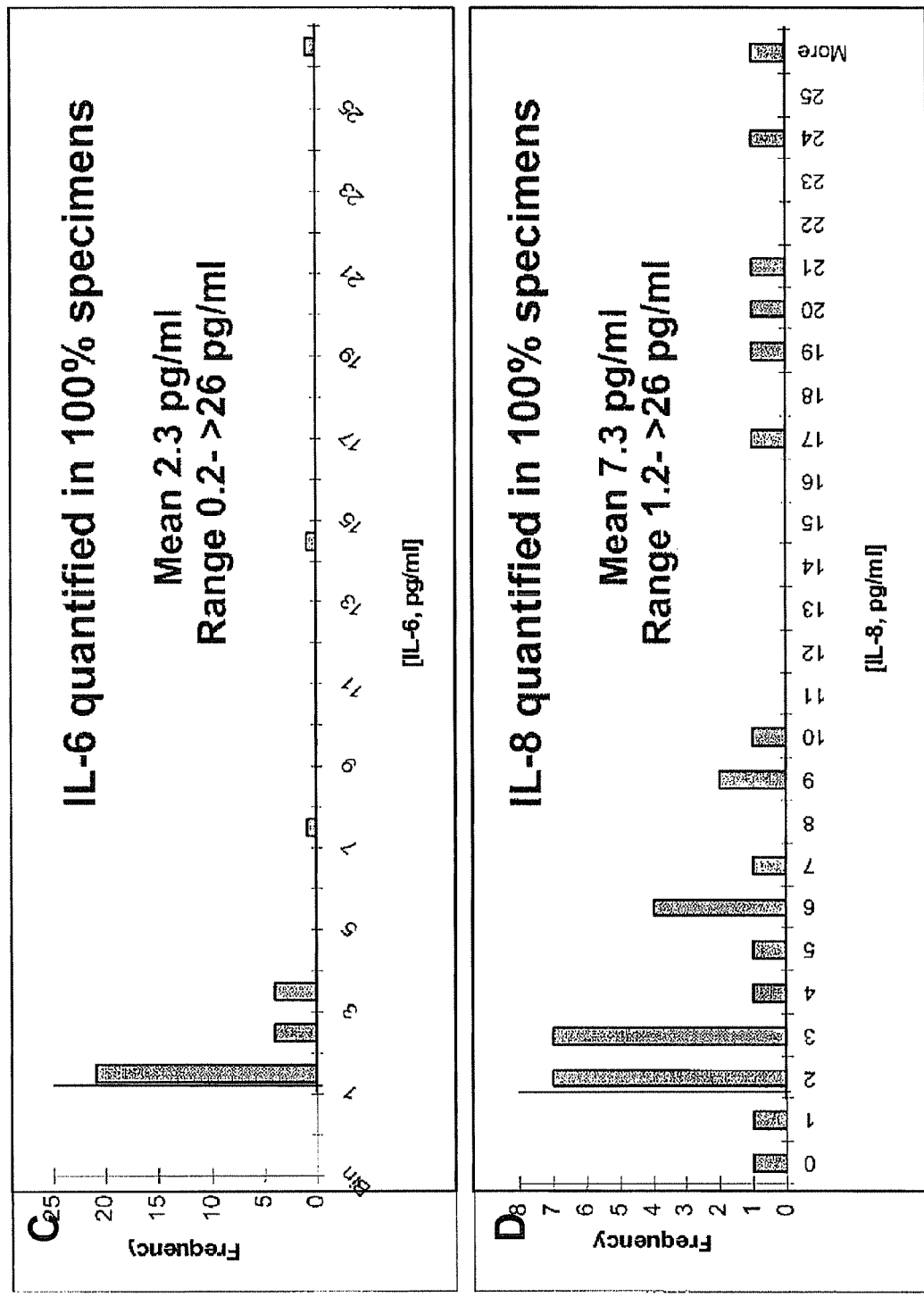
Figure 14 C-D

METHODS AND COMPOSITIONS FOR HIGHLY SENSITIVE DETECTION OF MOLECULES

CROSS-REFERENCE

This application is a continuation application of Ser. No. 11/830,762, filed Jul. 30, 2007, now abandoned, which is a divisional application of Ser. No. 11/784,211, filed Apr. 4, 2007, now U.S. Pat. No. 7,572,640, which is a continuation-in-part application of Ser. No. 11/048,660, filed Jan. 28, 2005, which is incorporated herein by reference in its entirety and to which application we claim priority under 35 USC §120, application Ser. No. 11/048,660 which claims the benefit of U.S. Provisional Application No. 60/613,881, filed Sep. 28, 2004, U.S. Provisional Application No. 60/624,785, filed Oct. 27, 2004, and U.S. Provisional Application No. 60/636,158, filed Dec. 13, 2004.

U.S. patent application Ser. No. 11/830,762 is also a divisional of U.S. patent application Ser. No. 11/784,211, filed Apr. 4, 2007, now U.S. Pat. No. 7,572,640, issued Aug. 11, 2009, which claims priority to U.S. Provisional Application Ser. No. 60/789,304, filed Apr. 4, 2006, U.S. Provisional Application Ser. No. 60/793,664, filed Apr. 19, 2006, U.S. Provisional Application Ser. No. 60/808,662, filed May 26, 2006, U.S. Provisional Application Ser. No. 60/861,498, filed Nov. 28, 2006, and U.S. Provisional Application Ser. No. 60/872,986, filed Dec. 4, 2006. All of these applications are incorporated herein by reference in their entirety.

BACKGROUND OF THE INVENTION

Advances in biomedical research, medical diagnosis, prognosis, monitoring and treatment selection, bioterrorism detection, and other fields involving the analysis of multiple samples of low volume and concentration of analytes have led to development of sample analysis systems capable of sensitively detecting particles in a sample at ever-decreasing concentrations. U.S. Pat. Nos. 4,793,705 and 5,209,834 describe previous systems in which extremely sensitive detection has been achieved. The present invention provides further development in this field.

SUMMARY OF THE INVENTION

In one aspect the invention involves an apparatus.

In some embodiments of the apparatus, the invention involves an analyzer system kit for detecting a single protein molecule in a sample, the kit comprising an analyzer and at least one label comprising a fluorescent moiety and a binding partner for the protein molecule, and where the analyzer contains: a) an electromagnetic radiation source for stimulating the fluorescent moiety; b) a capillary flow cell for passing the label; c) a source of motive force for moving the label in the capillary flow cell; d) an interrogation space defined within the capillary flow cell for receiving electromagnetic radiation emitted from the electromagnetic source; and e) an electromagnetic radiation detector operably connected to the interrogation space for measuring an electromagnetic characteristic of the stimulated fluorescent moiety; where the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules. In some embodiments of the apparatus of the invention, the analyzer system comprises not more than one interrogation space. In some embodiments of the apparatus of the invention, the electromagnetic radiation source is a laser, and where the laser has a power output of at least about 3, 5, 10, or 20 mW. In some embodiments of the apparatus of the invention, the fluorescent moiety involves a fluorescent molecule. In some embodiments, the fluorescent molecule is a dye molecule. In some embodiments, the dye molecule include at least one substituted indolium ring system in which the substituent on the 3-carbon of the indolium ring contains a chemically reactive group or a conjugated substance. In some embodiments, the fluorescent moiety is a quantum dot. In some embodiments of the apparatus of the invention, the electromagnetic radiation source is a continuous wave electromagnetic radiation source. In some embodiments, the continuous wave electromagnetic radiation source is a light-emitting diode or a continuous wave laser. In some embodiments of the apparatus of the invention, the motive force is pressure. In some embodiments of the apparatus of the invention, the detector is an avalanche photodiode detector.

In some embodiments of the apparatus of the invention, the analyzer system further include a confocal optical arrangement for deflecting a laser beam onto the interrogation space and for imaging the stimulated dye molecule, where the confocal optical arrangement comprises an objective lens having a numerical aperture of at least about 0.8. In some embodiments of the apparatus of the invention, the analyzer system further includes a sampling system capable of automatically sampling a plurality of samples and providing a fluid communication between a sample container and the interrogation space. In some embodiments of the apparatus of the invention, the analyzer system further includes a sample recovery system in fluid communication with the interrogation space, where the recovery system is capable of recovering substantially all of the sample.

In some embodiments the invention includes an analyzer for determining the concentration of species in a sample, where the analyzer is capable of determining the concentration over a dynamic range of concentrations of at least about $10^5$. In some embodiments, the dynamic range is from about 1 femtomolar to about 100 picomolar.

In another aspect the invention includes methods.

In some embodiments the invention include a method for determining the presence or absence of a single molecule of a protein in a biological sample, including labeling the molecule with a label and detecting the presence or absence of the label in a single molecule detector, where the label includes a fluorescent moiety that is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules. In some embodiments the single molecule detector comprises not more than one interrogation space. In some embodiments of the methods of the invention, the limit of detection of the single molecule in the sample is less than about 10, 1, 0.1, 0.01, or 0.001 femtomolar. In some embodiments, the limit of detection is less than about 1 femtomolar. In some embodiments of the methods of the invention, detecting the presence or absence of the label in a single molecule detector involves detecting electromagnetic radiation emitted by the fluorescent moiety. In some embodiments of the methods of the invention, the methods further include exposing the fluorescent moiety to electromagnetic radiation. In some embodiments, the electromagnetic radiation is provided by a laser. In some embodiments, the laser stimulates the moiety at a power output of less than about 20 mW. In some embodiments, the laser stimulates the moiety for a duration of less than about 1000, 250, 100, 50, 25 or 10 microseconds. In some embodiments of the methods of the invention, the label further includes a binding partner specific for binding the molecule. In some embodiments, the binding partner is an antibody. In some embodiments of the methods of the invention, the fluorescent moiety comprises a fluorescent dye molecule. In some embodiments, the dye molecule includes at least one substituted indolium ring system in which the substituent on the 3-carbon of the indolium ring contains a chemically reactive group or a conjugated substance. In some embodiments, the dye molecule is an AlexFluor molecule selected from the group consisting of AlexaFluor 488, AlexaFluor 532, AlexaFluor 647, AlexaFluor 680 or AlexaFluor 700. In some embodiments, the dye molecule is an AlexaFluor 647 dye molecule. In some embodiments, the fluorescent moiety comprises a plurality of AlexaFluor 647 molecules. In some embodiments, the plurality of AlexaFluor 647 molecules comprises about 2-4 AlexaFluor 647 molecules. In some embodiments, the fluorescent moiety is a quantum dot. In some embodiments of the methods of the invention, the methods further include measuring the concentration of the protein in the sample. In some embodiments of the methods of the invention, the detecting the presence or absence of the label includes: (i) passing a portion of the sample through an interrogation space; and (ii) subjecting the interrogation space to exposure to electromagnetic radiation, the electromagnetic radiation being sufficient to stimulate the fluorescent moiety to emit photons, if the label is present; and (iii) detecting photons emitted during the exposure of step (ii). In some embodiments of the methods of the invention, the methods further includes determining a background photon level in the interrogation space, where the background level represents the average photon emission of the interrogation space when it is subjected to electromagnetic radiation in the same manner as in step (ii), but without label in the interrogation space. In some embodiments of the methods of the invention, the method further includes comparing the amount of photons detected in step (iii) to a threshold photon level, where the threshold photon level is a function of the background photon level, where an amount of photons detected in step (iii) greater that the threshold level indicates the presence of the label, and an amount of photons detected in step (iii) equal to or less than the threshold level indicates the absence of the label.

In some embodiments the invention involve a method for determining the presence or absence of a biological state in a subject, including: a) performing an immunoassay on a sample from the subject, where the immunoassay comprises binding a plurality of labels for a marker to a plurality of molecules of the marker in the sample, where the label is specific to the marker and where one label binds to one molecule of marker, and where the label comprises an antibody attached to a fluorescent moiety that is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules; b) detecting the labels where the detecting comprises detecting single labels with a single molecule detector; and c) determining a concentration for the marker in the sample based on the number of labels detected in step b). In some embodiments of the methods of the invention, the method further include comparing the concentration obtained in step b) to a concentration or range of concentrations for the marker that are known to be indicative of the presence or absence of the biological state. In some embodiments of the methods of the invention, the subject is a human. In some embodiments, the sample is blood, serum, plasma, urine or exhaled breath condensate.

In another aspect the invention provides compositions.

In some embodiments the invention provides a label for detecting a biological molecule comprising a binding partner for the biological molecule that is attached to a fluorescent moiety, where the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules, where the moiety comprises about 2 to 4 fluorescent entities. In some embodiments of the composition of the invention, the biological molecule is a protein or a small molecule. In some embodiments, the biological molecule is a protein. In some embodiments, the fluorescent entities comprise fluorescent dye molecules. In some embodiments, the fluorescent dye molecules include at least one substituted indolium ring system in which the substituent on the 3-carbon of the indolium ring contains a chemically reactive group or a conjugated substance. In some embodiments, the dye molecules are AlexFluor molecules that can be AlexaFluor 488, AlexaFluor 532, AlexaFluor 647, AlexaFluor 680 or AlexaFluor 700. In some embodiments, the dye molecules are AlexaFluor647 dye molecules. In some embodiments of the methods of the invention, the dye molecules comprise a first type and a second type of dye molecules. In some embodiments, the first type and second type of dye molecules have different emission spectra. In some embodiments, the ratio of the number of first type to second type of dye molecule is 4:1, 3:1, 2:1, 1:1, 1:2, 1:3 or 1:4. In some embodiments of the methods of the invention, the binding partner is an antibody.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A shows the flow cell of an analyzer that includes one electromagnetic source; and FIG. 4B shows the flow cell of an analyzer that includes two electromagnetic sources.

FIGS. 3A and 3B. Schematic diagrams showing the conventional (A) and confocal (B) positioning of laser and detector optics of a single particle analyzer. FIG. 5A shows the arrangement for an analyzer that has one electromagnetic source and one electromagnetic detector; FIG. 5B shows the arrangement for an analyzer that has two electromagnetic sources and two electromagnetic detectors.

DETAILED DESCRIPTION OF THE INVENTION

Figure 1A:
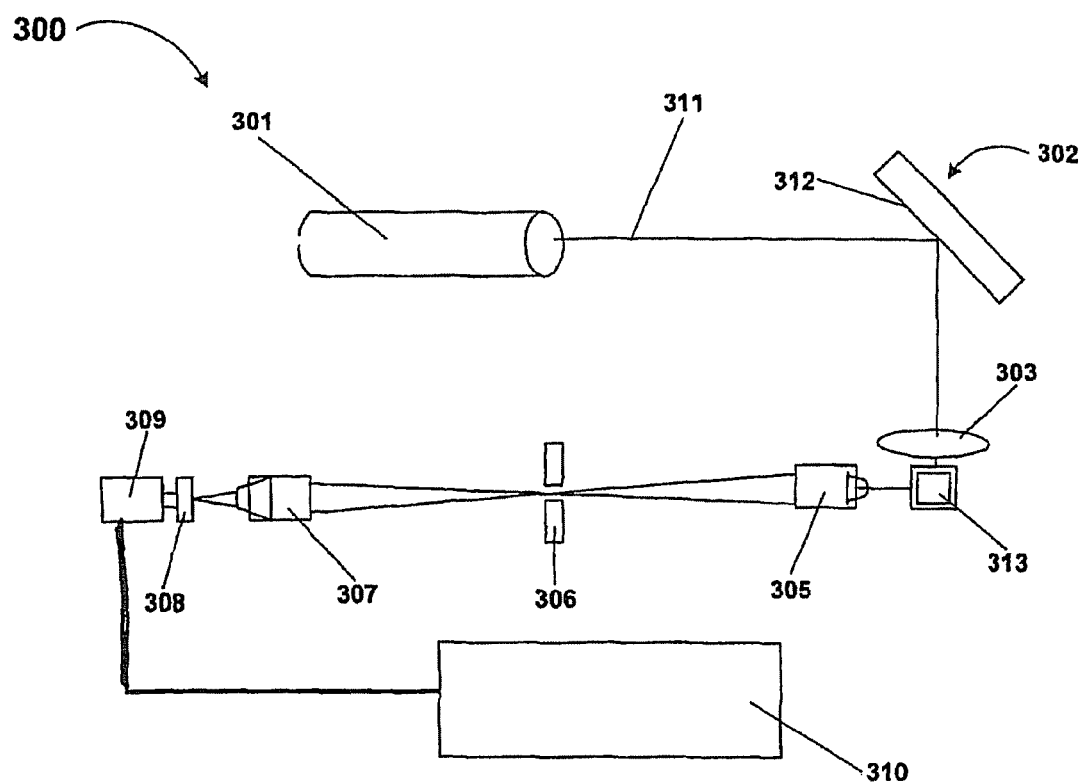
FIGS. 1A and 1B. Schematic diagram of the arrangement of the components of a single particle analyzer.

Outline
I. Introduction
II. Molecules for Sensitive Detection By the Methods and Compositions of the Invention
   A. General
   B. Markers
III. Labels
   A. Binding partners
      1. Antibodies
   B. Fluorescent Moieties
      1. Dyes
      2. Quantum dots
   C. Binding Partner-Fluorescent Moiety Compositions
IV. Highly Sensitive Analysis of Molecules
   A. Sample
   B. Sample preparation
   C. Detection of molecule of interest and determination of concentration
V. Instruments and Systems Suitable for Highly Sensitive Analysis of Molecules
   A. Apparatus/System
   B. Single Particle Analyzer
      1. Electromagnetic Radiation Source
      2. Capillary Flow Cell
      3. Motive Force
      4. Detectors
   C. Sampling System
   D. Sample preparation system
   E. Sample recovery
VI. Methods Using Highly Sensitive Analysis of Molecules
   A. Methods
   B. Exemplary Markers
      1. Cardiac damage
      2. Infectious Diseases
      3. Cytokines
      4. Inflammatory Markers
      5. Markers for a Disease State (Arthritis)
      6. TGFβ
      7. Akt1
      8. Fas ligand
   C. Business Methods
VII. Kits
I. Introduction The invention provides instruments, kits, compositions, and methods for the highly sensitive detection of single molecules, and for the determination of the concentration of the molecules in a sample. The sensitivity and precision of the instruments, compositions, methods, and kits of the invention may be achieved in some embodiments by a combination of factors selected from, but not limited to, electromagnetic sources of appropriate wavelength and power output, appropriate interrogation space size, high numerical aperture lenses, detectors capable of detecting single photons, and data analysis systems for counting single molecules. The instruments of the invention are referred to as "single molecule detectors" or "single particle detectors," and are also encompassed by the terms "single molecule analyzers" and "single particle analyzers." The sensitivity and precision of the kits and methods of the invention are achieved in some embodiments by the use of the instruments of the invention together with by a combination of factors selected from, but not limited to, labels for molecules that exhibit characteristics that allow the molecules to be detected at the level of the single molecule, and methods assaying the label in the instruments described herein.

The instruments, kits, and methods of the invention are especially useful in the sensitive and precise detection of single protein molecules or small molecules, and for the determination of the concentration of said molecules in a sample.

Thus the invention provides, in some embodiments, instruments and kits for the sensitive detection and determination of concentration of molecules by detection of single molecules, labels for such detection and determination, and methods using such instruments and labels in the analysis of samples. In particular, the sensitivity and precision of the instruments, kits, and methods of the invention make possible the detection and determination of concentration of molecules, e.g., markers for biological states, at extremely low concentrations, e.g., concentrations below about 100, 10, 1, 0.1, 0.01, or 0.001 femtomolar. In further embodiments, the instruments and kits of the invention are capable of determining a concentration of a species, e.g., molecule, in a sample over a large dynamic range of concentrations without the need for dilution or other treatment of samples, e.g., over a concentration range of more than $10^5$-fold, $10^6$-fold, or $10^7$-fold The high sensitivity of the instruments, kits, and methods of the invention allows the establishment of uses for markers, e.g., biological markers, that have not previously been possible because of a lack of sensitivity of detection, as well as the establishment of new markers. There are numerous markers currently available which, while potentially of use in determining a biological state, are not currently of practical use because their lower ranges are unknown. In some cases, abnormally high levels of the marker are detectable by current methodologies, but normal ranges have not been established. In some cases, upper normal ranges of the marker are detectable, but not lower normal ranges, or levels below normal. In some cases, for example, markers specific to tumors, or markers of infection, any level of the marker indicates the potential presence of the biological state, and enhancing sensitivity of detection is an advantage for early diagnosis. In some cases, the rate of change, or lack of change, in the concentration of the marker over multiple timepoints provides the most useful information, but present methods of analysis do not permit timepoint sampling in the early stages of a condition, when it is typically at its most treatable. In some cases, the marker may be detected at clinically useful levels only through the use of cumbersome methods that are not practical or useful in a clinical setting, such as methods that require complex sample treatment and time-consuming analysis. In addition, there are potential markers of biological states that exist in sufficiently low concentrations that their presence remains extremely difficult or impossible to detect by current methods.

The analytical methods and compositions of the present invention provide levels of sensitivity, precision, and robustness that allow the detection of markers for biological states at concentrations at which the markers have been previously undetectable, thus allowing the "repurposing" of such markers from confirmatory markers, or markers useful only in limited research settings, to diagnostic, prognostic, treatment-directing, or other types of markers useful in clinical settings and/or in large-scale clinical settings such as clinical trials. Such methods allow the determination of normal and abnormal ranges for such markers The markers thus repurposed can be used for, e.g., detection of normal state (normal ranges), detection of responder/non-responder (e.g., to a treatment, such as administration of a drug); early disease or pathological occurrence detection (e.g., detection of cancer in its earliest stages, early detection of cardiac ischemia); disease staging (e.g., cancer); disease monitoring (e.g., diabetes monitoring, monitoring for recurrence of cancer after treatment); study of disease mechanism; and study of treatment toxicity, such as toxicity of drug treatments.

The invention thus provides methods and compositions for the sensitive detection of markers, and further methods of establishing values for normal and abnormal levels of the markers. In further embodiments, the invention provides methods of diagnosis, prognosis, and/or treatment selection based on values established for the markers. The invention also provides compositions for use in such methods, e.g., detection reagents for the ultrasensitive detection of markers.

II. Molecules for Sensitive Detection by the Methods and Compositions of the Invention The instruments, kits and methods of the invention can be used for the sensitive detection and determination of concentration of a number of different types of single molecules. In particular, the instruments, kits, and methods are useful in the sensitive detection and determination of concentration of markers of biological states. "Detection of a single molecule," as that term is used herein, refers to both direct and indirect detection. For example, a single molecule may be labeled with a fluorescent label, and the molecule-label complex detected in the instruments described herein. Alternatively, a single molecule may be labeled with a fluorescent label, then the fluorescent label is detached from the single molecule, and the label detected in the instruments described herein. The term detection of a single molecule encompasses both forms of detection.

A. General

Examples of molecules which can be detected using the analyzer and related methods of the present invention include: biopolymers such as proteins, nucleic acids, carbohydrates, and small molecules, both organic and inorganic. In particular, the instruments, kits, and methods described herein are useful in the detection of single molecules of proteins and small molecules in biological samples, and the determination of concentration of such molecules in the sample.

The terms "protein," "polypeptide," "peptide," and "oligopeptide," are used interchangeably herein and include any composition that includes two or more amino acids joined together by a peptide bond. It may be appreciated that polypeptides can contain amino acids other than the 20 amino acids commonly referred to as the 20 naturally occurring amino acids. Also, polypeptides can include one or more amino acids, including the terminal amino acids, which are modified by any means known in the art (whether naturally or non-naturally). Examples of polypeptide modifications include e.g., by glycosylation, or other-post-translational modification. Modifications which may be present in polypeptides of the present invention, include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The molecules detected by the present instruments, kits, and methods may be free or may be part of a complex, e.g., an antibody-antigen complex, or more generally a protein-protein complex, e.g., complexes of troponin.

B. Markers of Biological States

In some embodiments, the invention provides compositions and methods for the sensitive detection of biological markers, and for the use of such markers in diagnosis, prognosis, and/or determination of methods of treatment.

Markers of the present invention may be, for example, any composition and/or molecule or a complex of compositions and/or molecules that is associated with a biological state of an organism (e.g., a condition such as a disease or a non-disease state). A marker can be, for example, a small molecule, a polypeptide, a nucleic acid, such as DNA and RNA, a lipid, such as a phospholipid or a micelle, a cellular component such as a mitochondrion or chloroplast, etc. Markers contemplated by the present invention can be previously known or unknown. For example, in some embodiments, the methods herein may identify novel polypeptides that can be used as markers for a biological state of interest or condition of interest, while in other embodiments, known polypeptides are identified as markers for a biological state of interest or condition. Using the systems of the invention it is possible that one can observe those markers, e.g., polypeptides with high potential use in determining the biological state of an organism, but that are only present at low concentrations, such as those "leaked" from diseased tissue. Other high potentially useful markers or polypeptides may be those that are related to the disease, for instance, those that are generated in the tumor-host environment. Any suitable marker that provides information regarding a biological state may be used in the methods and compositions of the invention. A "marker," as that term is used herein, encompasses any molecule that may be detected in a sample from an organism and whose detection or quantitation provides information about the biological state of the organism.

Biological states include but are not limited to phenotypic states; conditions affecting an organism; states of development; age; health; pathology; disease detection, process, or staging; infection; toxicity; or response to chemical, environmental, or drug factors (such as drug response phenotyping, drug toxicity phenotyping, or drug effectiveness phenotyping).

The term "organism" as used herein refers to any living being comprised of a least one cell. An organism can be as simple as a one cell organism or as complex as a mammal. An organism of the present invention is preferably a mammal. Such mammal can be, for example, a human or an animal such as a primate (e.g., a monkey, chimpanzee, etc.), a domesticated animal (e.g., a dog, cat, horse, etc.), farm animal (e.g., goat, sheep, pig, cattle, etc.), or laboratory animal (e.g., mouse, rat, etc.). Preferably, an organism is a human.

In some embodiments, the methods and compositions of the invention are directed to classes of markers, e.g., cytokines, growth factors, oncology markers, markers of inflammation, endocrine markers, autoimmune markers, thyroid markers, cardiovascular markers, markers of diabetes, markers of infectious disease, neurological markers, respiratory markers, gastrointestinal markers, musculoskeletal markers, dermatological disorders, and metabolic markers.

Table 1, below, provides examples of these classes of markers that have been measured by the methods and compositions of the invention, and provides the concentration of the markers as detected by the methods and compositions of the invention and number of particles that are counted by the single particle analyzer system of the invention for the particular marker.

TABLE 1

CLASSES OF MARKERS AND EXEMPLARY MARKERS IN THE CLASSES

| | Molar Conc. | Molecules |
|---|---|---|
| Cytokines | | |
| IL-12 p70 | $2.02 \times 10^{-14}$ | $6.09 \times 10^{+5}$ |
| IL-10 | $5.36 \times 10^{-14}$ | $1.61 \times 10^{+6}$ |
| IL-1 alpha | $5.56 \times 10^{-14}$ | $1.67 \times 10^{+6}$ |
| IL-3 | $5.85 \times 10^{-14}$ | $1.76 \times 10^{+6}$ |
| IL-12 p40 | $6.07 \times 10^{-14}$ | $1.83 \times 10^{+6}$ |
| IL-1ra | $6.12 \times 10^{-14}$ | $1.84 \times 10^{+6}$ |
| IL-12 | $8.08 \times 10^{-14}$ | $2.44 \times 10^{+6}$ |
| IL-6 | $9.53 \times 10^{-14}$ | $2.87 \times 10^{+6}$ |
| IL-4 | $1.15 \times 10^{-13}$ | $3.47 \times 10^{+6}$ |
| IL-18 | $1.80 \times 10^{-13}$ | $5.43 \times 10^{+6}$ |
| IP-10 | $1.88 \times 10^{-13}$ | $1.13 \times 10^{+7}$ |
| IL-5 | $1.99 \times 10^{-13}$ | $5.98 \times 10^{+6}$ |
| Eotaxin | $2.06 \times 10^{-13}$ | $1.24 \times 10^{+7}$ |
| IL-16 | $3.77 \times 10^{-13}$ | $1.14 \times 10^{+7}$ |
| MIG | $3.83 \times 10^{-13}$ | $1.15 \times 10^{+7}$ |
| IL-8 | $4.56 \times 10^{-13}$ | $1.37 \times 10^{+7}$ |
| IL-17 | $5.18 \times 10^{-13}$ | $1.56 \times 10^{+7}$ |
| IL-7 | $5.97 \times 10^{-13}$ | $1.80 \times 10^{+7}$ |
| IL-15 | $6.13 \times 10^{-13}$ | $1.84 \times 10^{+7}$ |
| IL-13 | $8.46 \times 10^{-13}$ | $2.55 \times 10^{+7}$ |
| IL-2R (soluble) | $8.89 \times 10^{-13}$ | $2.68 \times 10^{+7}$ |
| IL-2 | $8.94 \times 10^{-13}$ | $2.69 \times 10^{+7}$ |
| LIF/HILDA | $9.09 \times 10^{-13}$ | $5.47 \times 10^{+7}$ |
| IL-1 beta | $1.17 \times 10^{-12}$ | $3.51 \times 10^{+7}$ |
| Fas/CD95/Apo-1 | $1.53 \times 10^{-12}$ | $9.24 \times 10^{+7}$ |
| MCP-1 | $2.30 \times 10^{-12}$ | $6.92 \times 10^{+7}$ |
| Oncology | | |
| EGF | $4.75 \times 10^{-14}$ | $2.86 \times 10^{+6}$ |
| TNF-alpha | $6.64 \times 10^{-14}$ | $8.00 \times 10^{+6}$ |
| PSA (3rd generation) | $1.15 \times 10^{-13}$ | $6.92 \times 10^{+6}$ |
| VEGF | $2.31 \times 10^{-13}$ | $6.97 \times 10^{+6}$ |
| TGF-beta1 | $2.42 \times 10^{-13}$ | $3.65 \times 10^{+7}$ |
| FGFb | $2.81 \times 10^{-13}$ | $1.69 \times 10^{+7}$ |
| TRAIL | $5.93 \times 10^{-13}$ | $3.57 \times 10^{+7}$ |
| TNF-RI (p55) | $2.17 \times 10^{-12}$ | $2.62 \times 10^{+8}$ |
| Inflammation | | |
| ICAM-1 (soluble) | $8.67 \times 10^{-15}$ | $5.22 \times 10^{+4}$ |
| RANTES | $6.16 \times 10^{-14}$ | $3.71 \times 10^{+6}$ |
| MIP-2 | $9.92 \times 10^{-14}$ | $2.99 \times 10^{+6}$ |
| MIP-1 beta | $1.98 \times 10^{-13}$ | $5.97 \times 10^{+6}$ |
| MIP-1 alpha | $2.01 \times 10^{-13}$ | $6.05 \times 10^{+6}$ |
| MMP-3 | $1.75 \times 10^{-12}$ | $5.28 \times 10^{+7}$ |
| Endocrinology | | |
| 17 beta-Estradiol (E2) | $4.69 \times 10^{-14}$ | $2.82 \times 10^{+6}$ |
| DHEA | $4.44 \times 10^{-13}$ | $2.67 \times 10^{+7}$ |
| ACTH | $1.32 \times 10^{-12}$ | $7.96 \times 10^{+7}$ |
| Gastrin | $2.19 \times 10^{-12}$ | $1.32 \times 10^{+8}$ |
| Growth Hormone (hGH) | $2.74 \times 10^{-12}$ | $1.65 \times 10^{+8}$ |
| Autoimmune | | |
| GM-CSF | $1.35 \times 10^{-13}$ | $8.15 \times 10^{+6}$ |
| C-Reactive Protein (CRP) | $3.98 \times 10^{-13}$ | $2.40 \times 10^{+7}$ |
| G-CSF | $1.76 \times 10^{-12}$ | $1.06 \times 10^{+8}$ |

TABLE 1-continued

CLASSES OF MARKERS AND EXEMPLARY MARKERS IN THE CLASSES

| | Molar Conc. | Molecules |
|---|---|---|
| Thyroid | | |
| Cyclic AMP | $9.02 \times 10^{-15}$ | $5.43 \times 10^{+5}$ |
| Calcitonin | $3.25 \times 10^{-14}$ | $1.95 \times 10^{+6}$ |
| Parathyroid Hormone (PTH) | $1.56 \times 10^{-13}$ | $9.37 \times 10^{+6}$ |
| Cardiovascular | | |
| B-Natriuretic Peptide | $2.86 \times 10^{-13}$ | $1.72 \times 10^{+7}$ |
| NT-proBNP | $2.86 \times 10^{-12}$ | $8.60 \times 10^{+7}$ |
| C-Reactive Protein, HS | $3.98 \times 10^{-13}$ | $2.40 \times 10^{+7}$ |
| Beta-Thromboglobulin (BTG) | $5.59 \times 10^{-13}$ | $3.36 \times 10^{+7}$ |
| Diabetes | | |
| C-Peptide | $2.41 \times 10^{-15}$ | $1.45 \times 10^{+5}$ |
| Leptin | $1.89 \times 10^{-13}$ | $1.14 \times 10^{+7}$ |
| Infectious Dis. | | |
| IFN-gamma | $2.08 \times 10^{-13}$ | $1.25 \times 10^{+7}$ |
| IFN-alpha | $4.55 \times 10^{-13}$ | $2.74 \times 10^{+7}$ |
| Metabolism | | |
| Bio-Intact PTH (1-84) | $1.59 \times 10^{-12}$ | $1.44 \times 10^{+8}$ |
| PTH | $1.05 \times 10^{-13}$ | $9.51 \times 10^{+6}$ |

Cytokines For both research and diagnostics, cytokines are useful as markers of a number of conditions, diseases, pathologies, and the like, and the compositions and methods of the invention include labels for detection and quantitation of cytokines and methods using such labels to determine normal and abnormal levels of cytokines, as well as methods of diagnosis, prognosis, and/or determination of treatment based on such levels.

There are currently over 100 cytokines/chemokines whose coordinate or discordant regulation is of clinical interest. In order to correlate a specific disease process with changes in cytokine levels, the ideal approach requires analyzing a sample for a given cytokine, or multiple cytokines, with high sensitivity. Exemplary cytokines that are presently used in marker panels and that may be used in methods and compositions of the invention include, but are not limited to, BDNF, CREB pS133, CREB Total, DR-5, EGF,ENA-78, Eotaxin, Fatty Acid Binding Protein, FGF-basic, granulocyte colony-stimulating factor (G-CSF), GCP-2, Granulocyte-macrophage Colony-stimulating Factor GM-CSF (GM-CSF), growth-related oncogene—keratinocytes (GRO-KC), HGF, ICAM-1, IFN-alpha, IFN-gamma, the interleukins IL-10, IL-11, IL-12, IL-12 p40, IL-12 p40 p70, IL-12 p70, IL-13, IL-15, IL-16, IL-17, IL-18, IL-1alpha, IL-1beta, IL-1ra, IL-1ra/IL-1F3, IL-2, IL-3, IL-4, IL-5, IL-6, IL-7, IL-8, IL-9, interferon-inducible protein (10 IP-10), JE/MCP-1, keratinocytes (KC), KC/GROa, LIF, Lymphotactin, M-CSF, monocyte chemoattractant protein-1 (MCP-1), MCP-1(MCAF), MCP-3, MCP-5, MDC, MIG, macrophage inflammatory (MIP-1 alpha), MIP-1 beta, MIP-1 gamma, MIP-2, MIP-3 beta, OSM, PDGF-BB, regulated upon activation, normal T cell. expressed and secreted (RANTES), Rb (pT821), Rb (total), Rb pSpT249/252, Tau (pS214), Tau (pS396), Tau (total), Tissue Factor, tumor necrosis factor-alpha (TNF-alpha), TNF-beta, TNF-R1, TNF-R11, VCAM-1, and VEGF. In some embodiments, the cytokine is IL-12p70, IL-10, IL-1 alpha, IL-3, IL-12 p40, IL-Ira, IL-12, IL-6, IL-4, IL-18, IL-10, IL-5, eotaxin, IL-16, MIG, IL-8, IL-1 7, IL-7, IL-1 5, IL-1 3, IL-2R (soluble), IL-2, LIF/HILDA, IL-1 beta, Fas/CD95/Apo-1, or MCP-1.

Growth factors Growth factors include EGF Ligands such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, LRIG1; EGF R/ErbB Receptor Family such as EGF R, ErbB3, ErbB2, ErbB4; FGF Family such as FGF LigandsFGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-22, FGF-10, FGF-23, FGF-11, KGF/FGF-7, FGF Receptors FGF R1-4, FGF R3, FGF R1, FGF R4, FGF R2, FGF R5, FGF Regulators FGF-BP; the Hedgehog Family Desert Hedgehog, Sonic Hedgehog, Indian Hedgehog; Hedgehog Related Molecules & Regulators BOC, GLI-3, CDO, GSK-3 alpha/beta, DISP1, GSK-3 alpha, Gas 1, GSK-3 beta, GLI-1, Hip, GLI-2; the IGF FamilyIGF Ligand-sIGF-I, IGF-II, IGF-I Receptor (CD221)IGF-I R, and IGF Binding Protein (IGFBP) Family ALS, IGFBP-5, CTGF/CCN2, IGFBP-6, Cyr61/CCN1, IGFBP-L1, Endocan, IGFBP-rp1/IGFBP-7, IGFBP-1, IGFBP-rP10, IGFBP-2, NOV/CCN3, IGFBP-3, WISP-1/CCN4, IGFBP-4; Receptor Tyrosine Kinases Ax1, FGF R4, C1q R1/CD93, FGF R5, DDR1, Flt-3, DDR2, HGF R, Dtk, IGF-I R, EGF, R IGF-II R, Eph, INSRR, EphA1, Insulin R/CD220, EphA2, M-CSF R, EphA3, Mer, EphA4, MSP R/Ron, EphA5, MuSK, EphA6, PDGF R alpha, EphA7, PDGF R beta, EphA8, Ret, EphB1, RTK-like Orphan Receptor 1/ROR1, EphB2, RTK-like Orphan Receptor 2/ROR2, EphB3, SCF R/c-kit, EphB4, Tie-1, EphB6, Tie-2, ErbB2, TrkA, ErbB3, TrkB, ErbB4, TrkC, FGF, R1-4 VEGF R, FGF R1, VEGF R1/Flt-1, FGF R2, VEGF R2/KDR/Flk-1, FGF R3, VEGF R3/Flt-4; Proteoglycans & Regulators Proteoglycans Aggrecan, Mimecan, Agrin, NG2/MCSP, Biglycan, Osteoadherin, Decorin, Podocan, DSPG3, delta-Sarcoglycan, Endocan, Syndecan-1/CD138, Endoglycan, Syndecan-2, Endorepellin/Perlecan, Syndecan-3, Glypican 2, Syndecan-4, Glypican 3, Testican 1/SPOCK1, Glypican 5, Testican 2/SPOCK2, Glypican 6, Testican 3/SPOCK3, Lumican, Versican, Proteoglycan Regulators Arylsulfatase A/ARSA, Glucosamine (N-acetyl)-6-Sulfatase/GNS, Exostosin-like 2/EXTL2, HS6ST2, Exostosin-like 3/EXTL3, Iduronate 2-Sulfatase/IDS, GalNAc4S-6ST; SCF, Flt-3 Ligand & M-CSF Flt-3, M-CSF R, Flt-3 Ligand, SCF, M-CSF, SCF R/c-kit; TGF-beta Superfamily (same as listed for inflammatory markers); VEGF/PDGF Family Neuropilin-1, P1GF, Neuropilin-2, P1GF-2, PDGF, VEGF, PDGF R alpha, VEGF-B, PDGF R beta, VEGF-C, PDGF-A, VEGF-D, PDGF-AB, VEGF R, PDGF-B, VEGF R1/Flt-1, PDGF-C, VEGF R2/KDR/Flk-1, PDGF-D, VEGF R3/Flt-4; Wnt-related Molecules Dickkopf Proteins & Wnt InhibitorsDkk-1, Dkk-4, Dkk-2, Soggy-1, Dkk-3, WIF-1 Frizzled & Related Proteins Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP Wnt Ligands Wnt-1, Wnt-8a, Wnt-2b, Wnt-8b, Wnt-3a, Wnt-9a, Wnt-4, Wnt-9b, Wnt-5a, Wnt-10a, Wnt-5b, Wnt-10b, Wnt-7a, Wnt-11, Wnt-7b; Other Wnt-related Molecules APC, Kremen-2, Axin-1, LRP-1, beta-Catenin, LRP-6, Dishevelled-1, Norrin, Dishevelled-3, PKC beta 1, Glypican 3, Pygopus-1, Glypican 5, Pygopus-2, GSK-3 alpha/beta, R-Spondin 1, GSK-3 alpha, R-Spondin 2, GSK-3 beta, R-Spondin 3, ICAT, RTK-like Orphan Receptor 1/ROR1, Kremen-1, RTK-like Orphan Receptor 2/ROR, and Other Growth Factors CTGF/CCN2, beta-NGF, Cyr61/CCN1, Norrin, DANCE, NOV/CCN3, EG-VEGF/PK1, Osteocrin, Hepassocin, PD-ECGF, HGF, Progranulin, LECT2, Thrombopoietin, LEDGF, WISP-1/CCN4.

Markers of Inflammation Markers of inflammation include ICAM-1, RANTES, MIP-2, MIP-1-beta, MIP-1-alpha, and MMP-3. Further markers of inflammation include Adhesion molecules such as the integrins α1,β1, α2β1, αβ1, α4β1, α5β1, α6β1, α7β1, α8β1, α9β1, αVβ1, α4β7, α6β4, αDβ2, αLβ2, αMβ2, αVβ3, αVβ5, αVβ6, αVβ8, αXβ2, αIIbβ3, ☐IELbβ7, beta-2 integrin, beta-3 integrin, beta-2 integrin, beta-4 integrin, beta-5 integrin, beta-6 integrin, beta-7 integrin, beta-8 integrin, alpha-1 integrin, alpha-2 integrin, alpha-3 integrin, alpha-4 integrin, alpha-5 integrin, alpha-6 integrin, alpha-7 integrin, alpha-8 integrin, alpha-9 integrin, alpha-D integrin, alpha-L integrin, alpha-M integrin, alpha-V integrin, alpha-X integrin, alpha-IIb integrin, alphaIELb integrin; Integrin-associated Molecules such as Beta IG-H3, Melusin, CD47, MEPE, CD151, Osteopontin, IBSP/Sialoprotein II, RAGE, IGSF8; Selectins such as E-Selectin, P-Selectin, L-Selectin; Ligands such as CD34, GlyCAM-1, MadCAM-1, PSGL-1, vitronectic, vitronectin receptor, fibronectin, vitronectin, collagen, lanminin. ICAM-1, ICAM-3, BL-CAM, LFA-2, VCAM-1, NCAM, PECAM. Further markers of inflammation include Cytokines such as IFN-α, IFN-β, IFN-α, -κ, -τ, and -ζ, IFN-ω, IFN-γ, IL29, IL28A and IL28B, IL-1, IL-1☐ and .☐, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, TCCR/WSX-1. Further markers of inflammation include cytokine receptors such as Common beta chain, IL-3 R alpha, IL-3 R beta, GM-CSF R, IL-5 R alpha, Common gamma Chain/IL-2 R gamma, IL-2 R alpha, IL-9 R, IL-2 R beta, IL-4 R, IL-21 R, IL-15 R alpha, IL-7 R alpha/CD127, IL-1ra/IL-1F3, IL-1 R8, IL-1 R1, IL-1 R9, IL-1 R11, IL-18 Ralpha/IL-1 R5, IL-1 R3/IL-1 RAcP, IL-18 Rbeta/IL-1 R7, IL-1 R4/ST2 SIGIRR, IL-1 R6/IL-1 R rp2, IL-11R alpha, IL-31 RA, CNTF R alpha, Leptin R, G-CSF R, LIF R alpha, IL-6 R, OSM R beta, IFN-alpha/beta R1, IFN-alpha/beta R2, IFN-gamma R1, IFN-gamma R2, IL-10 R alpha, IL-10 R beta, IL-20 R alpha, IL-20 Rbeta, IL-22 R, IL-17 R, IL-17 RD, IL-17 RC, IL-17B R, IL-13 R alpha 2, IL-23 R, IL-12 Rbeta 1, IL-12 Rbeta 2, TCCR/WSX-1, IL-13 R alpha 1. Further markers of inflammation include Chemokines such as CCL-1, CCL-2, CCL-3, CCL-4, CCL-5, CCL-6, CCL-7, CCL-8, CCL-9, CCL-10, CCL-11, CCL-12, CCL-13, CCL-14, CCL-15, CCL-16, CCL-17, CCL-18, CCL-19, CCL-20, CCL-21, CCL-22, CCL-23, CCL-24, CCL-25, CCL-26, CCL-27, CCL-28, MCK-2, MIP-2, CINC-1, CINC-2, KC, CINC-3, LIX, GRO, Thymus Chemokine-1, CXCL-1, CXCL-2, CXCL-3, CXCL-4, CXCL-5, CXCL-6, CXCL-7, CXCL-8, CXCL-9, CXCL-10, CXCL-11, CXCL-12, CXCL-13, CXCL-14, CXCL-15, CXCL-16, CXCL-17, XCL1, XCL2, Chemerin. Further markers of inflammation include Chemokine receptors such as CCR-1, CCR-2, CCR-3, CCR-4, CCR-5, CCR-6, CCR-7, CCR-8, CCR-9, CCR-10, CXCR3, CXCR6, CXCR4, CXCR1, CXCR5, CXCR2, Chem R23. Further markers of inflammation include Tumor necrosis factors (TNFs), such as TNF.alpha., 4-1BB Ligand/TNFSF9, LIGHT/TNFSF14, APRIL/TNFSF13, Lymphotoxin, BAFF/TNFSF13B, Lymphotoxin beta/TNFSF3, CD27 Ligand/TNFSF7, OX40 Ligand/TNFSF4, CD30 Ligand/TNFSF8, TL1A/TNFSF15, CD40 Ligand/TNFSF5, TNF-alpha/TNFSF1A, EDA, TNF-beta/TNFSF1B, EDA-A2, TRAIL/TNFSF10, Fas Ligand/TNFSF6, TRANCE/TNFSF11, GITR Ligand/TNFSF18,TWEAK/TNFSF12. Further markers of inflammation include TNF Superfamily Receptors such as 4-1BB/TNFRSF9, NGF R/TNFRSF16, BAFF R/TNFRSF13C, Osteoprotegerin/TNFRSF 11B, BCMA/TNFRSF17, OX40/TNFRSF7, CD27/TNFRSF7, RANK/TNFRSF11A, CD30/TNFRSF8, RELT/TNFRSF19L, CD40/TNFRSF5, TACI/TNFRSF13B, DcR3/TNFRSF6B, TNF R1/TNFRSF1A, DcTRAIL R1/TNFRSF23, TNF R11/TNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF10D, Fas/TNFRSF6, TROY/TNFRSF19, GITR/TNRSF18, TWEAK R/TNFRSF12, HVEM/TNFRSF14, XEDAR. Further markers of inflammation include TNF Superfamily Regulators such as FADD, TRAF-2, RIP1, TRAF-3, TRADD, TRAF-4, TRAF-1, TRAF-6. Further markers of inflammation include Acute-phase reactants and acute phase proteins. Further markers of inflammation include TGF-beta superfamily ligands such as Activins, Activin A, Activin B, Activin AB, Activin C, BMPs (Bone Morphogenetic Proteins), BMP-2, BMP-7, BMP-3, BMP-8, BMP-3b/GDF-10, BMP-9, BMP-4, BMP-10, BMP-5, BMP-15/GDF-9B, BMP-6, Decapentaplegic, Growth/Differentiation Factors (GDFs), GDF-1, GDF-8, GDF-3, GDF-9 GDF-5, GDF-11, GDF-6, GDF-15, GDF-7, GDNF Family Ligands, Artemin, Neurturin, GDNF, Persephin, TGF-beta, TGF-beta, TGF-beta 3, TGF-beta 1, TGF-beta 5, LAP (TGF-beta 1), Latent TGF-beta bp1, Latent TGF-beta 1, Latent TGF-beta bp2, TGF-beta 1.2, Latent TGF-beta bp4, TGF-beta 2, Lefty, MIS/AMH, Lefty-1, Nodal, Lefty-A, Activin RIA/ALK-2, GFR alpha-1/GDNF R alpha-1, Activin RIB/ALK-4, GFR alpha-2/GDNF R alpha-2, Activin RIIA, GFR alpha-3/GDNF R alpha-3, Activin RIIB, GFR alpha-4/GDNF R alpha-4, ALK-1, MIS R11, ALK-7, Ret, BMPR-IA/ALK-3, TGF-beta R1/ALK-5, BMPR-IB/ALK-6, TGF-beta R11, BMPR-II, TGF-beta R1Mb, Endoglin/CD105, TGF-beta RIII. Further markers of inflammation include TGF-beta superfamily Modulators such as Amionless, NCAM-1/CD56, BAMBI/NMA, Noggin, BMP-1/PCP, NOMO, Caronte, PRDC, Cerberus 1, SKI, Chordin, Smad1, Chordin-Like 1, Smad2, Chordin-Like 2, Smad3, COCO, Smad4, CRIM1, Smad5, Cripto, Smad7, Crossveinless-2, Smad8, Cryptic, SOST, DAN, Latent TGF-beta bp1, Decorin, Latent TGF-beta bp2, FLRG, Latent TGF-beta bp4, Follistatin, TMEFF1/Tomoregulin-1, Follistatin-like 1, TMEFF2, GASP-1/WFIKKNRP, TSG, GASP-2/WFIKKN, TSK, Gremlin, Vasorin. Further markers of inflammation include EGF Ligands such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, LRIG1. Further markers of inflammation include EGF R/ErbB Receptor Family, such as EGF R, ErbB3, ErbB2, ErbB4. Further markers of inflammation include Fibrinogen. Further markers of inflammation include SAA. Further markers of inflammation include glial markers, such as alpha. 1-antitrypsin, C-reactive protein (CRP), .alpha.2-macroglobulin, glial fibrillary acidic protein (GFAP), Mac-1, F4/80. Further markers of inflammation include myeloperoxidase. Further markers of inflammation include Complement markers such as C3d, C1q, C5, C4d, C4 bp, and C5a-C9. Further markers of inflammation include Major histocompatibility complex (MHC) glycoproteins, such as HLA-DR and HLA-A, D,C. Further markers of inflammation include Microglial markers, such as CR3 receptor, MHC I, MHC II, CD 31, CD11a, CD11b, CD11c, CD68, CD45RO, CD45RD, CD18, CD59, CR4, CD45, CD64, and CD44. Further markers of inflammation include alpha.2 macroglobulin receptor, Fibroblast growth factor, Fc gamma R1, Fc gamma R11, CD8, LCA (CD45), CD18 ( ), CD59, Apo J, clusterin, type 2 plasminogen activator inhibitor, CD44, Macrophage colony stimulating factor receptor, MRP14, 27E10, 4-hydroxynonenal-protein conjugates, I.kappa.B, NF.kappa.B, cPLA.sub.2, COX-2, Matrix metalloproteinases, Membrane lipid peroxidation, and ATPase activity. HSPC228, EMP1, CDC42, TLE3, SPRY2, p40BBP, HSPC060 or NAB2, or a down-regulation of HSPA1A, HSPA1B, MAPRE2 and OAS1 expression, TACE/ADAM 17, alpha-1-Acid Glycoprotein, Angiopoietin-1, MIF, Angiopoietin-2, CD14, beta-Defensin 2, MMP-2, ECF-L/ CHI3L3, MMP-7, EGF, MMP-9, EMAP-II, MSP, EN-RAGE, Nitric Oxide, Endothelin-1, Osteoactivin/GP-NMB, FPR1, PDGF, FPRL1, Pentraxin 3/TSG-14, FPRL2, Gas6, PLUNC, GM-CSF, RAGE, S100A10, S100A8, S100A9, HIF-1 alpha, Substance P, TFPI, TGF-beta 1, TIMP-1, TIMP-2, TIMP-3, TIMP-4, TLR4, LBP, TREM-1, Leukotriene A4, Hydrolase TSG-6, Lipocalin-1, uPA, M-CSF, and VEGF Oncology markers include EGF, TNF-alpha, PSA, VEGF, TGF-beta1, FGFb, TRAIL, and TNF-R1 (p55)

Markers of endocrine function include 17 beta-estradiol (E2), DHEA, ACTH, gastrin, and growth hormone (hGH).

Marker of autoimmunity include GM-CSF, C-Reactive Protein, and G-CSF.

Markers of thyroid function include cyclicAMP, calcitonin, and parathyroid hormone.

Cardiovascular markers include cardiac troponin I, cardiac troponin T, B-natriuretic peptide, NT-proBNP, C-ractive Protein HS, and betatrhromboglobulin.

Makers of diabetes include C-peptide and leptin.

Markers of infectious disease include IFN-gamma and IFN-alpha.

Markers of metabolism include Bio-intact PTH (1-84) and PTH.

Markers of biological states Markers may indicate the presence of a particular phenotypic state of interest. Examples of phenotypic states include, phenotypes resulting from an altered environment, drug treatment, genetic manipulations or mutations, injury, change in diet, aging, or any other characteristic(s) of a single organism or a class or subclass of organisms.

In some embodiments, a phenotypic state of interest is a clinically diagnosed disease state. Such disease states include, for example, cancer, cardiovascular disease, inflammatory disease, autoimmune disease, neurological disease, infectious disease and pregnancy related disorders. Alternatively, states of health can be detected using markers.

Cancer phenotypes are included in some aspects of the invention. Examples of cancer herein include, but are not limited to: breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, non-small cell lung carcinoma gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas.

Cardivascular disease may be included in other applications of the invention. Examples of cardiovascular disease include, but are not limited to, congestive heart failure, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, congestive heart failure, myocardial ischemia, myocardial infarction, cardiac tamponade, myocarditis, pericarditis, arrhythmogenic right ventricular dysplasia, hypertrophic cardiomyopathy, Williams syndrome, heart valve diseases, endocarditis, bacterial, pulmonary atresia, aortic valve stenosis, Raynaud's disease, Raynaud's disease, cholesterol ernbolism, Wallenberg syndrome, Hippel-Lindau disease, and telangiectasis.

Inflammatory disease and autoimmune disease may be included in other embodiments of the invention. Examples of inflammatory disease and autoimmune disease include, but are not limited to, rheumatoid arthritis, non-specific arthritis, inflammatory disease of the larynx, inflammatory bowel disorder, psoriasis, hypothyroidism (e.g., Hashimoto thyroidism), colitis, Type 1 diabetes, pelvic inflammatory disease, inflammatory disease of the central nervous system, temporal arteritis, polymyalgia rheumatica, ankylosing spondylitis, polyarteritis nodosa, Reiter's syndrome, scleroderma, systemis lupus and erythematosus.

The methods and compositions of the invention can also provide laboratory information about markers of infectious disease including markers of Adenovirus, Bordella pertussis, Chlamydia pneumoiea, Chlamydia trachomais, Cholera Toxin, Cholera Toxin β, Campylobacter jejuni, Cytomegalovirus, Diptheria Toxin, Epstein-Barr NA, Epstein-Barr EA, Epstein-Barr VCA, Helicobacter Pylori, Hepatitis B virus (HBV) Core, Hepatitis B virus (HBV) Envelope, Hepatitis B virus (HBV) Survace (Ay), Hepatitis C virus (HCV) Core, Hepatitis C virus (HCV) NS3, Hepatitis C virus (HCV) NS4, Hepatitis C virus (HCV) NS5, Hepititis A, Hepititis D, Hepatitis E virus (HEV) orf2 3 KD, Hepatitis E virus (HEV) orf2 6 KD, Hepatitis E virus (HEV) orf3 3 KD, Human immunodeficiency virus (HIV)-1 p24, Human immunodeficiency virus (HIV)-1 gp41, Human immunodeficiency virus (HIV)-1 gp120, Human papilloma virus (HPV), Herpes simplex virus HSV-1/2, Herpes simplex virus HSV-1 gD, Herpes simplex virus HSV-2 gG, Human T-cell leukemia virus (HTLV)-1/2, Influenza A, Influenza A H3N2, Influenza B, Leishmanina donovani, Lyme disease, Mumps, *M. pneumoniae, M. teberculosis, Parainfluenza* 1, Parainfluenza 2, Parainfluenza 3, Polio Virus, Respiratory syncytial virus (RSV), Rubella, Rubeola, Streptolysin O, Tetanus Toxin, *T. pallidum* 15 kd, T. pallidum p47, *T. cruzi, Toxoplasma*, and Varicella Zoater.

III. Labels

In some embodiments, the invention provides methods and compositions that include labels for the highly sensitive detection and quantitation of molecules, e.g., of markers.

One skilled in the art will recognize that many strategies can be used for labeling target molecules to enable their detection or discrimination in a mixture of particles. The labels may be attached by any known means, including methods that utilize non-specific or specific interactions of label and target. Labels may provide a detectable signal or affect the mobility of the particle in an electric field. In addition, labeling can be accomplished directly or through binding partners.

In some embodiments, the label comprises a binding partner to the molecule of interest, where the binding partner is attached to a fluorescent moiety. The compositions and methods of the invention may utilize highly fluorescent moieties, e.g., a moiety capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. Moieties suitable for the compositions and methods of the invention are described in more detail below.

In some embodiments, the invention provides a label for detecting a biological molecule comprising a binding partner for said biological molecule that is attached to a fluorescent moiety, wherein said fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the moiety comprises a plurality of fluorescent entities, e.g., about 2-4, 2-5, 2-6, 2-7, 2-8, 2-9, 2-10, or 3-5, 3-6, 3-7, 3-8, 3-9, or 3-10 fluorescent entities. In some embodiments, the moiety comprises about 2 to 4 fluorescent entities. In some embodiments, biological molecule is a protein or a small molecule, In some embodiments the biological molecule is a protein. The fluorescent entities may be fluorescent dye molecules. In some embodiments, the fluorescent dye molecules comprise at least one substituted indolium ring system in which the substituent on the 3-carbon of the indolium ring contains a chemically reactive group or a conjugated substance. In some embodiments, the dye molecules are AlexFluor molecules selected from the group consisting of AlexaFluor 488, AlexaFluor 532, AlexaFluor 647, AlexaFluor 680 or AlexaFluor 700. In some embodiments, the dye molecules are AlexFluor molecules selected from the group consisting of AlexaFluor 488, AlexaFluor 532, AlexaFluor 680 or AlexaFluor 700. In some embodiments, the dye molecules are AlexaFluor647 dye molecules. In some embodiments, the dye molecules comprise a first type and a second type of dye molecules, e.g., two different AlexaFluor molecules, e.g., where the first type and second type of dye molecules have different emission spectra. The ratio of the number of first type to second type of dye molecule may be, e.g., 4:1, 3:1, 2:1, 1:1, 1:2, 1:3 or 1:4. The binding partner may be, e.g., an antibody.

In some embodiments, the invention provides a label for the detection of a marker, wherein the label comprises a binding partner for the marker and a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the fluorescent moiety comprises a fluorescent molecule. In some embodiments, the fluorescent moiety comprises a plurality of fluorescent molecules, e.g., about 2-10, 2-8, 2-6, 2-4, 3-10, 3-8, 3-6 fluorescent molecules. In some embodiments, the label comprises about 2-4 fluorescent molecules. In some embodiments, the fluorescent dye molecules comprise at least one substituted indolium ring system in which the substituent on the 3-carbon of the indolium ring contains a chemically reactive group or a conjugated substance. In some embodiments, the fluorescent molecules are selected from the group consisting of AlexaFluor 488, AlexaFluor 532, AlexaFluor 647, AlexaFluor 680 or AlexaFluor 700. In some embodiments, the fluorescent molecules are selected from the group consisting of AlexaFluor 488, AlexaFluor 532, AlexaFluor 680 or AlexaFluor 700. In some embodiments, the binding partner comprises an antibody. In some embodiments, the antibody is a monoclonal antibody. In some embodiments, antibody is a polyclonal antibody.

The antibody may be specific to any suitable marker. In some embodiments, the antibody is specific to a marker that is selected from the group consisting of cytokines, growth factors, oncology markers, markers of inflammation, endocrine markers, autoimmune markers, thyroid markers, cardiovascular markers, markers of diabetes, markers of infectious disease, neurological markers, respiratory markers, gastrointestinal markers, musculoskeletal markers, dermatological disorders, and metabolic markers.

In some embodiments, the antibody is specific to a marker that is a cytokine. In some embodiments, the cytokine is selected from the group consisting of BDNF, CREB pS133, CREB Total, DR-5, EGF,ENA-78, Eotaxin, Fatty Acid Binding Protein, FGF-basic, granulocyte colony-stimulating factor (G-CSF), GCP-2, Granulocyte-macrophage Colony-stimulating Factor GM-CSF (GM-CSF), growth-related oncogene—keratinocytes (GRO-KC), HGF, ICAM-1, IFN-alpha, IFN-gamma, the interleukins IL-10, IL-11, IL-12, IL-12 p40, IL-12 p40/p70, IL-12 p70, IL-13, IL-15, IL-16, IL-17, IL-18, IL-1alpha, IL-1beta, IL-1ra, IL-1ra/IL-1F3, IL-2, IL-3, IL-4, IL-5, IL-6, IL-7, IL-8, IL-9, interferon-inducible protein (10 IP-10), JE/MCP-1, keratinocytes (KC), KC/GROa, LIF, Lymphotacin, M-CSF, monocyte chemoattractant protein-1 (MCP-1), MCP-1(MCAF), MCP-3, MCP-5, MDC, MIG, macrophage inflammatory (MIP-1 alpha), MIP-1 beta, MIP-1 gamma, MIP-2, MIP-3 beta, OSM, PDGF-BB, regulated upon activation, normal T cell. expressed and secreted (RANTES), Rb (pT82 1), Rb (total), Rb pSpT249/252, Tau (pS214), Tau (pS396), Tau (total), Tissue Factor, tumor necrosis factor-alpha (TNF-alpha), TNF-beta, TNF-R1, TNF-R11, VCAM-1, and VEGF.

In some embodiments, the cytokine is selected from the group consisting of IL-12p70, IL-10, IL-1 alpha, IL-3, IL-12 p40, IL-Ira, IL-12, IL-6, IL-4, IL-18, IL-10, IL-5, Eotaxin, IL-1 6, MIG, IL-8, IL-17, IL-7, IL-15, IL-13, IL-2R (soluble), IL-2, LIF/HILDA, IL-1 beta, Fas/CD95/Apo-1 and MCP-1.

In some embodiments, the antibody is specific to a marker that is a growth factor. In some embodiments, the antibody is specific to a marker that is a growth factor that is TGF-beta. In some embodiments, the growth factor is GF Ligands such as Amphiregulin, LRIG3, Betacellulin, Neuregulin-1/NRG1, EGF, Neuregulin-3/NRG3, Epigen, TGF-alpha, Epiregulin, TMEFF1/Tomoregulin-1, HB-EGF, TMEFF2, LRIG1; EGF R/ErbB Receptor Family such as EGF R, ErbB3, ErbB2, ErbB4; FGF Family such as FGF LigandsFGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-22, FGF-10, FGF-23, FGF-11, KGF/FGF-7, FGF Receptors FGF R1-4, FGF R3, FGF R1, FGF R4, FGF R2, FGF R5, FGF Regulators FGF-BP; the Hedgehog Family Desert Hedgehog, Sonic Hedgehog, Indian Hedgehog; Hedgehog Related Molecules & Regulators BOC, GLI-3, CDO, GSK-3 alpha/beta, DISP1, GSK-3 alpha, Gas1, GSK-3 beta, GLI-1, Hip, GLI-2; the IGF FamilyIGF LigandsIGF-I, IGF-II, IGF-I Receptor (CD221)IGF-I R, and IGF Binding Protein (IGFBP) Family ALS, IGFBP-5, CTGF/CCN2, IGFBP-6, Cyr61/CCN1, IGFBP-L1, Endocan, IGFBP-rp1/ IGFBP-7, IGFBP-1, IGFBP-rP10, IGFBP-2, NOV/CCN3, IGFBP-3, WISP-1/CCN4, IGFBP-4; Receptor Tyrosine Kinases Ax1, FGF R4, C1q R1/CD93, FGF R5, DDR1, Flt-3, DDR2, HGF R, Dtk, IGF-I R, EGF, R IGF-II R, Eph, INSRR, EphA1, Insulin R/CD220, EphA2, M-CSF R, EphA3, Mer, EphA4, MSP R/Ron, EphA5, MuSK, EphA6, PDGF R alpha, EphA7, PDGF R beta, EphA8, Ret, EphB 1, RTK-like Orphan Receptor 1/ROR1, EphB2, RTK-like Orphan Receptor 2/ROR2, EphB3, SCF R/c-kit, EphB4, Tie-1, EphB6, Tie-2, ErbB2, TrkA, ErbB3, TrkB, ErbB4, TrkC, FGF, R1-4 VEGF R, FGF R1, VEGF R1/Flt-1, FGF R2, VEGF R2/KDR/Flk-1, FGF R3, VEGF R3/Flt-4; Proteoglycans & Regulators Proteoglycans Aggrecan, Mimecan, Agrin, NG2/MCSP, Biglycan, Osteoadherin, Decorin, Podocan, DSPG3, delta-Sarcoglycan, Endocan, Syndecan-1/CD138, Endoglycan, Syndecan-2, Endorepellin/Perlecan, Syndecan-3, Glypican 2, Syndecan-4, Glypican 3, Testican 1/SPOCK1, Glypican 5, Testican 2/SPOCK2, Glypican 6, Testican 3/SPOCK3, Lumican, Versican, Proteoglycan Regulators Arylsulfatase A/ARSA, Glucosamine (N-acetyl)-6-Sulfatase/GNS, Exostosin-like 2/EXTL2, HS6ST2, Exostosin-like 3/EXTL3, Iduronate 2-Sulfatase/IDS, GalNAc4S-6ST; SCF, Flt-3 Ligand & M-CSF Flt-3, M-CSF R, Flt-3 Ligand, SCF, M-CSF, SCF R/c-kit; TGF-beta Superfamily (same as listed for inflammatory markers); VEGF/PDGF Family Neuropilin-1, P1GF, Neuropilin-2, P1GF-2, PDGF, VEGF, PDGF R alpha, VEGF-B, PDGF R beta, VEGF-C, PDGF-A, VEGF-D, PDGF-AB, VEGF R, PDGF-B, VEGF R1/Flt-1, PDGF-C, VEGF R2/KDR/Flk-1, PDGF-D, VEGF R3/Flt-4; Wnt-related Molecules Dickkopf Proteins & Wnt InhibitorsDkk-1, Dkk-4, Dkk-2, Soggy-1, Dkk-3, WIF-1 Frizzled & Related Proteins Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP Wnt Ligands Wnt-1, Wnt-8a, Wnt-2b, Wnt-8b, Wnt-3a, Wnt-9a, Wnt-4, Wnt-9b, Wnt-5a, Wnt-10a, Wnt-5b, Wnt-10b, Wnt-7a, Wnt-11, Wnt-7b; Other Wnt-related Molecules APC, Kremen-2, Axin-1, LRP-1, beta-Catenin, LRP-6, Dishevelled-1, Norrin, Dishevelled-3, PKC beta 1, Glypican 3, Pygopus-1, Glypican 5, Pygopus-2, GSK-3 alpha/beta, R-Spondin 1, GSK-3 alpha, R-Spondin 2, GSK-3 beta, R-Spondin 3, ICAT, RTK-like Orphan Receptor 1/ROR1, Kremen-1, RTK-like Orphan Receptor 2/ROR, and Other Growth Factors CTGF/CCN2, beta-NGF, Cyr61/CCN1, Norrin, DANCE, NOV/CCN3, EG-VEGF/PK1, Osteocrin, Hepassocin, PD-ECGF, HGF, Progranulin, LECT2, Thrombopoietin, LEDGF, or WISP-1/CCN4.

In some embodiments, the antibody is specific to a marker that is a marker for cancer (oncology marker). In some embodiments, the antibody is specific to a marker that is a marker for cancer that is EGF. In some embodiments, the antibody is specific to a marker that is a marker for cancer that is TNF-alpha. In some embodiments, the antibody is specific to a marker that is a marker for cancer that is PSA. In some embodiments, the antibody is specific to a marker that is a marker for cancer that is VEGF. In some embodiments, the antibody is specific to a marker that is a marker for cancer that is TGF-beta. In some embodiments, the antibody is specific to a marker that is a marker for cancer that is FGFb. In some embodiments, the antibody is specific to a marker that is a marker for cancer that is TRAIL. In some embodiments, the antibody is specific to a marker that is a marker for cancer that is TNF-R1 (p55).

In further embodiments, the antibody is specific to a marker for cancer that is alpha-Fetoprotein. In some embodiments, the antibody is specific to a marker for cancer that is ER beta/? A2. In some embodiments, the antibody is specific to a marker for cancer that is ErbB2. In some embodiments, the antibody is specific to a marker for cancer that is Kallikrein 3/PSA. In some embodiments, the antibody is specific to a marker for cancer that is ER alpha/NR3A1. In some embodiments, the antibody is specific to a marker for cancer that is Progesterone R/NR3C3. In some embodiments, the antibody is specific to a marker for cancer that is A33. In some embodiments, the antibody is specific to a marker for cancer that is MIA. In some embodiments, the antibody is specific to a marker for cancer that is Aurora A. In some embodiments, the antibody is specific to a marker for cancer that is MMP-2. In some embodiments, the antibody is specific to a marker for cancer that is Bcl-2. In some embodiments, the antibody is specific to a marker for cancer that is MMP-3. In some embodiments, the antibody is specific to a marker for cancer that is Cadherin-13. In some embodiments, the antibody is specific to a marker for cancer that is MMP-9. In some embodiments, the antibody is specific to a marker for cancer that is E-Cadherin. In some embodiments, the antibody is specific to a marker for cancer that is NEK2. In some embodiments, the antibody is specific to a marker for cancer that is Carbonic Anhydrase IX. In some embodiments, the antibody is specific to a marker for cancer that is Nestin. In some embodiments, the antibody is specific to a marker for cancer that is beta-Catenin. In some embodiments, the antibody is specific to a marker for cancer that is NG2/MCSP. In some embodiments, the antibody is specific to a marker for cancer that is Cathepsin D. In some embodiments, the antibody is specific to a marker for cancer that is Osteopontin. In some embodiments, the antibody is specific to a marker for cancer that is CD44. In some embodiments, the antibody is specific to a marker for cancer that is p21/CIP1/CDKN1A. In some embodiments, the antibody is specific to a marker for cancer that is CEACAM-6. In some embodiments, the antibody is specific to a marker for cancer that is p27/Kip1. In some embodiments, the antibody is specific to a marker for cancer that is Cornulin. In some embodiments, the antibody is specific to a marker for cancer that is p53. In some embodiments, the antibody is specific to a marker for cancer that is DPPA4. In some embodiments, the antibody is specific to a marker for cancer that is Prolactin. In some embodiments, the antibody is specific to a marker for cancer that is ECM-1. In some embodiments, the antibody is specific to a marker for cancer that is PSP94. In some embodiments, the antibody is specific to a marker for cancer that is EGF. In some embodiments, the antibody is specific to a marker for cancer that is S100B. In some embodiments, the antibody is specific to a marker for cancer that is EGF R. In some embodiments, the antibody is specific to a marker for cancer that is S100P. In some embodiments, the antibody is specific to a marker for cancer that is EMMPRIN/CD147. In some embodiments, the antibody is specific to a marker for cancer that is SCF R/c-kit. In some embodiments, the antibody is specific to a marker for cancer that is Fibroblast Activation Protein alpha/FAP. In some embodiments, the antibody is specific to a marker for cancer that is Serpin E1/PAI-1. In some embodiments, the antibody is specific to a marker for cancer that is FGF acidic. In some embodiments, the antibody is specific to a marker for cancer that is Serum Amyloid A4. In some embodiments, the antibody is specific to a marker for cancer that is FGF basic. In some embodiments, the antibody is specific to a marker for cancer that is Survivin. In some embodiments, the antibody is specific to a marker for cancer that is Galectin-3. In some embodiments, the antibody is specific to a marker for cancer that is TEM8. In some embodiments, the antibody is specific to a marker for cancer that is Glypican 3. In some embodiments, the antibody is specific to a marker for cancer that is TIMP-1. In some embodiments, the antibody is specific to a marker for cancer that is HIN-1/Secretoglobulin 3A1. In some embodiments, the antibody is specific to a marker for cancer that is TIMP-2. In some embodiments, the antibody is specific to a marker for cancer that is IGF-1. In some embodiments, the antibody is specific to a marker for cancer that is TIMP-3. In some embodiments, the antibody is specific to a marker for cancer that is IGFBP-3. In some embodiments, the antibody is specific to a marker for cancer that is TIMP-4. In some embodiments, the antibody is specific to a marker for cancer that is IL-6. In some embodiments, the antibody is specific to a marker for cancer that is TNF-alpha/TNFSF1A. In some embodiments, the antibody is specific to a marker for cancer that is Kallikrein 6/Neurosin. In some embodiments, the antibody is specific to a marker for cancer that is TRAF-4. In some embodiments, the antibody is specific to a marker for cancer that is M-CSF. In some embodiments, the antibody is specific to a marker for cancer that is uPA. In some embodiments, the antibody is specific to a marker for cancer that is Matriptase/ST14. In some embodiments, the antibody is specific to a marker for cancer that is UPAR. In some embodiments, the antibody is specific to a marker for cancer that is Mesothelin. In some embodiments, the antibody is specific to a marker for cancer that is VCAM-1. In some embodiments, the antibody is specific to a marker for cancer that is Methionine Aminopeptidase. In some embodiments, the antibody is specific to a marker for cancer that is VEGF. In some embodiments, the antibody is specific to a marker for cancer that is Methionine Aminopeptidase 2.

In some embodiments, the antibody is specific to a marker that is a marker for inflammation. In some embodiments, the antibody is specific to a marker that is a marker for inflammation that is ICAM-1. In some embodiments, the antibody is specific to a marker that is a marker for inflammation that is RANTES. In some embodiments, the antibody is specific to a marker that is a marker for inflammation that is MIP-2. In some embodiments, the antibody is specific to a marker that is a marker for inflammation that is MIP-1 beta. In some embodiments, the antibody is specific to a marker that is a marker for inflammation that is MIP-1 alpha. In some embodiments, the antibody is specific to a marker that is a marker for inflammation that is MMP-3.

In some embodiments, the antibody is specific to a marker that is a marker for endocrine function. In some embodiments, the antibody is specific to a marker that is a marker for endocrine function that is 17 beta-estradiol (E2). In some embodiments, the antibody is specific to a marker that is a marker for endocrine function that is DHEA. In some embodiments, the antibody is specific to a marker that is a marker for endocrine function that is ACTH. In some embodiments, the antibody is specific to a marker that is a marker for endocrine function that is gastrin. In some embodiments, the antibody is specific to a marker that is a marker for endocrine function that is growth hormone.

In some embodiments, the antibody is specific to a marker that is a marker for autoimmune disease. In some embodiments, the antibody is specific to a marker that is a marker for autoimmune disease that is GM-CSF. In some embodiments, the antibody is specific to a marker that is a marker for autoimmune disease that is C-reactive protein (CRP). In some embodiments, the antibody is specific to a marker that is a marker for autoimmune disease that is G-CSF.

In some embodiments, the antibody is specific to a marker for thyroid function. In some embodiments, the antibody is specific to a marker for thyroid function that is cyclic AMP. In some embodiments, the antibody is specific to a marker for thyroid function. In some embodiments, the antibody is specific to a marker for thyroid function that is calcitonin. In some embodiments, the antibody is specific to a marker for thyroid function. In some embodiments, the antibody is specific to a marker for thyroid function that is parathyroid hormone.

In some embodiments, the antibody is specific to a marker for cardiovascular function. In some embodiments, the antibody is specific to a marker for cardiovascular function that is B-natruiretic peptide. In some embodiments, the antibody is specific to a marker for cardiovascular function that is NT-proBNP. In some embodiments, the antibody is specific to a marker for cardiovascular function that is C-reactive protein, HS. In some embodiments, the antibody is specific to a marker for cardiovascular function that is beta-thromboglobulin. In some embodiments, the antibody is specific to a marker for cardiovascular function that is a cardiac troponin. In some embodiments, the antibody is specific to a marker for cardiovascular function that is cardiac troponin I. In some embodiments, the antibody is specific to a marker for cardiovascular function that is cardiac troponin T.

In some embodiments, the antibody is specific to a marker for diabetes. In some embodiments, the antibody is specific to a marker for diabetes that is C-peptide. In some embodiments, the antibody is specific to a marker for diabetes that is leptin.

In some embodiments, the antibody is specific to a marker for infectious disease. In some embodiments, the antibody is specific to a marker for infectious disease that is IFN gamma. In some embodiments, the antibody is specific to a marker for infectious disease that is IFN alpha. In some embodiments, the antibody is specific to a marker for infectious disease that is TREM-1.

In some embodiments, the antibody is specific to a marker for metabolism. In some embodiments, the antibody is specific to a marker for metabolism that is bio-intact PTH (1-84). In some embodiments, the antibody is specific to a marker for metabolism that is PTH.

In some embodiments, the antibody is specific to a marker that is IL-1 beta. In some embodiments, the antibody is specific to a marker that is TNF-alpha. In some embodiments, the antibody is specific to a marker that is IL-6. In some embodiments, the antibody is specific to a marker that is TnI (cardiac troponin I). In some embodiments, the antibody is specific to a marker that is IL-8.

In some embodiments, the antibody is specific to a marker that is Abeta 40. In some embodiments, the antibody is specific to a marker that is Abeta 42. In some embodiments, the antibody is specific to a marker that is cAMP. In some embodiments, the antibody is specific to a marker that is FAS Ligand. In some embodiments, the antibody is specific to a marker that is FGF-basic. In some embodiments, the antibody is specific to a marker that is GM-CSF. In some embodiments, the antibody is specific to a marker that is IFN-alpha. In some embodiments, the antibody is specific to a marker that is IFN-gamma. In some embodiments, the antibody is specific to a marker that is IL-1a. In some embodiments, the antibody is specific to a marker that is IL-2. In some embodiments, the antibody is specific to a marker that is IL-4. In some embodiments, the antibody is specific to a marker that is IL-5. In some embodiments, the antibody is specific to a marker that is IL-7. In some embodiments, the antibody is specific to a marker that is IL-12. In some embodiments, the antibody is specific to a marker that is In some embodiments, the antibody is specific to a marker that is IL-13. In some embodiments, the antibody is specific to a marker that is IL-17. In some embodiments, the antibody is specific to a marker that is MCP-1. In some embodiments, the antibody is specific to a marker that is MIP-1a. In some embodiments, the antibody is specific to a marker that is RANTES. In some embodiments, the antibody is specific to a marker that is VEGF.

In some embodiments, the antibody is specific to a marker that is ACE. In some embodiments, the antibody is specific to a marker that is activin A. In some embodiments, the antibody is specific to a marker that is adiponectin. In some embodiments, the antibody is specific to a marker that is adipsin. In some embodiments, the antibody is specific to a marker that is AgRP. In some embodiments, the antibody is specific to a marker that is AKT1. In some embodiments, the antibody is specific to a marker that is albumin. In some embodiments, the antibody is specific to a marker that is betacellulin. In some embodiments, the antibody is specific to a marker that is bombesin. In some embodiments, the antibody is specific to a marker that is CD14. In some embodiments, the antibody is specific to a marker that is CD-26. In some embodiments, the antibody is specific to a marker that is CD-38. In some embodiments, the antibody is specific to a marker that is CD-40L. In some embodiments, the antibody is specific to a marker that is CD-40s. In some embodiments, the antibody is specific to a marker that is CDK5. In some embodiments, the antibody is specific to a marker that is Complement C3. In some embodiments, the antibody is specific to a marker that is Complement C4. In some embodiments, the antibody is specific to a marker that is C-peptide. In some embodiments, the antibody is specific to a marker that is CRP. In some embodiments, the antibody is specific to a marker that is EGF. In some embodiments, the antibody is specific to a marker that is E-selectin. In some embodiments, the antibody is specific to a marker that is FAS. In some embodiments, the antibody is specific to a marker that is FASLG. In some embodiments, the antibody is specific to a marker that is Fetuin A. In some embodiments, the antibody is specific to a marker that is fibrinogen. In some embodiments, the antibody is specific to a marker that is ghrelin. In some embodiments, the antibody is specific to a marker that is glucagon. In some embodiments, the antibody is specific to a marker that is growth hormone. In some embodiments, the antibody is specific to a marker that is haptoglobulin. In some embodiments, the antibody is specific to a marker that is hepatocyte growth factor. In some embodiments, the antibody is specific to a marker that is HGF. In some embodiments, the antibody is specific to a marker that is ICAM 1. In some embodiments, the antibody is specific to a marker that is IFNG. In some embodiments, the antibody is specific to a marker that is IGF1. In some embodiments, the antibody is specific to a marker that is IL-1RA. In some embodiments, the antibody is specific to a marker that is Il-6sr. In some embodiments, the antibody is specific to a marker that is IL-8. In some embodiments, the antibody is specific to a marker that is IL-1 0. In some embodiments, the antibody is specific to a marker that is IL-1 8. In some embodiments, the antibody is specific to a marker that is ILGFBP1. In some embodiments, the antibody is specific to a marker that is ILGFBP3. In some embodiments, the antibody is specific to a marker that is insulin-like growth factor 1. In some embodiments, the antibody is specific to a marker that is LEP. In some embodiments, the antibody is specific to a marker that is M-CSF. In some embodiments, the antibody is specific to a marker that is MMP2. In some embodiments, the antibody is specific to a marker that is MMP9. In some embodiments, the antibody is specific to a marker that is NGF. In some embodiments, the antibody is specific to a marker that is PAI-1. In some embodiments, the antibody is specific to a marker that is RAGE. In some embodiments, the antibody is specific to a marker that is RSP4. In some embodiments, the antibody is specific to a marker that is resistin. In some embodiments, the antibody is specific to a marker that is sex hormone binding globulin. In some embodiments, the antibody is specific to a marker that is SOCX3. In some embodiments, the antibody is specific to a marker that is TGF beta. In some embodiments, the antibody is specific to a marker that is thromboplastin. In some embodiments, the antibody is specific to a marker that is TNF R1. In some embodiments, the antibody is specific to a marker that is VCAM-1. In some embodiments, the antibody is specific to a marker that is VWF. In some embodiments, the antibody is specific to a marker that is TSH. In some embodiments, the antibody is specific to a marker that is EPITOME.

In some embodiments, the antibody is specific to a marker that is cardiac troponin I. In some embodiments, the antibody is specific to a marker that is TREM-1. In some embodiments, the antibody is specific to a marker that is IL-6. In some embodiments, the antibody is specific to a marker that is IL-8. In some embodiments, the antibody is specific to a marker that is Leukotriene T4. In some embodiments, the antibody is specific to a marker that is Akt1. In some embodiments, the antibody is specific to a marker that is TGF-beta. In some embodiments, the antibody is specific to a marker that is Fas ligand.

In some embodiments, the fluorescent moiety comprises a fluorescent molecule. In some embodiments, the fluorescent moiety comprises a plurality of fluorescent molecules, e.g., about 2-10, 2-8, 2-6, 2-4, 3-10, 3-8, or 3-6 fluorescent molecules. In some embodiments, the label comprises about 2-4 fluorescent molecules. In some embodiments, the fluorescent molecule comprises a molecule that comprises at least one substituted indolium ring system in which the substituent on the 3-carbon of the indolium ring contains a chemically reactive group or a conjugated substance. group. In some embodiments, the fluorescent molecules are selected from the group consisting of AlexaFluor 488, AlexaFluor 532, AlexaFluor 647, AlexaFluor 680 or AlexaFluor 700. In some embodiments, the fluorescent molecules are selected from the group consisting of AlexaFluor 488, AlexaFluor 532, AlexaFluor 680 or AlexaFluor 700. In some embodiments, the fluorescent molecules are AlexaFluor 647 molecules.

A. Binding Partners

Any suitable binding partner with the requisite specificity for the form of molecule, e.g., marker, to be detected may be used. If the molecule, e.g., marker, has several different forms, various specificities of binding partners are possible. Suitable binding partners are known in the art and include antibodies, aptamers, lectins, and receptors. A useful and versatile type of binding partner is an antibody.

1. Antibodies

Thus, in some embodiments, the binding partner is an antibody specific for a molecule to be detected. The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. It will be appreciated that the choice of epitope or region of the molecule to which the antibody is raised will determine its specificity, e.g., for various forms of the molecule, if present, or for total (e.g., all, or substantially all of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest, HyTest Ltd.,Turku Finland; Abcam Inc., Cambridge, Mass., USA, Life Diagnostics, Inc., West Chester, Pa., USA; Fitzgerald Industries International, Inc., Concord, Mass. 01742-3049 USA; BiosPacific, Emeryville, Calif.).

In some embodiments, the antibody is a polyclonal antibody. In other embodiments, the antibody is a monoclonal antibody.

Capture binding partners and detection binding partner pairs, e.g., capture and detection antibody pairs, may be used in embodiments of the invention. Thus, in some embodiments, a heterogeneous assay protocol is used in which, typically, two binding partners, e.g., two antibodies, are used. One binding partner is a capture partner, usually immobilized on a solid support, and the other binding partner is a detection binding partner, typically with a detectable label attached. Such antibody pairs are available from the sources described above, e.g., BiosPacific, Emeryville, Calif. Antibody pairs can also be designed and prepared by methods well-known in the art. Compositions of the invention include antibody pairs wherein one member of the antibody pair is a label as described herein, and the other member is a capture antibody.

In some embodiments it is useful to use an antibody that cross-reacts with a variety of species, either as a capture antibody, a detection antibody, or both. Such embodiments include the measurement of drug toxicity by determining, e.g., release of cardiac troponin into the blood as a marker of cardiac damage. A cross-reacting antibody allows studies of toxicity to be done in one species, e.g. a non-human species, and direct transfer of the results to studies or clinical observations of another species, e.g., humans, using the same antibody or antibody pair in the reagents of the assays, thus decreasing variability between assays. Thus, in some embodiments, one or more of the antibodies for use as a binding partner to the marker, e.g., cardiac troponin, such as cardiac troponin I, may be a cross-reacting antibody. In some embodiments, the antibody cross-reacts with the marker, e.g. cardiac troponin, from at least two species selected from the group consisting of human, monkey, dog, and mouse. In some embodiments the antibody cross-reacts with the marker e.g. cardiac troponin, from all of the group consisting of human, monkey, dog, and mouse.

B. Fluorescent Moieties

In some embodiments of labels used in the invention, the binding partner, e.g., antibody, is attached to a fluorescent moiety. The fluorescence of the moiety will be sufficient to allow detection in a single molecule detector, such as the single molecule detectors described herein.

A "fluorescent moiety," as that term is used herein, includes one or more fluorescent entities whose total fluorescence is such that the moiety may be detected in the single molecule detectors described herein. Thus, a fluorescent moiety may comprise a single entity (e.g., a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity may be attached to the binding partner separately or the entities may be attached together, as long as the entities as a group provide sufficient fluorescence to be detected.

Typically, the fluorescence of the moiety involves a combination of quantum efficiency and lack of photobleaching sufficient that the moiety is detectable above background levels in a single molecule detector, with the consistency necessary for the desired limit of detection, accuracy, and precision of the assay. For example, in some embodiments, the fluorescence of the fluorescent moiety is such that it allows detection and/or quantitation of a molecule, e.g., a marker, at a limit of detection of less than about 10, 5, 4, 3, 2, 1, 0.1, 0.01, 0.001, 0.00001, or 0.000001 pg/ml and with a coefficient of variation of less than about 20, 15, 14, 13, 12, 11, 10, 9, 8, 7, 6, 5, 4, 3, 2, 1% or less, e.g., about 10% or less, in the instruments described herein. In some embodiments, the fluorescence of the fluorescent moiety is such that it allows detection and/or quantitation of a molecule, e.g., a marker, at a limit of detection of less than about 5, 1, 0.5, 0.1, 0.05, 0.01, 0.005, 0.001 pg/ml and with a coefficient of variation of less than about 10%, in the instruments described herein.

"Limit of detection," as that term is used herein, includes the lowest concentration at which one can identify a sample as containing a molecule of the substance of interest, e.g., the first non-zero value. It can be defined by the variability of zeros and the slope of the standard curve. For example, the limit of detection of an assay may be determined by running a standard curve, determining the standard curve zero value, and adding 2 standard deviations to that value. A concentration of the substance of interest that produces a signal equal to this value is the "lower limit of detection" concentration.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay. In some embodiments, fluorescent moieties that are preferred are fluorescent moieties, e.g., dye molecules that have a combination of 1) high absorption coefficient; 2) high quantum yield; 3) high photostability (low photobleaching); and 4) compatibility with labeling the molecule of interest (e.g., protein) so that it may be analyzed using the analyzers and systems of the invention (e.g., does not cause precipitation of the protein of interest, or precipitation of a protein to which the moiety has been attached).

Fluorescent moieties, e.g., a single fluorescent dye molecule or a plurality of fluorescent dye molecules, that are useful in some embodiments of the invention may be defined in terms of their photon emission characteristics when stimulated by EM radiation. For example, in some embodiments, the invention utilizes a fluorescent moiety, e.g., a moiety comprising a single fluorescent dye molecule or a plurality of fluorescent dye molecules, that is capable of emitting an average of at least about 10, 20, 30, 40, 50, 75, 100, 125, 150, 175, 200, 225, 250, 275, 300, 350, 400, 500, 600, 700, 800, 900, or 1000, photons when simulated by a laser emitting light at the excitation wavelength of the moiety, where the laser is focused on a spot of not less than about 0.5 microns in diameter that contains the moiety, and where the total energy directed at the spot by the laser is no more than about 3 microJoules. It will be appreciated that the total energy may be achieved by many different combinations of power output of the laser and length of time of exposure of the dye moiety. E.g., a laser of a power output of 1 mW may be used for 3 ms, 3 mW for 1 ms, 6 mW for 0.5 ms, 12 mW for 0.25 ms, and so on.

In some embodiments, the invention utilizes a fluorescent dye moiety, e.g., a single fluorescent dye molecule or a plurality of fluorescent dye molecules, that is capable of emitting an average of at least about 50 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 100 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 150 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety, e.g., a single fluorescent dye molecule or a plurality of fluorescent dye molecules, that is capable of emitting an average of at least about 300 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. In some embodiments, the invention utilizes a fluorescent dye moiety e.g., a single fluorescent dye molecule or a plurality of fluorescent dye molecules, that is capable of emitting an average of at least about 500 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules.

In some embodiments, the fluorescent moiety comprises an average of at least about 1, 2, 3, 4, 5, 6, 7, 8, 9, or 10 fluorescent entities, e.g., fluorescent molecules. In some embodiments, the fluorescent moiety comprises an average of no more than about 2, 3, 4, 5, 6, 7, 8, 9, 10, or 11 fluorescent entities, e.g., fluorescent molecules. In some embodiments, the fluorescent moiety comprises an average of about 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 fluorescent entities. In some embodiments, the fluorescent moiety comprises an average of about 2 to 8 fluorescent moieties are attached. In some embodiments, an average of about 2 to 6 fluorescent entities. In some embodiments, the fluorescent moiety comprises an average of about 2 to 4 fluorescent entities. In some embodiments, the fluorescent moiety comprises an average of about 3 to 10 fluorescent entities. In some embodiments, the fluorescent moiety comprises an average of about 3 to 8 fluorescent entities. In some embodiments, the fluorescent moiety comprises an average of about 3 to 6 fluorescent entities. By "average" is meant that, in a given sample that is a representative sample of a group of labels of the invention, where the sample contains a plurality of the binding partner-fluorescent moiety units, the molar ratio of the particular fluorescent entity of which the fluorescent moiety is comprise, to the binding partner, as determined by standard analytical methods, corresponds to the number or range of numbers specified For example, in embodiments in which the label comprises a binding partner that is an antibody and a fluorescent moiety that comprises a plurality of fluorescent dye molecules of a specific absorbance, a spectrophometric assay may be used in which a solution of the label is diluted to an appropriate level and the absorbance at 280 nm is taken to determine the molarity of the protein (antibody) and an absorbance at, e.g., 650 nm (for AlexaFluor 647) is taken to determine the molarity of the fluorescent dye molecule. The ratio of the latter molarity to the former represents the average number of fluorescent entities (dye molecules) in the fluorescent moiety attached to each antibody.

1. Dyes

In some embodiments, the invention utilizes fluorescent moieties that comprise fluorescent dye molecules. In some embodiments, the invention utilizes a fluorescent dye molecule that is capable of emitting an average of at least about 50 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoule. In some embodiments, the invention utilizes a fluorescent dye molecule that is capable of emitting an average of at least about 75 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 100 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 150 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoules. In some embodiments, the invention utilizes a fluorescent dye molecule that is capable of emitting an average of at least about 200 photons when simulated by a laser emitting light at the excitation wavelength of the molecule, where the laser is focused on a spot of not less than about 5 microns in diameter that contains the molecule, and wherein the total energy directed at the spot by the laser is no more than about 3 microJoule A non-inclusive list of useful fluorescent entities for use in the fluorescent moieties of the invention is given in Table 2, below. In some embodiments, the fluorescent dye is selected from the group consisting of Alexa Flour 488, 532, 647, 700, 750, Fluorescein, B-phycoerythrin, allophycocyanin, PBXL-3, and Qdot 605. In some embodiments, the fluorescent dye is selected from the group consisting of Alexa Flour 488, 532, 700, 750, Fluorescein, B-phycoerythrin, allophycocyanin, PBXL-3, and Qdot 605.

TABLE 2

FLUORESCENT ENTITIES

| Dye | E Ex (nm) | E (M) − 1 | Em (nm) | MMw |
|---|---|---|---|---|
| Bimane | 380 | 5,700 | 458 | 282.31 |
| Dapoxyl | 373 | 22,000 | 551 | 362.83 |
| Dimethylamino coumarin-4-acetic acid | 375 | 22,000 | 470 | 344.32 |
| Marina blue | 365 | 19,000 | 460 | 367.26 |
| 8-Anilino naphthalene-1-sulfonic acid | 372 | | 480 | |
| Cascade blue | 376 | 23,000 | 420 | 607.42 |
| Alexa Fluor 405 | 402 | 35,000 | 421 | 1028.26 |
| Cascade blue | 400 | 29,000 | 420 | 607.42 |
| Cascade yellow | 402 | 24,000 | 545 | 563.54 |
| Pacific blue | 410 | 46,000 | 455 | 339.21 |
| PyMPO | 415 | 26,000 | 570 | 582.41 |
| Alexa 430 | 433 | 15,000 | 539 | 701.75 |
| Atto-425 | 438 | | 486 | |
| NBD | 465 | 22,000 | 535 | 391.34 |
| Alexa 488 | 495 | 73,000 | 519 | 643.41 |
| Fluorescein | 494 | 79,000 | 518 | 376.32 |
| Oregon Green 488 | 496 | 76,000 | 524 | 509.38 |
| Atto 495 | 495 | | 522 | |
| Cy2 | 489 | 150,000 | 506 | 713.78 |
| DY-480-XL | 500 | 40,000 | 630 | 514.60 |
| DY-485-XL | 485 | 20,000 | 560 | 502.59 |
| DY-490-XL | 486 | 27,000 | 532 | 536.58 |
| DY-500-XL | 505 | 90,000 | 555 | 596.68 |
| DY-520-XL | 520 | 40,000 | 664 | 514.60 |
| Alexa Fluor 532 | 531 | 81,000 | 554 | 723.77 |
| BODIPY 530/550 | 534 | 77,000 | 554 | 513.31 |
| 6-HEX | 535 | 98,000 | 556 | 680.07 |
| 6-JOE | 522 | 75,000 | 550 | 602.34 |
| Rhodamine 6G | 525 | 108,000 | 555 | 555.59 |
| Atto-520 | 520 | | 542 | |
| Cy3B | 558 | 130,000 | 572 | 658.00 |
| Alexa Fluor 610 | 612 | 138,000 | 628 | |
| Alexa Fluor 633 | 632 | 159,000 | 647 | ca. 1200 |
| Alexa Fluor 647 | 650 | 250,000 | 668 | ca. 1250 |
| BODIPY 630/650 | 625 | 101,000 | 640 | 660.50 |
| Cy5 | 649 | 250,000 | 670 | 791.99 |
| Alexa Fluor 660 | 663 | 110,000 | 690 | |
| Alexa Fluor 680 | 679 | 184,000 | 702 | |
| Alexa Fluor 700 | 702 | 192,000 | 723 | |
| Alexa Fluor 750 | 749 | 240,000 | 782 | |
| B-phycoerythrin | 546, 565 | 2,410,000 | 575 | 240,000 |
| R-phycoerythrin | 480, 546, 565 | 1,960,000 | 578 | 240,000 |
| Allophycocyanin | 650 | 700,000 | 660 | 700,000 |
| PBXL-1 | 545 | | 666 | |
| PBXL-3 | 614 | | 662 | |

Atto-tec dyes

| Name | Ex (nm) | Em (nm) | QY | □ (ns) |
|---|---|---|---|---|
| Atto 425 | 436 | 486 | 0.9 | 3.5 |
| Atto 495 | 495 | 522 | 0.45 | 2.4 |
| Atto 520 | 520 | 542 | 0.9 | 3.6 |
| Atto 560 | 561 | 585 | 0.92 | 3.4 |
| Atto 590 | 598 | 634 | 0.8 | 3.7 |
| Atto 610 | 605 | 630 | 0.7 | 3.3 |
| Atto 655 | 665 | 690 | 0.3 | 1.9 |
| Atto 680 | 680 | 702 | 0.3 | 1.8 |

Dyomics Fluors

| label | Ex (nm) | Molar absorbance* [l · mol − 1 · cm − 1] | Em (nm) | molecular weight# [g · mol − 1] |
|---|---|---|---|---|
| DY-495/5 | 495 | 70,000 | 520 | 489.47 |
| DY-495/6 | 495 | 70,000 | 520 | 489.47 |
| DY-495X/5 | 495 | 70,000 | 520 | 525.95 |
| DY-495X/6 | 495 | 70,000 | 520 | 525.95 |
| DY-505/5 | 505 | 85,000 | 530 | 485.49 |
| DY-505/6 | 505 | 85,000 | 530 | 485.49 |
| DY-505X/5 | 505 | 85,000 | 530 | 523.97 |
| DY-505X/6 | 505 | 85,000 | 530 | 523.97 |
| DY-550 | 553 | 122,000 | 578 | 667.76 |
| DY-555 | 555 | 100.000 | 580 | 636.18 |
| DY-610 | 609 | 81.000 | 629 | 667.75 |
| DY-615 | 621 | 200.000 | 641 | 578.73 |
| DY-630 | 636 | 200.000 | 657 | 634.84 |
| DY-631 | 637 | 185.000 | 658 | 736.88 |
| DY-633 | 637 | 180.000 | 657 | 751.92 |
| DY-635 | 647 | 175.000 | 671 | 658.86 |
| DY-636 | 645 | 190.000 | 671 | 760.91 |
| DY-650 | 653 | 170.000 | 674 | 686.92 |
| DY-651 | 653 | 160.000 | 678 | 888.96 |
| DYQ-660 | 660 | 117,000 | — | 668.86 |
| DYQ-661 | 661 | 116,000 | — | 770.90 |
| DY-675 | 674 | 110.000 | 699 | 706.91 |
| DY-676 | 674 | 145.000 | 699 | 807.95 |
| DY-680 | 690 | 125.000 | 709 | 634.84 |
| DY-681 | 691 | 125.000 | 708 | 736.88 |
| DY-700 | 702 | 96.000 | 723 | 668.86 |
| DY-701 | 706 | 115.000 | 731 | 770.90 |
| DY-730 | 734 | 185.000 | 750 | 660.88 |
| DY-731 | 736 | 225.000 | 759 | 762.92 |
| DY-750 | 747 | 240.000 | 776 | 712.96 |
| DY-751 | 751 | 220.000 | 779 | 814.99 |
| DY-776 | 771 | 147.000 | 801 | 834.98 |
| DY-780-OH | 770 | 70.000 | 810 | 757.34 |
| DY-780-P | 770 | 70.000 | 810 | 957.55 |
| DY-781 | 783 | 98.000 | 800 | 762.92 |
| DY-782 | 782 | 102.000 | 800 | 660.88 |
| EVOblue-10 | 651 | 101.440 | 664 | 389.88 |
| EVOblue-30 | 652 | 102.000 | 672 | 447.51 |

Quantum Dots: Qdot 525, 565, 585, 605, 655, 705, 800

Suitable dyes for use in the invention include modified carbocyanine dyes. The modification of carbocyanine dyes includes the modification of an indolium ring of the carbocyanine dye to permit a reactive group or conjugated substance at the number 3 position. The modification of the indolium ring provides dye conjugates that are uniformly and substantially more fluorescent on proteins, nucleic acids and other biopolymers, than conjugates labeled with structurally similar carbocyanine dyes bound through the nitrogen atom at the number one position. In addition to having more intense fluorescence emission than structurally similar dyes at virtually identical wavelengths, and decreased artifacts in their absorption spectra upon conjugation to biopolymers, the modified carbocyanine dyes have greater photostability and higher absorbance (extinction coefficients) at the wavelengths of peak absorbance than the structurally similar dyes. Thus, the modified carbocyanine dyes result in greater sensitivity in assays that use the modified dyes and their conjugates. Preferred modified dyes include compounds that have at least one substituted indolium ring system in which the substituent on the 3-carbon of the indolium ring contains a chemically reactive group or a conjugated substance. Other dye compounds include compounds that incorporate an azabenzazolium ring moiety and at least one sulfonate moiety. The modified carbocyanine dyes that can be used to detect individual molecules in various embodiments of the invention are described in U.S. Pat. No. 6,977,305, which is herein incorporated by reference in its entirety. Thus, in some embodiments the labels of the invention utilize a fluorescent dye that includes a substituted indolium ring system in which the substituent on the 3-carbon of the indolium ring contains a chemically reactive group or a conjugated substance group.

In some embodiments, the label comprises a fluorescent moiety that includes one or more Alexa dyes (Molecular Probes, Eugene, Oreg.). The Alexa dyes are disclosed in U.S. Pat. Nos. 6,977,305; 6,974,874; 6,130,101; and 6,974,305 which are herein incorporated by reference in their entirety. Some embodiments of the invention utilize a dye chosen from the group consisting of AlexaFluor 647, AlexaFluor 488, AlexaFluor 532, AlexaFluor 555, AlexaFluor 610, AlexaFluor 680, AlexaFluor 700, and AlexaFluor 750. Some embodiments of the invention utilize a dye chosen from the group consisting of AlexaFluor 488, AlexaFluor 532, AlexaFluor 647, AlexaFluor 700 and AlexaFluor 750. Some embodiments of the invention utilize a dye chosen from the group consisting of AlexaFluor 488, AlexaFluor 532, AlexaFluor 555, AlexaFluor 610, AlexaFluor 680, AlexaFluor 700, and AlexaFluor 750. Some embodiments of the invention utilize the AlexaFluor 647 molecule, which has an absorption maximum between about 650 and 660 nm and an emission maximum between about 660 and 670 nm. The AlexaFluor 647 dye is used alone or in combination with other AlexaFluor dyes.

In addition, currently available organic fluors can be improved by rendering them less hydrophobic by adding hydrophilic groups such as polyethylene. Alternatively, currently sulfonated organic fluors such as the AlexaFluor 647 dye can be rendered less acidic by making them zwitterionic. Particles such as antibodies that are labeled with the modified fluors are less likely to bind non-specifically to surfaces and proteins in immunoassays, and thus enable assays that have greater sensitivity and lower backgrounds. Methods for modifying and improving the properties of fluorescent dyes for the purpose of increasing the sensitivity of a system that detects single particles are known in the art. Preferably, the modification improves the Stokes shift while maintaining a high quantum yield.

2. Quantum Dots

In some embodiments, the fluorescent label moiety that is used to detect a molecule in a sample using the analyzer systems of the invention is a quantum dot. Quantum dots (QDs), also known as semiconductor nanocrystals or artificial atoms, are semiconductor crystals that contain anywhere between 100 to 1,000 electrons and range from 2-10 nm. Some QDs can be between 10-20 nm in diameter. QDs have high quantum yields, which makes them particularly useful for optical applications. QDs are fluorophores that fluoresce by forming excitons, which can be thought of the excited state of traditional fluorophores, but have much longer lifetimes of up to 200 nanoseconds. This property provides QDs with low photobleaching. The energy level of QDs can be controlled by changing the size and shape of the QD, and the depth of the QDs' potential. One of the optical features of small excitonic QDs is coloration, which is determined by the size of the dot. The larger the dot, the redder, or more towards the red end of the spectrum the fluorescence. The smaller the dot, the bluer or more towards the blue end it is. The bandgap energy that determines the energy and hence the color of the fluoresced light is inversely proportional to the square of the size of the QD. Larger QDs have more energy levels which are more closely spaced, thus allowing the QD to absorb photons containing less energy, i.e. those closer to the red end of the spectrum. Because the emission frequency of a dots dependent on the bandgap, it is therefore possible to control the output wavelength of a dot with extreme precision. In some embodiments the protein that is detected with the single particle analyzer system is labeled with a QD. In some embodiments, the single particle analyzer is used to detect a protein labeled with one QD and using a filter to allow for the detection of different proteins at different wavelengths. QDs have broad excitation and narrow emission properties which when used with color filtering require only a single electromagnetic source for multiplex analysis of multiple targets in a single sample to resolve individual signals. Thus, in some embodiments, the analyzer system comprises one continuous wave laser and particles that are each labeled with one QD. Colloidally prepared QDs are free floating and can be attached to a variety of molecules via metal coordinating functional groups. These groups include but are not limited to thiol, amine, nitrile, phosphine, phosphine oxide, phosphonic acid, carboxylic acids or other ligands. By bonding appropriate molecules to the surface, the quantum dots can be dispersed or dissolved in nearly any solvent or incorporated into a variety of inorganic and organic films. Quantum dots (QDs) can be coupled to streptavidin directly through a maleimide ester coupling reaction or to antibodies through a maleimide-thiol coupling reaction. This yields a material with a biomolecule covalently attached on the surface, which produces conjugates with high specific activity. In some embodiments, the protein that is detected with the single particle analyzer is labeled with one quantum dot. In some embodiments the quantum dot is between 10 and 20 nm in diameter. In other embodiments, the quantum dot is between 2 and 10 nm in diameter. Useful Quantum Dots include QD 605, QD 610, QD 655, and QD 705. A particularly preferred Quantum Dot is QD 605.

C. Binding Partner-Fluorescent Moiety Compositions

The labels of the invention generally contain a binding partner, e.g., antibody, bound to a fluorescent moiety to provide the requisite fluorescence for detection and quantitation in the instruments described herein. Any suitable combination of binding partner and fluorescent moiety for detection in the single molecule detectors described herein may be used as a label in the invention. In some embodiments, the invention provides a label for a marker of a biological state, where the label includes an antibody to the marker and a fluorescent moiety. The marker may be any of the markers described above. The antibody may be any antibody as described above. A fluorescent moiety may be attached such that the label is capable of emitting an average of at least about 50, 75, 100, 125, 150, 175, 200, 225, 250, 275, 300, 350, 400, 500, 600, 700, 800, 900, or 1000, photons when simulated by a laser emitting light at the excitation wavelength of the moiety, where the laser is focused on a spot of not less than about 5 microns in diameter that contains the label, and wherein the total energy directed at the spot by the laser is no more than about 3 microJoules. In some embodiments, the fluorescent moiety may be a fluorescent moiety that is capable of emitting an average of at least about 50, 100, 150, or 200 photons when simulated by a laser emitting light at the excitation wavelength of the moiety, where the laser is focused on a spot of not less than about 5 microns in diameter that contains the moiety, and wherein the total energy directed at the spot by the laser is no more than about 3 microJoules. The fluorescent moiety may be a fluorescent moiety that includes one or more dye molecules with a structure that includes a substituted indolium ring system in which the substituent on the 3-carbon of the indolium ring contains a chemically reactive group or a conjugated substance group. The label composition may include a fluorescent moiety that includes one or more dye molecules selected from the group consisting of AlexaFluor 488, 532, 647, 700, or 750. The label composition may include a fluorescent moiety that includes one or more dye molecules selected from the group consisting of AlexaFluor 488, 532, 700, or 750. The label composition may include a fluorescent moiety that includes one or more dye molecules that are AlexaFluor 488. The label composition may include a fluorescent moiety that includes one or more dye molecules that are AlexaFluor 555. The label composition may include a fluorescent moiety that includes one or more dye molecules that are AlexaFluor 610. The label composition may include a fluorescent moiety that includes one or more dye molecules that are AlexaFluor 647. The label composition may include a fluorescent moiety that includes one or more dye molecules that are AlexaFluor 680. The label composition may include a fluorescent moiety that includes one or more dye molecules that are AlexaFluor 700. The label composition may include a fluorescent moiety that includes one or more dye molecules that are AlexaFluor 750.

In some embodiments the invention provides a composition for the detection of a marker of a biological state that includes an AlexFluor molecule, e.g. an AlexaFluor molecule selected from the described groups, such as an AlexaFluor 647 molecule attached to a to an antibody specific for the marker. In some embodiments the composition includes an average of 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 AlexaFluor 647 molecules molecule attached to an antibody for the marker. In some embodiments the invention provides a composition for the detection a marker of a biological state that includes an average of 1 to 11, or about 2 to 10, or about 2 to 8, or about 2 to 6, or about 2 to 5, or about 2 to 4, or about 3 to 10, or about 3 to 8, or about 3 to 6, or about 3 to 5, or about 4 to 10, or about 4 to 8, or about 4 to 6, or about 2, 3, 4, 5, 6, or more than about 6 AlexaFluor 647 molecules molecule attached to an antibody specific to the marker. In some embodiments the invention provides a composition for the detection of a marker of a biological state that includes an average of about 2 to 10 AlexaFluor 647 molecules molecule attached to an antibody specific to the marker. In some embodiments the invention provides a composition for the detection of a marker of a biological state that includes an average of about 2 to 8 AlexaFluor 647 molecules molecule attached to an antibody specific to the marker. In some embodiments the invention provides a composition for the detection of a marker of a biological state that includes an average of about 2 to 6 AlexaFluor 647 molecules molecule attached to an antibody specific to the marker. In some embodiments the invention provides a composition for the detection of a marker of a biological state that includes an average of about 2 to 4 AlexaFluor 647 molecules molecule attached to an antibody specific to the marker. In some embodiments the invention provides a composition for the detection of a marker of a biological state that includes an average of about 3 to 8 AlexaFluor 647 molecules molecule attached to an antibody specific to the marker. In some embodiments the invention provides a composition for the detection of a marker of a biological state that includes an average of about 3 to 6 AlexaFluor 647 molecules molecule attached to an antibody specific to the marker. In some embodiments the invention provides a composition for the detection of a marker of a biological state that includes an average of about 4 to 8 AlexaFluor 647 molecules molecule attached to an antibody specific to the marker.

Attachment of the fluorescent moiety, or fluorescent entities that make up the fluorescent moiety, to the binding partner, e.g., antibody, may be by any suitable means; such methods are well-known in the art and exemplary methods are given in the Examples. In some embodiments, after attachment of the fluorescent moiety to the binding partner to form a label for use in the methods of the invention, and prior to the use of the label for labeling the protein of interest, it is useful to perform a filtration step. E.g., an antibody-dye label may be filtered prior to use, e.g., through a 0.2 micron filter, or any suitable filter for removing aggregates. Other reagents for use in the assays of the invention may also be filtered, e.g., e.g., through a 0.2 micron filter, or any suitable filter. Without being bound by theory, it is thought that such filtration removes a portion of the aggregates of the, e.g., antibody-dye labels. As such aggregates will bind as a unit to the protein of interest, but upon release in elution buffer are likely to disaggregate, false positives may result; i.e., several labels will be detected from an aggregate that has bound to only a single protein molecule of interest. Regardless of theory, filtration has been found to reduce false positives in the subsequent assay and to improve accuracy and precision.

It will be appreciated that immunoassays often employ a sandwich format, in which binding partner pairs, e.g. antibodies, to the same molecule, e.g., marker are used. The invention also encompasses binding partner pairs, e.g., antibodies, wherein both antibodies are specific to the same molecule, e.g., the same marker, and wherein at least one member of the pair is a label as described herein. Thus, for any label that includes a binding-partner and a fluorescent moiety, the invention also encompasses a pair of binding partners wherein the first binding partner, e.g., antibody, is part of the label, and the second binding partner, e.g., antibody, is, typically, unlabeled and serves as a capture binding partner. In addition, binding partner pairs are frequently used in FRET assays. FRET assays useful in the invention are disclosed in U.S. patent application Ser. No. 11/048,660, incorporated by reference herein in its entirety, and the present invention also encompasses binding partner pairs, each of which includes a FRET label.

IV. Highly Sensitive Analysis of Molecules

In one aspect, the invention provides a method for determining the presence or absence of a single molecule, e.g., a molecule of a marker of a biological state, in a sample, by i) labeling the molecule if present, with a label; and ii) detecting the presence or absence of the label, where the detection of the presence of the label indicates the presence of the single molecule in the sample. In some embodiments, the method is capable of detecting the molecule at a limit of detection of less than about 100, 80, 60, 50, 40, 30, 20, 15, 12, 10, 9, 8, 7, 6, 5, 4, 3, 2, 1, 0.9, 0.8, 0.7, 0.6, 0.5, 0.4, 0.3, 0.2. 0.1, 0.05, 0.01, 0.005, or 0.001 femtomolar. In some embodiments, the method is capable of detecting the molecule at a limit of detection of less than about 100 femtomolar. In some embodiments, the method is capable of detecting the molecule at a limit of detection of less than about 10 femtomolar. In some embodiments, the method is capable of detecting the molecule at a limit of detection of less than about 1 femtomolar. In some embodiments, the method is capable of detecting the molecule at a limit of detection of less than about 0.1 femtomolar. In some embodiments, the method is capable of detecting the molecule at a limit of detection of less than about 0.01 femtomolar. In some embodiments, the method is capable of detecting the molecule at a limit of detection of less than about 0.001 femtomolar. Detection limits may be determined by use of an appropriate standard, e.g., National Institute of Standards and Technology reference standard material.

The methods also provide methods of determining a concentration of a molecule, e.g., a marker of a biological state, in a sample by detecting single molecules of the molecule in the sample. The "detecting" of a single molecule includes detecting the molecule directly or indirectly. In the case of indirect detection, labels that corresponds to single molecules, e.g., a labels that have been attached to the single molecules, may be detected.

In some embodiments, the invention provides a method for determining the presence or absence of a single molecule of a protein in a biological sample, comprising labeling said molecule with a label and detecting the presence or absence of said label in a single molecule detector, wherein said label comprises a fluorescent moiety that is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. The single molecule detector may, in some embodiments, comprise not more than one interrogation space. The limit of detection of the single molecule in the sample may be less than about 10, 1, 0.1, 0.01, or 0.001 femtomolar. In some embodiments, the limit of detection is less than about 1 femtomolar. The detecting may comprise detecting electromagnetic radiation emitted by said fluorescent moiety. The method may further comprise exposing said fluorescent moiety to electromagnetic radiation, e.g., electromagnetic radiation provided by a laser, such as a laser with a power output of about 2, 3, 4, 5, 6, 7, 8, 9, 10, 11, 12, 13, 14, 15, 16, 17, 18, 19, 20 mW. In some embodiments, the laser stimulates provides light to the interrogation space for a duration of about 10-1000 microseconds, or about 1000, 250, 100, 50, 25 or 10 microseconds. In some embodiments, the label further comprises a binding partner specific for binding said molecule, such as an antibody. In some embodiments, the fluorescent moiety comprises a fluorescent dye molecule, such as a dye molecule that comprises at least one substituted indolium ring system in which the substituent on the 3-carbon of the indolium ring contains a chemically reactive group or a conjugated substance. In some embodiments, the dye molecule is an AlexFluor molecule selected from the group consisting of AlexaFluor 488, AlexaFluor 532, AlexaFluor 647, AlexaFluor 680 or AlexaFluor 700. In some embodiments, the dye molecule is an AlexaFluor647 dye molecule. In some embodiments, the fluorescent moiety comprises a plurality of AlexaFluor 647 molecules. In some embodiments, the plurality of AlexaFluor 647 molecules comprises about 2-4 AlexaFluor 647 molecules, or about 3-6 AlexaFluor 647 molecules. In some embodiments, the fluorescent moiety is a quantum dot. The method may further comprise measuring the concentration of said protein in the sample.

In some embodiments, detecting the presence or absence of said label comprises: (i) passing a portion of said sample through an interrogation space; (ii) subjecting said interrogation space to exposure to electromagnetic radiation, said electromagnetic radiation being sufficient to stimulate said fluorescent moiety to emit photons, if said label is present; and (iii) detecting photons emitted during said exposure of step (ii). The method may further comprise determining a background photon level in said interrogation space, wherein said background level represents the average photon emission of the interrogation space when it is subjected to electromagnetic radiation in the same manner as in step (ii), but without label in the interrogation space. The method may further comprise comparing the amount of photons detected in step (iii) to a threshold photon level, wherein said threshold photon level is a function of said background photon level, wherein an amount of photons detected in step (iii) greater that the threshold level indicates the presence of said label, and an amount of photons detected in step (iii) equal to or less than the threshold level indicates the absence of said label.

A. Sample

The sample may be any suitable sample. Typically, the sample is a biological sample, e.g., a biological fluid. Such fluids include, without limitation, bronchoalveolar lavage fluid (BAL), blood, serum, plasma, urine, nasal swab, cerebrospinal fluid, pleural fluid, synovial fluid, peritoneal fluid, amniotic fluid, gastric fluid, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the target particle of interest. Other similar specimens such as cell or tissue culture or culture broth are also of interest. In some embodiments, the sample is a blood sample. In some embodiments the sample is a plasma sample. In some embodiments the sample is a serum sample. In some embodiments, the sample is a urine sample. In some embodiments, the sample is a nasal swab.

B. Sample Preparation

In general, any method of sample preparation may be used that produces a label corresponding to a molecule of interest, e.g., a marker of a biological state, that is wished to be measured, where the label is detectable in the instruments described herein. As is known in the art, sample preparation in which a label is added to one or more molecules may be performed in a homogeneous or heterogeneous format. In some embodiments, the sample preparation is formed in a homogenous format. In analyzer system employing a homogenous format, unbound label is not removed from the sample. See, e.g., U.S. patent application Ser. No. 11/048,660. In some embodiments, the particle or particles of interest are labeled by addition of labeled antibody or antibodies that bind to the particle or particles of interest.

In some embodiments, a heterogeneous assay format is used, where, typically, a step is employed for removing unbound label. Such assay formats are well-known in the art. One particularly useful assay format is a sandwich assay, e.g., a sandwich immunoassay. In this format, the molecule of interest, e.g., marker of a biological state, is captured, e.g., on a solid support, using a capture binding partner. Unwanted molecules and other substances may then optionally be washed away, followed by binding of a label comprising a detection binding partner and a detectable label, e.g., fluorescent moiety. Further washes remove unbound label, then the detectable label is released, usually though not necessarily still attached to the detection binding partner. In alternative embodiments, sample and label are added to the capture binding partner without a wash in between, e.g., at the same time. Other variations will be apparent to one of skill in the art.

In some embodiments, the method for detecting the molecule of interest, e.g., marker of a biological state, uses a sandwich assay with antibodies, e.g., monoclonal antibodies as capture binding partners. The method comprises binding molecules in a sample to a capture antibody that is immobilized on a binding surface, and binding the label comprising a detection antibody to the molecule to form a "sandwich" complex. The label comprises the detection antibody and a fluorescent moiety, as described herein, which is detected, e.g., using the single molecule analyzers of the invention. Both the capture and detection antibodies specifically bind the molecule. Many example of sandwich immunoassays are known, and some are described in U.S. Pat. No. 4,168,146 to Grubb et al. and U.S. Pat. No. 4,366,241 to Tom et al., both of which are incorporated herein by reference. Further examples specific to specific markers are described in the Examples.

The capture binding partner may be attached to a solid support, e.g., a microtiter plate or paramagnetic beads. In some embodiments, the invention provides a binding partner for a molecule of interest, e.g., marker of a biological state, attached to a paramagnetic bead. Any suitable binding partner that is specific for the molecule that it is wished to capture may be used. The binding partner may be an antibody, e.g., a monoclonal antibody. Production and sources of antibodies are described elsewhere herein. It will be appreciated that antibodies identified herein as useful as a capture antibody may also be useful as detection antibodies, and vice versa.

The attachment of the binding partner, e.g., antibody, to the solid support may be covalent or noncovalent. In some embodiments, the attachment is noncovalent. An example of a noncovalent attachment well-known in the art is biotin-avidin/streptavidin interactions. Thus, in some embodiments, a solid support, e.g., a microtiter plate or a paramagnetic bead, is attached to the capture binding partner, e.g., antibody, through noncovalent attachment, e.g., biotin-avidin/streptavidin interactions. In some embodiments, the attachment is covalent. Thus, in some embodiments, a solid support, e.g., a microtiter plate or a paramagnetic bead, is attached to the capture binding partner, e.g., antibody, through covalent attachment.

Covalent attachment in which the orientation of the capture antibody is such that capture of the molecule of interest is optimized is especially useful. For example, in some embodiments a solid support, e.g., a microtiter plate or a paramagnetic microparticle, may be used in which the attachment of the binding partner, e.g., antibody, is an oriented attachment, e.g., a covalent oriented attachment.

An exemplary protocol for oriented attachment of an antibody to a solid support is as follows: IgG is dissolved in 0.1M sodium acetate buffer, pH 5.5 to a final concentration of 1 mg/ml. An equal volume of ice-cold 20 mM sodium periodate in 0.1 M sodium acetate, pH 5.5 is added. The IgG is allowed to oxidize for ½ hour on ice. Excess periodate reagent is quenched by the addition of 0.15 volume of 1 M glycerol. Low molecular weight byproducts of the oxidation reaction are removed by ultrafiltration. The oxidized IgG fraction is diluted to a suitable concentration (typically 0.5 micrograms IgG per ml) and reacted with hydrazide-activated multiwell plates for at least two hours at room temperature. Unbound IgG is removed by washing the multiwell plate with borate buffered saline or another suitable buffer. The plate may be dried for storage, if desired. A similar protocol may be followed for microbeads if the material of the microbead is suitable for such attachment.

In some embodiments, the solid support is a microtiter plate. In some embodiments, the solid support is a paramagnetic bead. An exemplary paramagnetic bead is Streptavidin C1(Dynal, 650.01-03). Other suitable beads will be apparent to those of skill in the art. Methods for attachment of antibodies to paramagnetic beads are well-known in the art. One example is given in Example 2.

The molecule of interest is contacted with the capture binding partner, e.g., capture antibody immobilized on a solid support. Some sample preparation may be used; e.g., preparation of serum from blood samples or concentration procedures before the sample is contacted with the capture antibody. Protocols for binding of proteins in immunoassays are well-known in the art and are included in the Examples.

The time allowed for binding will vary depending on the conditions; it will be apparent that shorter binding times are desirable in some settings, especially in a clinical setting. The use of, e.g., paramagnetic beads can reduce the time required for binding. In some embodiments, the time allowed for binding of the molecule of interest to the capture binding partner, e.g., antibody, is less that about 12, 10, 8, 6, 4, 3, 2, or 1 hours, or less than about 60, 50, 40, 30, 25, 20, 15, 10, or 5 minutes.

In some embodiments, the time allowed for binding of the molecule of interest to the capture binding partner, e.g., antibody, is less than about 60 minutes. In some embodiments, the time allowed for binding of the molecule of interest to the capture binding partner, e.g., antibody, is less that about 40 minutes. In some embodiments, the time allowed for binding of the molecule of interest to the capture binding partner, e.g., antibody, is less that about 30 minutes. In some embodiments, the time allowed for binding of the molecule of interest to the capture binding partner, e.g., antibody, is less that about 20 minutes. In some embodiments, the time allowed for binding of the molecule of interest to the capture binding partner, e.g., antibody, is less that about 15 minutes. In some embodiments, the time allowed for binding of the molecule of interest to the capture binding partner, e.g., antibody, is less that about 10 minutes. In some embodiments, the time allowed for binding of the molecule of interest to the capture binding partner, e.g., antibody, is less that about 5 minutes.

In some embodiments, following the binding of the troponin particles to the capture binding partner, e.g., capture antibody, particles that may have bound nonspecifically, as well as other unwanted substances in the sample, are washed away leaving substantially only specifically bound troponin particles. In other embodiments, no wash is used between additions of sample and label; it will be appreciated that this reduces sample preparation time even further. Thus, in some embodiments, the time allowed for both binding of the molecule of interest to the capture binding partner, e.g., antibody, and binding of the label to the molecule of interest, is less that about 12, 10, 8, 6, 4, 3, 2, or 1 hours, or less than about 60, 50, 40, 30, 25, 20, 15, 10, or 5 minutes. In some embodiments, the time allowed for both binding of the molecule of interest to the capture binding partner, e.g., antibody, and binding of the label to the molecule of interest, is less that about 60 minutes. In some embodiments, the time allowed for both binding of the molecule of interest to the capture binding partner, e.g., antibody, and binding of the label to the molecule of interest, is less than about 40 minutes. In some embodiments, the time allowed for both binding of the molecule of interest to the capture binding partner, e.g., antibody, and binding of the label to the molecule of interest, is less than about 30 minutes. In some embodiments, the time allowed for both binding of the molecule of interest to the capture binding partner, e.g., antibody, and binding of the label to the molecule of interest, is less than about 20 minutes. In some embodiments, the time allowed for both binding of the molecule of interest to the capture binding partner, e.g., antibody, and binding of the label to the molecule of interest, is less than about 15 minutes. In some embodiments, the time allowed for both binding of the molecule of interest to the capture binding partner, e.g., antibody, and binding of the label to the molecule of interest, is less than about 10 minutes. In some embodiments, the time allowed for both binding of the molecule of interest to the capture binding partner, e.g., antibody, and binding of the label to the molecule of interest, is less than about 5 minutes.

Some immunoassay diagnostic reagents including the capture and signal antibodies used to measure the molecule of interest may be derived from the sera of animals. Endogenous human heterophilic antibodies, or human anti-animal antibodies, which have the ability to bind to immunoglobulins of other species, are present in the serum or plasma of more than 10% of patients. These circulating heterophile antibodies may interfere with immunoassay measurements. In sandwich immunoassays, these heterophilic antibodies can either bridge the capture and detection (diagnostic) antibodies, thereby producing a false-positive signal, or they may block the binding of the diagnostic antibodies, thereby producing a false-negative signal. In competitive immunoassays, the heterophile antibodies may bind to the analytic antibody and inhibit its binding to the troponin. They also may either block or augment the separation of the antibody-troponin complex from free troponin, especially when antispecies antibodies are used in the separation systems. Therefore, the impact of these heterophile antibody interferences are difficult to predict. Thus, it would be advantageous to block the binding of any heterophilic antibodies. In some embodiments of the invention, the immunoassay includes the step of depleting the sample of heterophile antibodies using one or more heterophile antibody blockers. Methods for removing heterophile antibodies from samples that are to be tested in immunoassays are known and include: heating the specimen in a sodium acetate buffer, pH 5.0, for 15 minutes at 90° C. and centrifuging at 1200 g for 10 minutes, or the heterophile antibodies can be precipitated using polyethylene glycol (PEG); immunoextracting the interfering heterophile immunoglobulins from the specimen using protein A or protein G; or adding nonimmune mouse IgG. Embodiments of the methods of the invention contemplate preparing the sample prior to analysis with the single molecule detector. The appropriateness of the method of pretreatment may be determined. Biochemicals to minimize immunoassay interference caused by heterophile antibodies are commercially available. For example, a product called MAK33, which is an IgG1 monoclonal antibody to h-CK-MM, may be obtained from Boehringer Mannheim. The MAK33 plus product contains a combination of IgG1 and IgG1-Fab. The polyMAK33 contains IgG1-Fab polymerized with IgG1, and the polyMAC 2b/2a contains IgG2a-Fab polymerized with IgG2b. A second commercial source of biochemicals to neutralize heterophile antibodies is Immunoglobulin Inhibiting Reagent marketed by Bioreclamation Inc, East Meadow, N.Y. This product is a preparation of immunoglobulins (IgG and IgM) from multiple species, mainly murine IgG2a, IgG2b, and IgG3 from Balb/c mice. In some embodiments the heterophile antibody may be immunoextracted from the sample using methods known in the art e.g. depleting the sample of the heterophile antibody by binding the interfering antibody to protein A or G. In some embodiments, the heterophile antibody is neutralized using one or more heterophile antibody blockers. Heterophile blockers may be selected from the group consisting of anti-isotype heterophile antibody blockers, anti-idiotype heterophile antibody blockers, and anti-anti-idiotype heterophile antibody blockers. In some embodiments a combination of heterophile antibody blockers may be used.

Label is added either with or following the addition of sample and washing. Protocols for binding of antibody and other immunolabels to proteins and other molecules are well-known in the art. If the label binding step is separate from capture binding, the time allowed for label binding can be important, e.g., in the clinical setting. In some embodiments, the time allowed for binding of the molecule of interest to the label, e.g., antibody-dye, is less than about 12, 10, 8, 6, 4, 3, 2, or 1 hours, or less than about 60, 50, 40, 30, 25, 20, 15, 10, or 5 minutes. In some embodiments, the time allowed for binding of the molecule of interest to the label, e.g., antibody-dye, is less than about 60 minutes. In some embodiments, the time allowed for binding of the molecule of interest to the label, e.g., antibody-dye, is less than about 40 minutes. In some embodiments, the time allowed for binding of the molecule of interest to the label, e.g., antibody-dye, is less than about 30 minutes. In some embodiments, the time allowed for binding of the molecule of interest to the label, e.g., antibody-dye, is less than about 20 minutes. In some embodiments, the time allowed for binding of the molecule of interest to the label, e.g., antibody-dye, is less than about 15 minutes. In some embodiments, the time allowed for binding of the molecule of interest to the label, e.g., antibody-dye, is less than about 10 minutes. In some embodiments, the time allowed for binding of the molecule of interest to the label, e.g., antibody-dye, is less than about 5 minutes. Excess label is removed by washing.

Label is then eluted from the protein of interest. Preferred elution buffers are effective in releasing the label without generating significant background. It is also useful if the elution buffer is bacteriostatic. Elution buffers of use in the invention include a chaotrope, e.g., urea or a guanidinium compound; a buffer, e.g., borate buffered saline; a protein carrier, e.g., an albumin, such as human, bovine, or fish albumin, or an IgG, to coat the wall of the capillary tube in the detection instrument; and a surfactant, e.g., an ionic or nonionic detergent, selected so as to produce a relatively low background, e.g., Tween 20, Triton X-100, or SDS.

The elution buffer/label aliquot that is sampled into the single molecule detector is referred to as the "processing sample," to distinguish it from the original sample which was obtained from an individual.

In another embodiment, the solid phase binding assay may employ a competitive binding assay format. One such method comprises a) competitively binding to a capture antibody immobilized on a binding surface i) a molecule of interest, e.g., marker of a biological state, in a sample and ii) a labeled analog of the molecule comprising a detectable label (the detection reagent) and b) measuring the amount of the label using a single particle analyzer. Another such method comprises a) competitively binding to an antibody having a detectable label (the detection reagent) i) a molecule of interest, e.g., marker of a biological state in a sample and ii) an analog of the molecule that is immobilized on a binding surface (the capture reagent) and b) measuring the amount of the label using a single particle analyzer. An "analog of a molecule" refers, herein, to a species that competes with a molecule for binding to a capture antibody. Examples of competitive immunoassays are disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

C. Detection of Molecule of Interest and Determination of Concentration

Following elution, the label is run through a single molecule detector in e.g., the elution buffer. A processing sample may contain no label, a single label, or a plurality of labels. The number of labels corresponds or is proportional to (if dilutions or fractions of samples are used) the number of molecules of the molecule of interest, e.g., marker of a biological state captured during the capture step.

Any suitable single molecule detector capable of detecting the label used with the molecule of interest may be used. Suitable single molecule detectors are described herein. Typically the detector will be part of a system that includes an automatic sampler for sampling prepared samples, and, optionally, a recovery system to recover samples.

In some embodiments, the processing sample is analyzed in a single molecule analyzer that utilizes a capillary flow system, and that includes a capillary flow cell, a laser to illuminate an interrogation space in the capillary through which processing sample is passed, a detector to detect radiation emitted from the interrogation space, and a source of motive force to move a processing sample through the interrogation space. In some embodiments, the single molecule analyzer further comprises a microscope objective lens that collects light emitted from processing sample as it passes through the interrogation space, e.g., a high numerical aperture microscope objective. In some embodiments, the laser and detector are in a confocal arrangement. In some embodiments, the laser is a continuous wave laser. In some embodiments, the detector is a avalanche photodiode detector. In some embodiments, the source of motive force is a pump to provide pressure. In some embodiments, the invention provides an analyzer system that includes a sampling system capable of automatically sampling a plurality of samples providing a fluid communication between a sample container and the interrogation space. In some embodiments, the interrogation space has a volume of between about 0.001 and 500 pL, or between about 0.01 pL and 100 pL, or between about 0.01 pL and 10 pL, or between about 0.01 pL and 5 pL, or between about 0.01 pL and 0.5 pL, or between about 0.02 pL and about 300 pL, or between about 0.02 pL and about 5 pL or between about 0.02 pL and about 5 pL or between about 0.02 pL and about 0.5 pL or between about 0.02 pL and about 2 pL, or between about 0.05 pL and about 50 pL, or between about 0.05 pL and about 5 pL, or between about 0.05 pL and about 0.5 pL, or between about 0.05 pL and about 0.2 pL, or between about 0.1 pL and about 25 pL. In some embodiments, the interrogation space has a volume between about 0.004 pL and 100 pL. In some embodiments, the interrogation space has a volume between about 0.02 pL and 50 pL. In some embodiments, the interrogation space has a volume between about 0.001 pL and 10 pL. In some embodiments, the interrogation space has a volume between about 0.001 pL and 10 pL. In some embodiments, the interrogation space has a volume between about 0.01 pL and 5 pL. In some embodiments, the interrogation space has a volume between about 0.02 pL and about 5 pL. In some embodiments, the interrogation space has a volume between about 0.05 pL and 5 pL. In some embodiments, the interrogation space has a volume between about 0.05 pL and 10 pL. In some embodiments, the interrogation space has a volume between about 0.5 pL and about 5 pL. In some embodiments, the interrogation space has a volume between about 0.02 pL and about 0.5 pL.

In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space, an avalanche photodiode detector to detect radiation emitted from the interrogation space, and a pump to provide pressure to move a processing sample through the interrogation space, where the interrogation space is between about 0.02 pL and about 50 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.004 pL and about 100 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.05 pL and about 1 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.05 pL and about 5 pL. In some embodiments, the single molecule detector used in the methods of the invention utilizes a capillary flow system, and includes a capillary flow cell, a continuous wave laser to illuminate an interrogation space in the capillary through which processing sample is passed, a high numerical aperture microscope objective lens that collects light emitted from processing sample as it passes through the interrogation space wherein the lens has a numerical aperture of at least about 0.8, an avalanche photodiode detector to detect radiation emitted from the interrogation space, and a pump to provide pressure to move a processing sample through the interrogation space, where the interrogation space is between about 0.5 pL and about 5 pL. In any of these embodiments the analyzer may contain not more than one interrogation space.

In some embodiments, the single molecule detector is capable of determining a concentration for a molecule of interest in a sample where sample may range in concentration over a range of at least about 100-fold, or 1000-fold, or 10,000-fold, or 100,000-fold, or 300,00-fold, or 1,000,000-fold, or 10,000,000-fold, or 30,000,000-fold.

In some embodiments, the methods of the invention utilize a single molecule detector capable detecting a difference of less than about 50%, 40%, 30%, 20%, 15%, or 10% in concentration of an analyte between a first sample and a second sample that are introduced into the detector, where the volume of the first sample and said second sample introduced into the analyzer is less than about 100, 90, 80, 70, 60, 50, 40, 30, 20, 15, 10, 5, 4, 3, 2, or 1 ul, and wherein the analyte is present at a concentration of less than about 100, 90, 80, 70, 60, 50, 40, 30, 20, 15, 10, 5, 4, 3, 2, or 1 femtomolar. In some embodiments, the methods of the invention utilize a single molecule detector capable detecting a difference of less than about 50% in concentration of an analyte between a first sample and a second sample that are introduced into the detector, where the volume of the first sample and said second sample introduced into the analyzer is less than about 100 ul, and wherein the analyte is present at a concentration of less than about 100 femtomolar. In some embodiments, the methods of the invention utilize a single molecule detector capable detecting a difference of less than about 40% in concentration of an analyte between a first sample and a second sample that are introduced into the detector, where the volume of the first sample and said second sample introduced into the analyzer is less than about 50 ul, and wherein the analyte is present at a concentration of less than about 50 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 20 ul, and wherein the analyte is present at a concentration of less than about 20 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 10 ul, and wherein the analyte is present at a concentration of less than about 10 femtomolar. In some embodiments, the methods of the invention utilize a single molecule detector capable detecting a difference of less than about 20% in concentration of an analyte between a first sample and a second sample that are introduced into the detector, where the volume of the first sample and said second sample introduced into the analyzer is less than about 5 ul, and wherein the analyte is present at a concentration of less than about 5 femtomolar.

The single molecule detector and systems are described in more detail below. Further embodiments of single molecule analyzers useful in the methods of the invention, such as detectors with more than one interrogation window, detectors utilize electrokinetic or electrophoretic flow, and the like, may be found in U.S. patent application Ser. No. 11/048,660, incorporated by reference herein in its entirety.

Between runs the instrument may be washed. A wash buffer that maintains the salt and surfactant concentrations of the sample may be used in some embodiments to maintain the conditioning of the capillary; i.e., to keep the capillary surface relatively constant between samples to reduce variability.

A feature that contributes to the extremely high sensitivity of the instruments and methods of the invention is the method of detecting and counting labels, which, in some embodiments, are attached to single molecules to be detected or, more typically, correspond to a single molecule to be detected. Briefly, the processing sample flowing through the capillary is effectively divided into a series of detection events, by subjecting a given interrogation space of the capillary to EM radiation from a laser that emits light at an appropriate excitation wavelength for the fluorescent moiety used in the label for a predetermined period of time, and detecting photons emitted during that time. Each predetermined period of time is a "bin." If the total number of photons detected in a given bin exceeds a predetermined threshold level, a detection event is registered for that bin, i.e., a label has been detected. If the total number of photons is not at the predetermined threshold level, no detection event is registered. In some embodiments, processing sample concentration is dilute enough that, for a large percentage of detection events, the detection event represents only one label passing through the window, which corresponds to a single molecule of interest in the original sample, that is, few detection events represent more than one label in a single bin. In some embodiments, further refinements are applied to allow greater concentrations of label in the processing sample to be detected accurately, i.e., concentrations at which the probability of two or more labels being detected as a single detection event is no longer insignificant.

Although other bin times may be used without departing from the scope of the present invention, in some embodiments the bin times are selected in the range of about 1 microsecond to about 5 ms. In some embodiments, the bin time is more than about 1, 2, 3, 4, 5, 6, 7, 8, 9, 10, 15, 20, 30, 40, 50, 60, 70, 80, 90, 100, 200, 250, 300, 400, 500, 600, 700, 750, 800, 900, 1000, 2000, 3000, 4000, or 5000 microseconds. In some embodiments, the bin time is less than about 2, 3, 4, 5, 6, 7, 8, 9, 10, 15, 20, 30, 40, 50, 60, 70, 80, 90, 100, 200, 250, 300, 400, 500, 600, 700, 750, 800, 900, 1000, 2000, 3000, 4000, or 5000 microseconds. In some embodiments, the bin time is about 1 to 1000 microseconds. In some embodiments, the bin time is about 1 to 750 microseconds. In some embodiments, the bin time is about 1 to 500 microseconds. In some embodiments, the bin time is about 1 to 250 microseconds. In some embodiments, the bin time is about 1 to 100 microseconds. In some embodiments, the bin time is about 1 to 50 microseconds. In some embodiments, the bin time is about 1 to 40 microseconds. In some embodiments, the bin time is about 1 to 30 microseconds. In some embodiments, the bin time is about 1 to 500 microseconds. In some embodiments, the bin time is about 1 to 20 microseconds. In some embodiments, the bin time is about 1 to 10 microseconds. In some embodiments, the bin time is about 1 to 500 microseconds. In some embodiments, the bin time is about 1 to 5 microseconds. In some embodiments, the bin time is about 5 to 500 microseconds. In some embodiments, the bin time is about 5 to 250 microseconds. In some embodiments, the bin time is about 5 to 100 microseconds. In some embodiments, the bin time is about 5 to 50 microseconds. In some embodiments, the bin time is about 5 to 20 microseconds. In some embodiments, the bin time is about 5 to 10 microseconds. In some embodiments, the bin time is about 10 to 500 microseconds. In some embodiments, the bin time is about 10 to 250 microseconds. In some embodiments, the bin time is about 10 to 100 microseconds. In some embodiments, the bin time is about 10 to 50 microseconds. In some embodiments, the bin time is about 10 to 30 microseconds. In some embodiments, the bin time is about 10 to 20 microseconds. In some embodiments, the bin time is about 5 microseconds. In some embodiments, the bin time is about 5 microseconds. In some embodiments, the bin time is about 6 microseconds. In some embodiments, the bin time is about 7 microseconds. In some embodiments, the bin time is about 8 microseconds. In some embodiments, the bin time is about 9 microseconds. In some embodiments, the bin time is about 10 microseconds. In some embodiments, the bin time is about 11 microseconds. In some embodiments, the bin time is about 12 microseconds. In some embodiments, the bin time is about 13 microseconds. In some embodiments, the bin time is about 14 microseconds. In some embodiments, the bin time is about 5 microseconds. In some embodiments, the bin time is about 15 microseconds. In some embodiments, the bin time is about 16 microseconds. In some embodiments, the bin time is about 17 microseconds. In some embodiments, the bin time is about 18 microseconds. In some embodiments, the bin time is about 19 microseconds. In some embodiments, the bin time is about 20 microseconds. In some embodiments, the bin time is about 25 microseconds. In some embodiments, the bin time is about 30 microseconds. In some embodiments, the bin time is about 40 microseconds. In some embodiments, the bin time is about 50 microseconds. In some embodiments, the bin time is about 100 microseconds. In some embodiments, the bin time is about 250 microseconds. In some embodiments, the bin time is about 500 microseconds. In some embodiments, the bin time is about 750 microseconds. In some embodiments, the bin time is about 1000 microseconds.

In some embodiments, the background noise level is determined from the mean noise level, or the root-mean-square noise. In other cases, a typical noise value or a statistical value is chosen. In most cases, the noise is expected to follow a Poisson distribution. Thus, in some embodiments, determining the concentration of a particle-label complex in a sample comprises determining the background noise level.

Thus, as a label flows through the capillary flow cell, it is irradiated by the laser beam to generate a burst of photons. The photons emitted by the label are discriminated from background light or background noise emission by considering only the bursts of photons that have energy above a predetermined threshold energy level which accounts for the amount of background noise that is present in the sample. Background noise typically comprises low frequency emission produced, for example, by the intrinsic fluorescence of non-labeled particles that are present in the sample, the buffer or diluent used in preparing the sample for analysis, Raman scattering and electronic noise. In some embodiments, the value assigned to the background noise is calculated as the average background signal noise detected in a plurality of bins, which are measurements of photon signals that are detected in an interrogation space during a predetermined length of time. Thus in some embodiments, background noise is calculated for each sample as a number specific to that sample.

Given the value for the background noise, the threshold energy level can be assigned. As discussed above, the threshold value is determined to discriminate true signals (due to fluorescence of a label) from the background noise. Care must be taken in choosing a threshold value such that the number of false positive signals from random noise is minimized while the number of true signals which are rejected is also minimized. Methods for choosing a threshold value include determining a fixed value above the noise level and calculating a threshold value based on the distribution of the noise signal. In one embodiment, the threshold is set at a fixed number of standard deviations above the background level. Assuming a Poisson distribution of the noise, using this method one can estimate the number of false positive signals over the time course of the experiment. In some embodiments, the threshold level is calculated as a value of 4 sigma above the background noise. For example, given an average background noise level of 200 photons, the analyzer system establishes a threshold level of $4\sqrt{200}$ above the average background/noise level of 200 photons to be 256 photons. Thus, in some embodiments, determining the concentration of a label in a sample includes establishing the threshold level above which photon signals represent the presence of a label. Conversely, photon signals that have an energy level that is not greater than that of the threshold level indicate the absence of a label.

Many bin measurements are taken to determine the concentration of a sample, and the absence or presence of a label is ascertained for each bin measurement. Typically, 60,000 measurements or more can made in one minute (e.g., in embodiments in which the bin size is 1 ms—for smaller bin sizes the number of measurements is correspondingly larger, e.g., 6,000,000 measurements per minute for a bin size of 10 microseconds). Thus, no single measurement is crucial and the method provides for a high margin of error. The bins that are determined not to contain a label ("no" bins) are discounted and only the measurements made in the bins that are determined to contain label ("yes" bins) are accounted in determining the concentration of the label in the processing sample. Discounting measurements made in the "no" bins or bins that are devoid of label increases the signal to noise ratio and the accuracy of the measurements. Thus, in some embodiments, determining the concentration of a label in a sample comprises detecting the bin measurements that reflect the presence of a label.

The signal to noise ratio or the sensitivity of the analyzer system can be increased by minimizing the time that background noise is detected during a bin measurement in which a particle-label complex is detected. For example, in a bin measurement lasting 1 millisecond during which one particle-label complex is detected when passing across an interrogation space within 250 microseconds, 750 microseconds of the 1 millisecond are spent detecting background noise emission. The signal to noise ratio can be improved by decreasing the bin time. In some embodiments, the bin time is 1 millisecond. In other embodiments, the bin time is 750, 500, 250 microseconds, 100 microseconds, 50 microseconds, 25 microseconds or 10 microseconds. Other bin times are as described herein.

Other factors that affect measurements are the brightness or dimness of the fluorescent moiety, the flow rate, and the power of the laser. Various combinations of the relevant factors that allow for detection of label will be apparent to those of skill in the art. In some embodiments, the bin time is adjusted without changing the flow rate. It will be appreciated by those of skill in the art that as bin time decreases, laser power output directed at the interrogation space must increase to maintain a constant total energy applied to the interrogation space during the bin time. For example, if bin time is decreased from 1000 microseconds to 250 microseconds, as a first approximation, laser power output must be increased approximately four-fold. These settings allow for the detection of the same number of photons in a 250 μs as the number of photons counted during the 1000 μs given the previous settings, and allow for faster analysis of sample with lower backgrounds and thus greater sensitivity. In addition, flow rates may be adjusted in order to speed processing of sample. These numbers are merely exemplary, and the skilled practitioner can adjust the parameters as necessary to achieve the desired result.

In some embodiments, the interrogation space encompasses the entire cross-section of the sample stream. When the interrogation space encompasses the entire cross-section of the sample stream, only the number of labels counted and the volume passing through a cross-section of the sample stream in a set length of time are needed to calculate the concentration of the label in the processing sample. In some embodiments, the interrogation space can be defined to be smaller than the cross-sectional area of sample stream by, for example, the interrogation space is defined by the size of the spot illuminated by the laser beam. In some embodiments, the interrogation space can be defined by adjusting the apertures 306 (FIG. 1A) or 358 and 359 (FIG. 1B) of the analyzer and reducing the illuminated volume that is imaged by the objective lens to the detector. In the embodiments when the interrogation space is defined to be smaller than the cross-sectional area of sample stream, the concentration of the label can be determined by interpolation of the signal emitted by the complex from a standard curve that is generated using one or more samples of known standard concentrations. In yet other embodiments, the concentration of the label can be determined by comparing the measured particles to an internal label standard. In embodiments when a diluted sample is analyzed, the dilution factor is accounted in calculating the concentration of the molecule of interest in the starting sample.

As discussed above, when the interrogation space encompasses the entire cross-section of the sample stream, only the number of labels counted passing through a cross-section of the sample stream in a set length of time (bin) and the volume of sample that was interrogated in the bin are needed to calculate the concentration the sample. The total number of labels contained in the "yes" bins is determined and related to the sample volume represented by the total number of bins used in the analysis to determine the concentration of labels in the processing sample. Thus, in one embodiment, determining the concentration of a label in a processing sample comprises determining the total number of labels detected "yes" bins and relating the total number of detected labels to the total sample volume that was analyzed. The total sample volume that is analyzed is the sample volume that is passed through the capillary flow cell and across the interrogation space in a specified time interval. Alternatively, the concentration of the label complex in a sample is determined by interpolation of the signal emitted by the label in a number of bins from a standard curve that is generated by determining the signal emitted by labels in the same number of bins by standard samples containing known concentrations of the label.

In some embodiments, the number of individual labels that are detected in a bin is related to the relative concentration of the particle in the processing sample. At relatively low concentrations, for example at concentrations below about $10^{-16}$ M the number of labels is proportional to the photon signal that is detected in a bin. Thus, at low concentrations of label the photon signal is provided as a digital signal. At relatively higher concentrations, for example at concentrations greater than about $10^{-16}$ M, the proportionality of photon signal to a label is lost as the likelihood of two or more labels crossing the interrogation space at about the same time and being counted as one becomes significant. Thus, in some embodiments, individual particles in a sample of a concentration greater than about $10^{-16}$ M are resolved by decreasing the length of time of the bin measurement.

Alternatively, in other embodiments, the total the photon signal that is emitted by a plurality of particles that are present in any one bin is detected. These embodiments allow for single molecule detectors of the invention wherein the dynamic range is at least 3, 3.5, 4, 4.5, 5.5, 6, 6.5, 7, 7.5, 8, or more than 8 logs.

"Dynamic range," as that term is used herein, refers to the range of sample concentrations that may be quantitated by the instrument without need for dilution or other treatment to alter the concentration of successive samples of differing concentrations, where concentrations are determined with an accuracy appropriate for the intended use. For example, if a microtiter plate contains a sample of 1 femtomolar concentration for an analyte of interest in one well, a sample of 10,000 femtomolar concentration for an analyte of interest in another well, and a sample of 100 femtomolar concentration for the analyte in a third well, an instrument with a dynamic range of at least 4 logs and a lower limit of quantitation of 1 femtomolar is able to accurately quantitate the concentration of all the samples without the need for further treatment to adjust concentration, e.g., dilution. Accuracy may be determined by standard methods, e.g., using a series of standards of concentrations that span the dynamic range and constructing a standard curve. Standard measures of fit of the resulting standard curve may be used as a measure of accuracy, e.g., an $r^2$ greater than about 0.7, 0.75, 0.8, 0.85, 0.9, 0.91, 0.92, 0.93, 0.94, 0.95, 0.96, 0.97, 0.98, or 0.99.

Increased dynamic range is achieved by altering the manner in which data from the detector is analyzed, and/or by the use of an attenuator between the detector and the interrogation space. At the low end of the range, where processing sample is sufficiently dilute that each detection event, i.e., each burst of photons above a threshold level in a bin (the "event photons"), likely represents only one label, the data is analyzed to count detection events as single molecules. I.e., each bin is analyzed as a simple "yes" or "no" for the presence of label, as described above. For a more concentrated processing sample, where the likelihood of two or more labels occupying a single bin becomes significant, the number of event photons in a significant number of bins is found to be substantially greater than the number expected for a single label, e.g., the number of event photons in a significant number of bins corresponds to two-fold, three-fold, or more, than the number of event photons expected for a single label. For these samples, the instrument changes its method of data analysis to one of integrating the total number of event photons for the bins of the processing sample. This total will be proportional to the total number of labels that were in all the bins. For an even more concentrated processing sample, where many labels are present in most bins, background noise becomes an insignificant portion of the total signal from each bin, and the instrument changes its method of data analysis to one of counting total photons per bin (including background). An even further increase in dynamic range can be achieved by the use of an attenuator between the flow cell and the detector, when concentrations are such that the intensity of light reaching the detector would otherwise exceed the capacity of the detector for accurately counting photons, i.e., saturate the detector.

The instrument may include a data analysis system that receives input from the detector and determines the appropriate analysis method for the sample being run, and outputs values based on such analysis. The data analysis system may further output instructions to use or not use an attenuator, if an attenuator is included in the instrument.

By utilizing such methods, the dynamic range of the instrument can be dramatically increased. Thus, in some embodiments, the instrument is capable of measuring concentrations of samples over a dynamic range of more than about 1000 (3 log), 10,000 (4 log), 100,000 (5 log), 350,000 (5.5 log), 1,000,000 (6 log), 3,500,000 (6.5 log), 10,000,000 (7 log), 35,000,000 (7.5 log), or 100,000,000 (8 log). In some embodiments, the instrument is capable of measuring concentrations of samples over a dynamic range of more than about 100,000 (5 log). In some embodiments, the instrument is capable of measuring concentrations of samples over a dynamic range of more than about 1,000,000 (6 log). In some embodiments, the instrument is capable of measuring concentrations of samples over a dynamic range of more than about 10,000,000 (7 log). In some embodiments, the instrument is capable of measuring the concentrations of samples over a dynamic range of from about 1-10 femtomolar to at least about 1000; 10,000; 100,000; 350,000; 1,000,000; 3,500,000; 10,000,000, or 35,000,000 femtomolar. In some embodiments, the instrument is capable of measuring the concentrations of samples over a dynamic range of from about 1-10 femtomolar to at least about 10,000 femtomolar. In some embodiments, the instrument is capable of measuring the concentrations of samples over a dynamic range of from about 1-10 femtomolar to at least about 100,000 femtomolar. In some embodiments, the instrument is capable of measuring the concentrations of samples over a dynamic range of from about 1-10 femtomolar to at least about 1,000,000 femtomolar. In some embodiments, the instrument is capable of measuring the concentrations of samples over a dynamic range of from about 1-10 femtomolar to at least about 10,000,000.

In some embodiments, an analyzer or analyzer system of the invention is capable of detecting an analyte, e.g., a biomarker at a limit of detection of less than 1 nanomolar, or 1 picomolar, or 1 femtomolar, or 1 attomolar, or 1 zeptomolar. In some embodiments, the analyzer or analyzer system is capable of detecting a change in concentration of the analyte, or of multiple analytes, e.g., a biomarker or biomarkers, from one sample to another sample of less than about 0.1, 1, 2, 5, 10, 20, 30, 40, 50, 60, or 80% when the biomarker is present at a concentration of less than 1 nanomolar, or 1 picomolar, or 1 femtomolar, or 1 attomolar, or 1 zeptomolar, in the samples, and when the size of each of the sample is less than about 100, 50, 40, 30, 20, 10, 5, 2, 1, 0.1, 0.01, 0.001, or 0.0001 ul. In some embodiments, the analyzer or analyzer system is capable of detecting a change in concentration of the analyte from a first sample to a second sample of less than about 20%, when the analyte is present at a concentration of less than about 1 picomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 100 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 50 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 5 femtomolar, and when the size of each of the samples is less than about 50 µl. In some embodiments, the analyzer or analyzer system is capable of detecting a change in concentration of the analyte from a first sample to a second sample of less than about 20%, when the analyte is present at a concentration of less than about 5 femtomolar, and when the size of each of the samples is less than about 5 µl. In some embodiments, the analyzer or analyzer system is capable of detecting a change in concentration of the analyte from a first sample to a second sample of less than about 20%, when the analyte is present at a concentration of less than about 1 femtomolar, and when the size of each of the samples is less than about 5 µl.

V. Instruments and Systems Suitable for Highly Sensitive Analysis of Molecules

The methods of the invention utilize analytical instruments of high sensitivity, e.g., single molecule detectors. Such single molecule detectors include embodiments as hereinafter described.

In some embodiments, the invention provides an analyzer system kit for detecting a single protein molecule in a sample, said system includes an analyzer system for detecting a single protein molecule in a sample and least one label that includes a fluorescent moiety and a binding partner for the protein molecule, where the analyzer includes an electromagnetic radiation source for stimulating the fluorescent moiety; a capillary flow cell for passing the label; a source of motive force for moving the label in the capillary flow cell; an interrogation space defined within the capillary flow cell for receiving electromagnetic radiation emitted from the electromagnetic source; and an electromagnetic radiation detector operably connected to the interrogation space for measuring an electromagnetic characteristic of the stimulated fluorescent moiety, where the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules.

Figure 12:
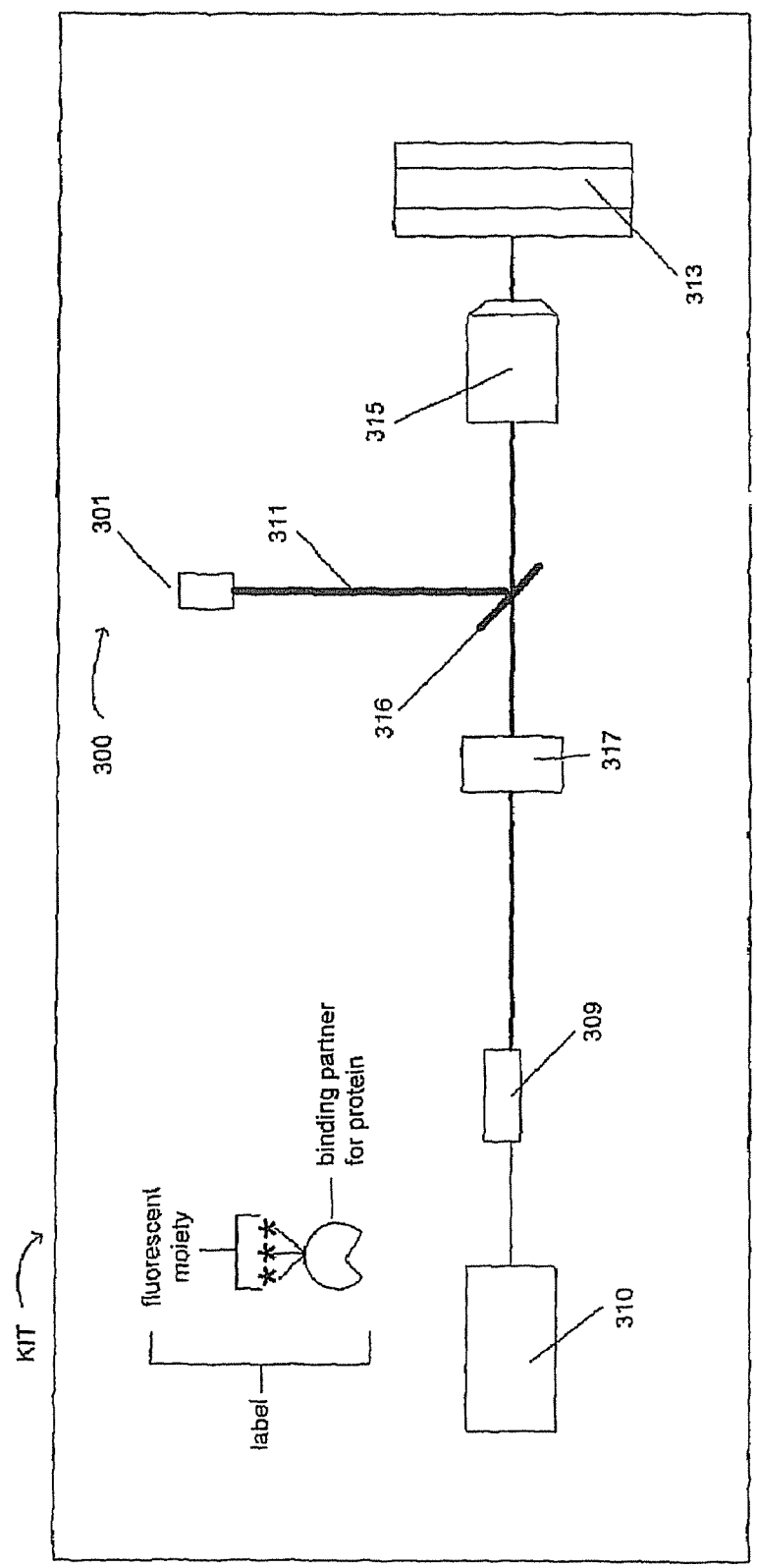
FIG. 12 A schematic representation of a kit that includes an analyzer system for detecting a single protein molecule in a sample and least one label that includes a fluorescent moiety and a binding partner for the protein molecule, where the analyzer includes an electromagnetic radiation source for stimulating the fluorescent moiety; a capillary flow cell for passing the label; a source of motive force for moving the label in the capillary flow cell; an interrogation space defined within the capillary flow cell for receiving electromagnetic radiation emitted from the electromagnetic source; and an electromagnetic radiation detector operably connected to the interrogation space for measuring an electromagnetic characteristic of the stimulated fluorescent moiety, where the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules

One embodiment of an analyzer kit of the invention is depicted in FIG. 12. The kit includes a label for a protein molecule that includes a binding partner for a protein molecule and a fluorescent moiety. The kit further includes an analyzer system for detecting a single protein molecule (300) that includes an electromagnetic radiation source 301 for stimulating the fluorescent moiety, a capillary flow cell 313 for passing the label; a source of motive force for moving the label in the capillary flow cell (not shown); an interrogation space defined within the capillary flow cell for receiving electromagnetic radiation emitted from the electromagnetic source 314 (FIG. 2A); and an electromagnetic radiation detector 309 operably connected to the interrogation space for measuring an electromagnetic characteristic of the stimulated fluorescent moiety, where the fluorescent moiety is capable of emitting at least about 200 photons when simulated by a laser emitting light at the excitation wavelength of the moiety, where the laser is focused on a spot not less than about 5 microns in diameter that contains the moiety, and where the total energy directed at the spot by the laser is no more than about 3 microJoules. In some embodiments, the beam 311 from an electromagnetic radiation source 301 is focused by the microscope objective 315 to form one interrogation space 314 (FIG. 2A) within the capillary flow cell 313. the microscope objective may have a numerical aperture of equal to or greater than 0.7, 0.8, 0.9, or 1.0 in some embodiments.

In some embodiments of the analyzer system kit, the analyzer comprises not more than one interrogation space. In some embodiments, the electromagnetic radiation source is a laser that has a power output of at least about 3, 5, 10, or 20 mW. In some embodiments, the fluorescent moiety comprises a fluorescent molecule. In some embodiments, the fluorescent molecule is a dye molecule, such as a dye molecule that comprises at least one substituted indolium ring system in which the substituent on the 3-carbon of the indolium ring contains a chemically reactive group or a conjugated substance. In some embodiments, the fluorescent moiety is a quantum dot. In some embodiments, the electromagnetic radiation source is a continuous wave electromagnetic radiation source, such as a light-emitting diode or a continuous wave laser. In some embodiments, the motive force is pressure. In some embodiments, the detector is an avalanche photodiode detector. In some embodiments, the analyzer utilizes a confocal optical arrangement for deflecting a laser beam onto said interrogation space and for imaging said stimulated dye molecule (shown in FIG. 12), wherein said confocal optical arrangement comprises an objective lens having a numerical aperture of at least about 0.8. In some embodiments, the analyzer further comprises a sampling system capable of automatically sampling a plurality of samples and providing a fluid communication between a sample container and said interrogation space. In some embodiments, the analyzer system further comprises a sample recovery system in fluid communication with said interrogation space, wherein said recovery system is capable of recovering substantially all of said sample. In some embodiments, the kit further includes instructions for use of the system.

A. Apparatus/System

In one aspect, the methods described herein utilize an analyzer system capable of detecting a single molecule in a sample. In one embodiment, the analyzer system is capable of single molecule detection of a fluorescently labeled particle wherein the analyzer system detects energy emitted by an excited fluorescent label in response to exposure by an electromagnetic radiation source when the single particle is present in an interrogation space defined within a capillary flow cell fluidly connected to the sampling system of the analyzer system. In a further embodiment of the analyzer system, the single particle moves through the interrogation space of the capillary flow cell by means of a motive force. In another embodiment of the analyzer system, an automatic sampling system may be included in the analyzer system for introducing the sample into the analyzer system. In another embodiment of the analyzer system, a sample preparation system may be included in the analyzer system for preparing a sample. In a further embodiment, the analyzer system may contain a sample recovery system for recovering at least a portion of the sample after analysis is complete.

In one aspect, the analyzer system consists of an electromagnetic radiation source for exciting a single particle labeled with a fluorescent label. In one embodiment, the electromagnetic radiation source of the analyzer system is a laser. In a further embodiment, the electromagnetic radiation source is a continuous wave laser.

In a typical embodiment, the electromagnetic radiation source excites a fluorescent moiety attached to a label as the label passes through the interrogation space of the capillary flow cell. In some embodiments, the fluorescent label moiety includes one or more fluorescent dye molecules. In some embodiments, the fluorescent label moiety is a quantum dot. Any fluorescent moiety as described herein may be used in the label.

A label is exposed to electromagnetic radiation when the label passes through an interrogation space located within the capillary flow cell. The interrogation space is typically fluidly connected to a sampling system. In some embodiments the label passes through the interrogation space of the capillary flow cell due to a motive force to advance the label through the analyzer system. The interrogation space is positioned such that it receives electromagnetic radiation emitted from the radiation source. In some embodiments, the sampling system is an automated sampling system capable of sampling a plurality of samples without intervention from a human operator.

The label passes through the interrogation space and emits a detectable amount of energy when excited by the electromagnetic radiation source. In one embodiment, an electromagnetic radiation detector is operably connected to the interrogation space. The electromagnetic radiation detector is capable of detecting the energy emitted by the label, e.g., by the fluorescent moiety of the label.

In a further embodiment of the analyzer system, the system further includes a sample preparation mechanism where a sample may be partially or completely prepared for analysis by the analyzer system. In some embodiments of the analyzer system, the sample is discarded after it is analyzed by the system. In other embodiments, the analyzer system further includes a sample recovery mechanism whereby at least a portion, or alternatively all or substantially all, of the sample may be recovered after analysis. In such an embodiment, the sample can be returned to the origin of the sample. In some embodiments, the sample can be returned to microtiter wells on a sample microtiter plate. The analyzer system typically further consists of a data acquisition system for collecting and reporting the detected signal.

B. Single Particle Analyzer

As shown in FIG. 1A, described herein is one embodiment of an analyzer system 300. The analyzer system 300 includes an electromagnetic radiation source 301, a mirror 302, a lens 303, a capillary flow cell 313, a microscopic objective lens 305, an aperture 306, a detector lens 307, a detector filter 308, a single photon detector 309, and a processor 310 operatively connected to the detector.

Figure 2A:
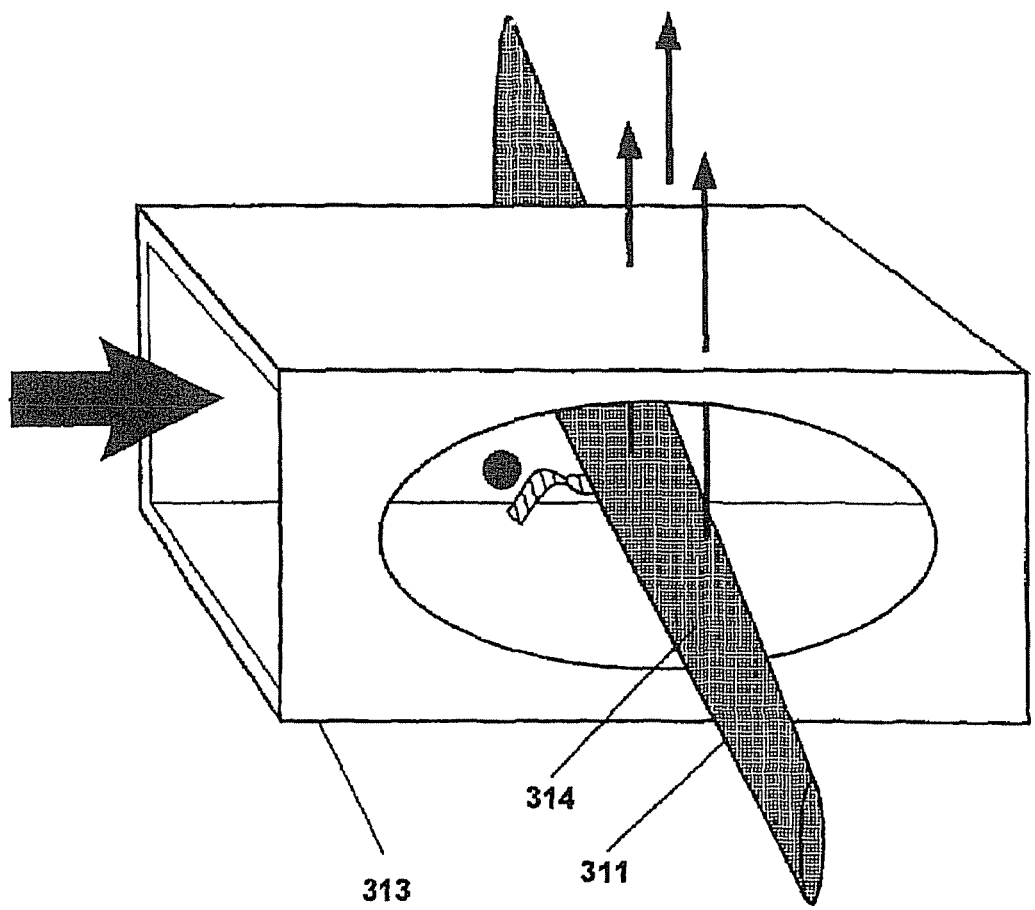
FIGS. 2A and 2B. Schematic diagrams of a capillary flow cell for a single particle analyzer.

In operation the electromagnetic radiation source 301 is aligned so that its output 311 is reflected off of a front surface 312 of mirror 302. The lens 303 focuses the beam 311 onto a single interrogation space (an illustrative example of an interrogation space 314 is shown in FIG. 2A) in the capillary flow cell 313. The microscope objective lens 305 collects light from sample particles and forms images of the beam onto the aperture 306. The aperture 306 affects the fraction of light emitted by the specimen in the interrogation space of the capillary flow cell 313 that can be collected. The detector lens 307 collects the light passing through the aperture 306 and focuses the light onto an active area of the detector 309 after it passes through the detector filters 308. The detector filters 308 minimize aberrant noise signals due to light scatter or ambient light while maximizing the signal emitted by the excited fluorescent moiety bound to the particle. The processor 310 processes the light signal from the particle according to the methods described herein.

In one embodiment, the microscope objective lens 305 is a high numerical aperture microscope objective. As used herein, "high numerical aperture lens" include a lens with a numerical aperture of equal to or greater than 0.6. The numerical aperture is a measure of the number of highly diffracted image-forming light rays captured by the objective. A higher numerical aperture allows increasingly oblique rays to enter the objective lens and thereby produce a more highly resolved image. Additionally, the brightness of an image increases with a higher numerical aperture. High numerical aperture lenses are commercially available from a variety of vendors, and any one lens having a numerical aperture of equal to or greater than approximately 0.6 may be used in the analyzer system. In some embodiments, the lens has a numerical aperture of about 0.6 to about 1.3. In some embodiments, the lens has a numerical aperture of about 0.6 to about 1.0. In some embodiments, the lens has a numerical aperture of about 0.7 to about 1.2. In some embodiments, the lens has a numerical aperture of about 0.7 to about 1.0. In some embodiments, the lens has a numerical aperture of about 0.7 to about 0.9. In some embodiments, the lens has a numerical aperture of about 0.8 to about 1.3. In some embodiments, the lens has a numerical aperture of about 0.8 to about 1.2. In some embodiments, the lens has a numerical aperture of about 0.8 to about 1.0. In some embodiments, the lens has a numerical aperture of at least about 0.6. In some embodiments, the lens has a numerical aperture of at least about 0.7. In some embodiments, the lens has a numerical aperture of at least about 0.8. In some embodiments, the lens has a numerical aperture of at least about 0.9. In some embodiments, the lens has a numerical aperture of at least about 1.0. In some embodiments, the aperture of the microscope objective lens 305 is approximately 1.25. In an embodiment where a microscope objective lens 305 of 0.8 is used, a Nikon 60×/0.8 NA Achromat lens (Nikon, Inc., USA) can be used.

In some embodiments, the electromagnetic radiation source 301 is a laser that emits light in the visible spectrum. In all embodiments, the electromagnetic radiation source is set such that wavelength of the laser is set such that it is of a sufficient wavelength to excite the fluorescent label attached to the particle. In some embodiments, the laser is a continuous wave laser with a wavelength of 639 mm. In other embodiments, the laser is a continuous wave laser with a wavelength of 532 nm. In other embodiments, the laser is a continuous wave laser with a wavelength of 422 nm. In other embodiments, the laser is a continuous wave laser with a wavelength of 405 nm. Any continuous wave laser with a wavelength suitable for exciting a fluorescent moiety as used in the methods and compositions of the invention may be used without departing from the scope of the invention.

In a single particle analyzer system 300, as each particle passes through the beam 311 of the electromagnetic radiation source, the particle enters into an excited state. When the particle relaxes from its excited state, a detectable burst of light is emitted. The excitation-emission cycle is repeated many times by each particle in the length of time it takes for it to pass through the beam allowing the analyzer system 300 to detect tens to thousands of photons for each particle as it passes through an interrogation space 314. Photons emitted by fluorescent particles are registered by the detector 309 (FIG. 1A) with a time delay indicative of the time for the particle label complex to pass through the interrogation space. The photon intensity is recorded by the detector 309 and sampling time is divided into bins, which are uniform, arbitrary, time segments with freely selectable time channel widths. The number of signals contained in each bin evaluated. One or a combination of several statistical analytical methods are employed in order to determine when a particle is present. Such methods include determining the baseline noise of the analyzer system and setting a signal strength for the fluorescent label at a statistical level above baseline noise to eliminate false positive signals from the detector.

The electromagnetic radiation source 301 is focused onto a capillary flow cell 313 of the analyzer system 300 where the capillary flow cell 313 is fluidly connected to the sample system. An interrogation space 314 is shown in FIG. 2A. The beam 311 from the continuous wave electromagnetic radiation source 301 of FIG. 1A is optically focused to a specified depth within the capillary flow cell 313. The beam 311 is directed toward the sample-filled capillary flow cell 313 at an angle perpendicular to the capillary flow cell 313. The beam 311 is operated at a predetermined wavelength that is selected to excite a particular fluorescent label used to label the particle of interest. The size or volume of the interrogation space 314 is determined by the diameter of the beam 311 together with the depth at which the beam 311 is focused. Alternatively, the interrogation space can be determined by running a calibration sample of known concentration through the analyzer system.

When single molecules are detected in the sample concentration, the beam size and the depth of focus required for single molecule detection are set and thereby define the size of the interrogation space 314. The interrogation space 314 is set such that, with an appropriate sample concentration, only one particle is present in the interrogation space 314 during each time interval over which time observations are made.

It will be appreciated that the detection interrogation volume as defined by the beam is not perfectly spherically shaped, and typically is a "bow-tie" shape. However, for the purposes of definition, "volumes" of interrogation spaces are defined herein as the volume encompassed by a sphere of a diameter equal to the focused spot diameter of the beam. The focused spot of the beam 311 may have various diameters without departing from the scope of the present invention. In some embodiments, the diameter of the focused spot of the beam is about 1 to about 5, 10, 15, or 20 microns, or about 5 to about 10, 15, or 20 microns, or about 10 to about 20 microns, or about 10 to about 15 microns. In some embodiments, the diameter of the focused spot of the beam is about 1, 2, 3, 4, 5, 6, 7, 8, 9, 10, 11, 12, 13, 14, 15, 16, 17, 18, 19, or 20 microns. In some embodiments, the diameter of the focused spot of the beam is about 5 microns. In some embodiments, the diameter of the focused spot of the beam is about 10 microns. In some embodiments, the diameter of the focused spot of the beam is about 12 microns. In some embodiments, the diameter of the focused spot of the beam is about 13 microns. In some embodiments, the diameter of the focused spot of the beam is about 14 microns. In some embodiments, the diameter of the focused spot of the beam is about 15 microns. In some embodiments, the diameter of the focused spot of the beam is about 16 microns. In some embodiments, the diameter of the focused spot of the beam is about 17 microns. In some embodiments, the diameter of the focused spot of the beam is about 18 microns. In some embodiments, the diameter of the focused spot of the beam is about 19 microns. In some embodiments, the diameter of the focused spot of the beam is about 20 microns.

Figure 1B:
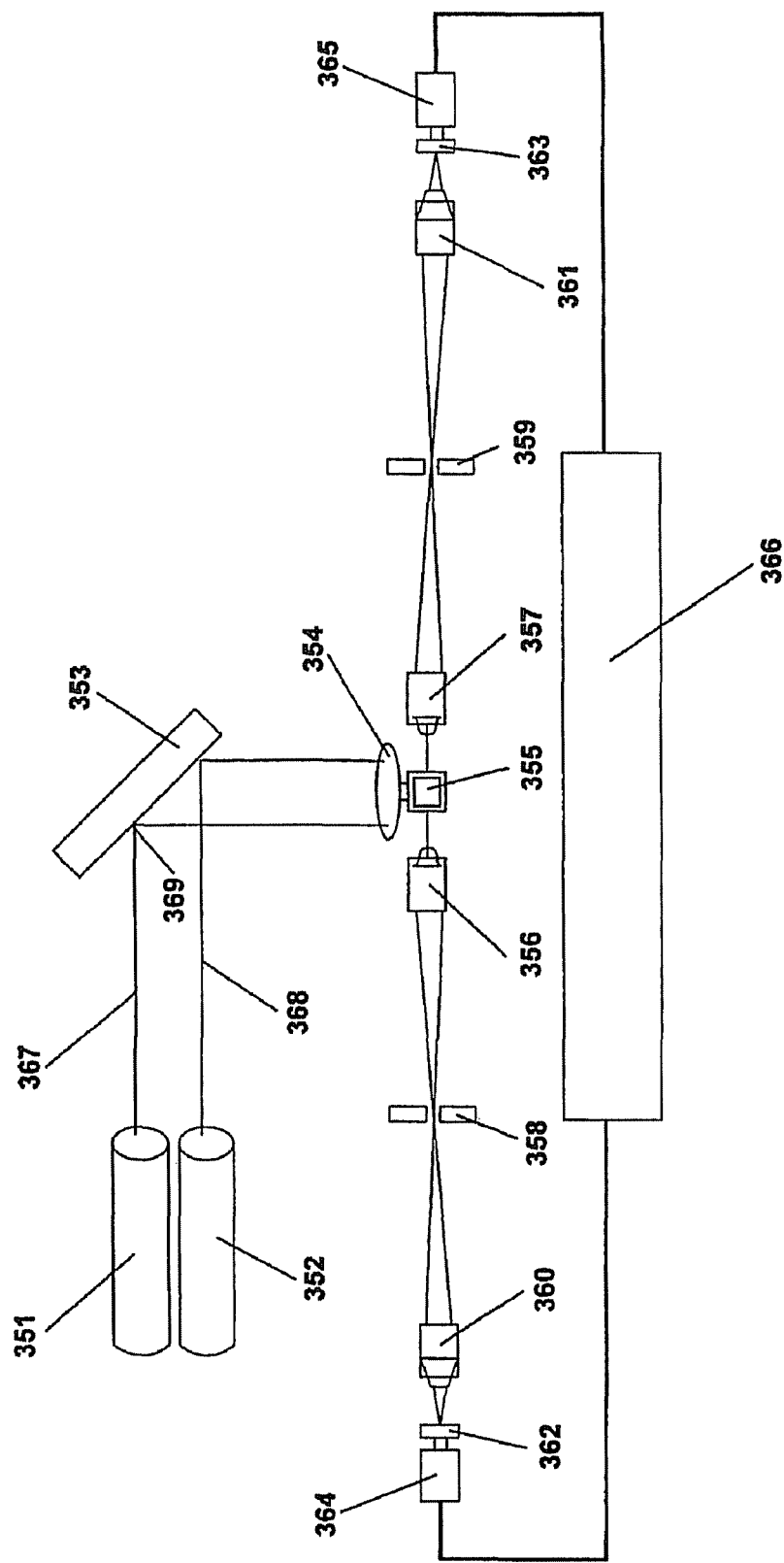

In an alternate embodiment of the single particle analyzer system, more than one electromagnetic radiation source can be used to excite particles labeled with fluorescent labels of different wavelengths. In another alternate embodiment, more than one interrogation space in the capillary flow cell can be used. In another alternate embodiment, multiple detectors can be employed to detect different emission wavelengths from the fluorescent labels. An illustration incorporating each of these alternative embodiments of an analyzer system is shown in FIG. 1B. These embodiments are incorporated by reference from previous U.S. patent application Ser. No. 11/048,660.

In some embodiments of the analyzer system 300, a motive force is required to move a particle through the capillary flow cell 313 of the analyzer system 300. In one embodiment, the motive force can be a form of pressure. The pressure used to move a particle through the capillary flow cell can be generated by a pump. In some embodiments, a Scivex, Inc. HPLC pump can be used. In some embodiments where a pump is used as a motive force, the sample can pass through the capillary flow cell at a rate of 1 µL/min to about 20 µL/min, or about 5 µL/min to about 20 µL/min. In some embodiments, the sample can pass through the capillary flow cell at a rate of about 5 µL/min. In some embodiments, the sample can pass through the capillary flow cell at a rate of about 10 µL/min. In some embodiments, the sample can pass through the capillary flow cell at a rate of about 15 µL/min. In some embodiments, the sample can pass through the capillary flow cell at a rate of about 20 µL/min. In some embodiments, an electrokinetic force can be used to move the particle through the analyzer system. Such a method has been previously disclosed and is incorporated by reference from previous U.S. patent application Ser. No. 11/048,660.

In one aspect of the analyzer system 300, the detector 309 of the analyzer system detects the photons emitted by the fluorescent label. In one embodiment, the photon detector is a photodiode. In a further embodiment, the detector is an avalanche photodiode detector. In some embodiments, the photodiodes can be silicon photodiodes with a wavelength detection of 190 nm and 1100 nm. When germanium photodiodes are used, the wavelength of light detected is between 400 nm to 1700 mm. In other embodiments, when an indium gallium arsenide photodiode is used, the wavelength of light detected by the photodiode is between 800 nm and 2600 nm. When lead sulfide photodiodes are used as detectors, the wavelength of light detected is between 1000 nm and 3500 nm.

In some embodiments, the optics of the electromagnetic radiation source 301 and the optics of the detector 309 are arranged in a conventional optical arrangement. In such an arrangement, the electromagnetic radiation source and the detector are aligned on different focal planes. The arrangement of the laser and the detector optics of the analyzer system as shown in FIGS. 1A and 1B is that of a conventional optical arrangement.

Figure 3A:
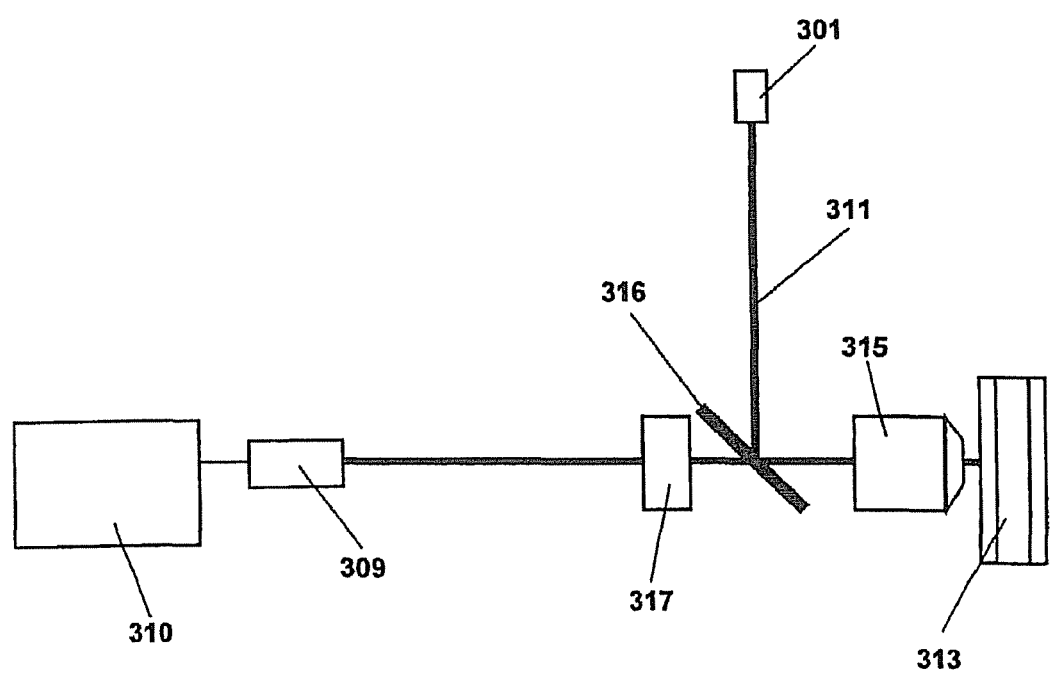
FIG. 3A shows an analyzer that includes one electromagnetic source and one electromagnetic detector.
Figure 3B:
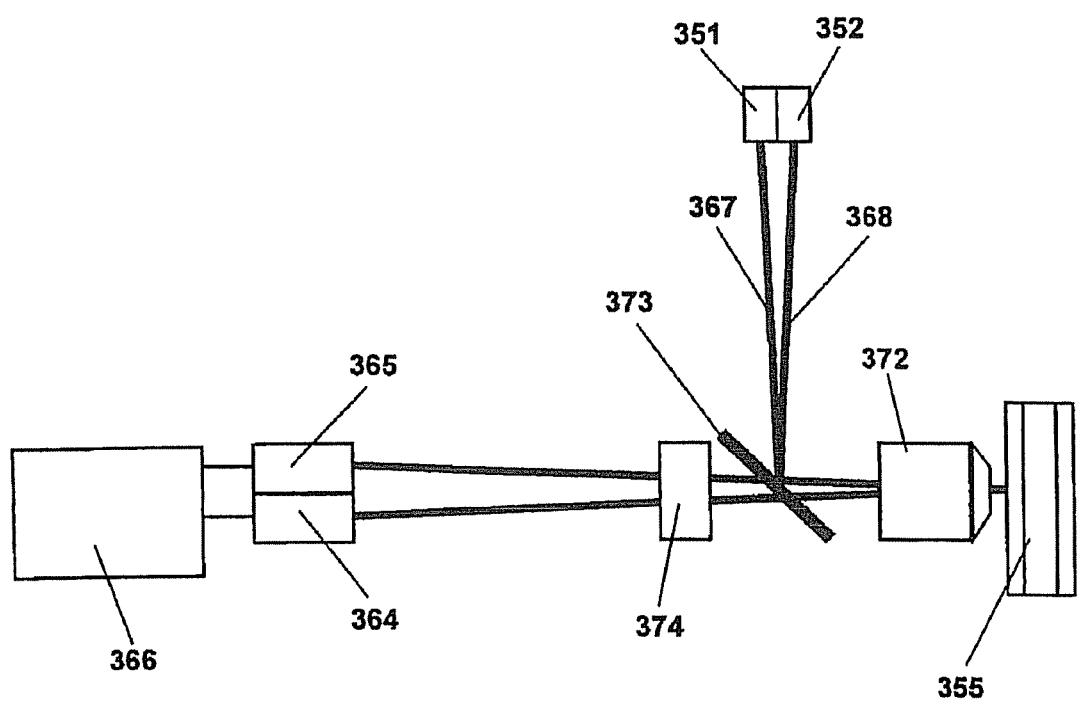
FIG. 3B shows an analyzer that includes two electromagnetic sources and one electromagnetic detectors.
Figure 4:
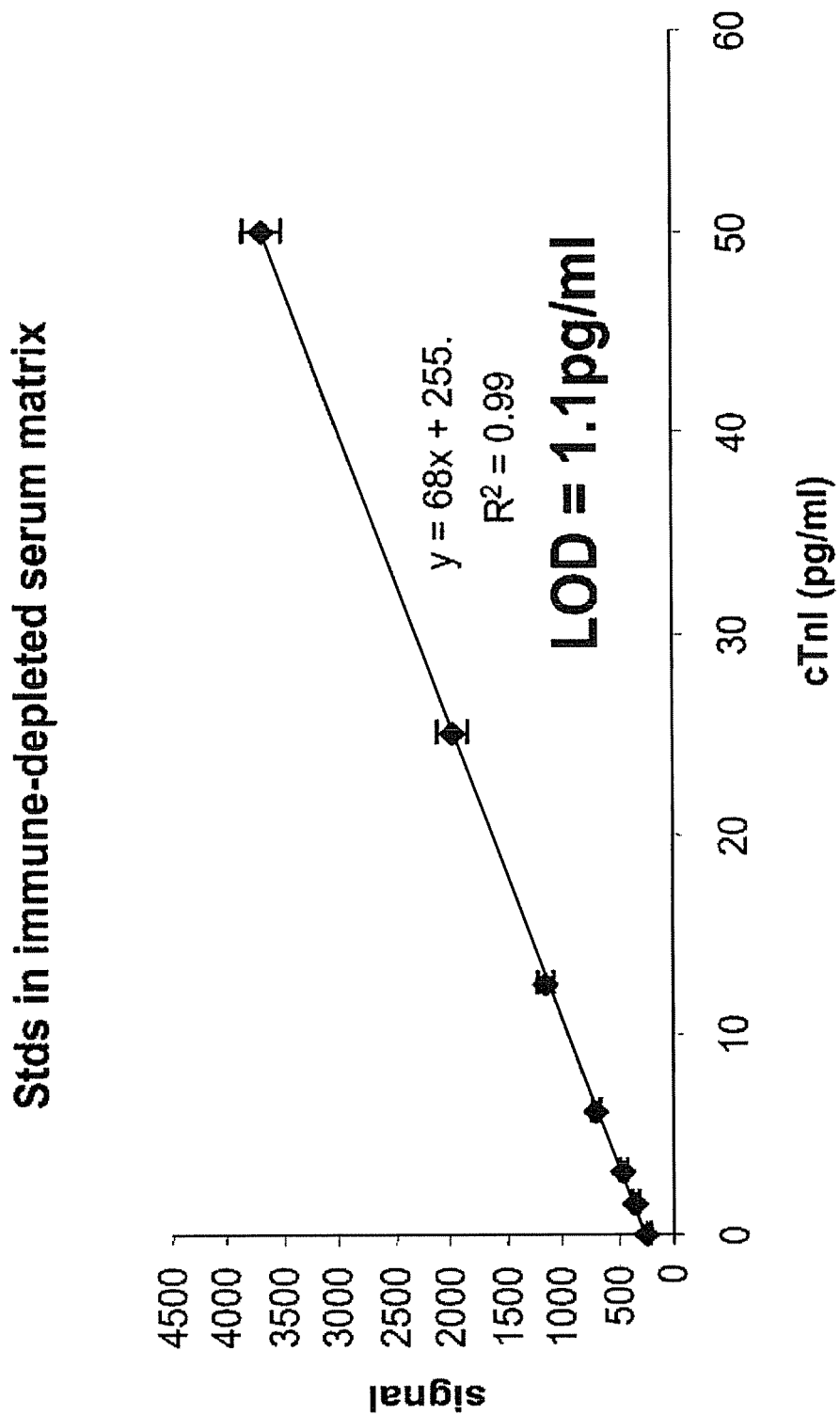
FIG. 4. Linearized standard curve for the range concentrations of cTnI.

In some embodiments, the optics of the electromagnetic radiation source and the optics of the detector are arranged in a confocal optical arrangement. In such an arrangement, the electromagnetic radiation source 301 and the detector 309 are aligned on the same focal plane. The confocal arrangement renders the analyzer more robust because the electromagnetic radiation source 301 and the detector optics 309 do not need to be realigned if the analyzer system is moved. This arrangement also makes the use of the analyzer more simplified because it eliminates the need to realign the components of the analyzer system. The confocal arrangement for the analyzer 300 (FIG. 1A) and the analyzer 355 (FIG. 1B) are shown in FIGS. 3A and 3B respectively. FIG. 3A shows that the beam 311 from an electromagnetic radiation source 301 is focused by the microscope objective 315 to form one interrogation space 314 (FIG. 2A) within the capillary flow cell 313. A dichroic mirror 316, which reflects laser light but passes fluorescent light, is used to separate the fluorescent light from the laser light. Filter 317 that is positioned in front of the detector eliminates any non-fluorescent light at the detector. In some embodiments, an analyzer system configured in a confocal arrangement can comprise two or more interrogations spaces. Such a method has been previously disclosed and is incorporated by reference from previous U.S. patent application Ser. No. 11/048,660.

The laser can be a tunable dye laser, such as a helium-neon laser. The laser can be set to emit a wavelength of 632.8 nm. Alternatively, the wavelength of the laser can be set to emit a wavelength of 543.5 μm or 1523 nm. Alternatively, the electromagnetic laser can be an argon ion laser. In such an embodiment, the argon ion laser can be operated as a continuous gas laser at about 25 different wavelengths in the visible spectrum, the wavelength set between 408.9 and 686.1 nm but at its optimum performance set between 488 and 514.5 mL 1. Electromagnetic Radiation Source In some embodiments of the analyzer system a chemiluminescent label may be used. In such an embodiment, it may not be necessary to utilize an EM source for detection of the particle. In another embodiment, the extrinsic label or intrinsic characteristic of the particle is a light-interacting label or characteristic, such as a fluorescent label or a light-scattering label. In such an embodiment, a source of EM radiation is used to illuminate the label and/or the particle. EM radiation sources for excitation of fluorescent labels are preferred.

In some embodiments, the analyzer system consists of an electromagnetic radiation source 301. Any number of radiation sources may be used in any one analyzer system 300 without departing from the scope of the invention. Multiple sources of electromagnetic radiation have been previously disclosed and are incorporated by reference from previous U.S. patent application Ser. No. 11/048,660. In some embodiments, all the continuous wave electromagnetic (EM) radiation sources emit electromagnetic radiation at the same wavelengths. In other embodiments, different sources emit different wavelengths of EM radiation.

In one embodiment, the EM source(s) 301, 351, 352 are continuous wave lasers producing wavelengths of between 200 nm and 1000 nm. Such EM sources have the advantage of being small, durable and relatively inexpensive. In addition, they generally have the capacity to generate larger fluorescent signals than other light sources. Specific examples of suitable continuous wave EM sources include, but are not limited to: lasers of the argon, krypton, helium-neon, helium-cadmium types, as well as, tunable diode lasers (red to infrared regions), each with the possibility of frequency doubling. The lasers provide continuous illumination with no accessory electronic or mechanical devices, such as shutters, to interrupt their illumination. In an embodiment where a continuous wave laser is used, an electromagnetic radiation source of 3 mW may be of sufficient energy to excite a fluorescent label. A beam from a continuous wave laser of such energy output may be between 2 to 5 μm in diameter. The time of exposure of the particle to laser beam in order to be exposed to 3 mW may be a time period of about 1 msec. In alternate embodiments, the time of exposure to the laser beam may be equal to or less than about 500 μsec. In an alternate embodiment, the time of exposure may be equal to or less than about 100 μsec. In an alternate embodiment, the time of exposure may be equal to or less than about 50 μsec. In an alternate embodiment, the time of exposure may be equal to or less than about 10 μsec.

LEDs are another low-cost, high reliability illumination source. Recent advances in ultra-bright LEDs and dyes with high absorption cross-section and quantum yield support the applicability of LEDs to single particle detection. Such lasers could be used alone or in combination with other light sources such as mercury arc lamps, elemental arc lamps, halogen lamps, arc discharges, plasma discharges, light-emitting diodes, or combination of these.

In other embodiments, the EM source could be in the form of a pulse wave laser. In such an embodiment, the pulse size of the laser is an important factor. In such an embodiment, the size, focus spot, and the total energy emitted by the laser is important and must be of sufficient energy as to be able to excite the fluorescent label. When a pulse laser is used, a pulse of longer duration may be required. In some embodiments a laser pulse of 2 nanoseconds may be used. In some embodiments a laser pulse of 5 nanoseconds may be used. In some embodiments a pulse of between 2 to 5 nanoseconds may be used.

The optimal laser intensity depends on the photo bleaching characteristics of the single dyes and the length of time required to traverse the interrogation space (including the speed of the particle, the distance between interrogation spaces if more than one is used and the size of the interrogation space(s)). To obtain a maximal signal, it is desirable to illuminate the sample at the highest intensity which will not result in photo bleaching a high percentage of the dyes. The preferred intensity is one such that no more that 5% of the dyes are bleached by the time the particle has traversed the interrogation space.

The power of the laser is set depending on the type of dye molecules that need to be stimulated and the length of time the dye molecules are stimulated, and/or the speed with which the dye molecules pass through the capillary flow cell. Laser power is defined as the rate at which energy is delivered by the beam and is measured in units of Joules/second, or Watts. It will be appreciated that the greater the power output of the laser, the shorter the time that the laser illuminates the particle may be, while providing a constant amount of energy to the interrogation space while the particle is passing through the space. Thus, in some embodiments, the combination of laser power and time of illumination is such that the total energy received by the interrogation space during the time of illumination is more than about 0.1, 0.5, 1, 2, 3, 4, 5, 6, 7, 8, 9, 10, 12, 15, 20, 25, 30, 35, 40, 45, 50, 60, 70, 80, 90, or 100 microJoule. In some embodiments, the combination of laser power and time of illumination is such that the total energy received by the interrogation space during the time of illumination is less than about 0.5, 1, 2, 3, 4, 5, 6, 7, 8, 9, 10, 12, 15, 20, 25, 30, 35, 40, 45, 50, 60, 70, 80, 90, 100, or 110 microJoule. In some embodiments, the combination of laser power and time of illumination is such that the total energy received by the interrogation space during the time of illumination is between about 0.1 and 100 microJoule. In some embodiments, the combination of laser power and time of illumination is such that the total energy received by the interrogation space during the time of illumination is between about 1 and 100 microJoule. In some embodiments, the combination of laser power and time of illumination is such that the total energy received by the interrogation space during the time of illumination is between about 1 and 50 microJoule. In some embodiments, the combination of laser power and time of illumination is such that the total energy received by the interrogation space during the time of illumination is between about 2 and 50 microJoule. In some embodiments, the combination of laser power and time of illumination is such that the total energy received by the interrogation space during the time of illumination is between about 3 and 60 microJoule. In some embodiments, the combination of laser power and time of illumination is such that the total energy received by the interrogation space during the time of illumination is between about 3 and 50 microJoule. In some embodiments, the combination of laser power and time of illumination is such that the total energy received by the interrogation space during the time of illumination is between about 3 and 40 microJoule. In some embodiments the combination of laser power and time of illumination is such that the total energy received by the interrogation space during the time of illumination is between about 3 and 30 microJoule. In some embodiments, the combination of laser power and time of illumination is such that the total energy received by the interrogation space during the time of illumination is about 1 microJoule. In some embodiments, the combination of laser power and time of illumination is such that the total energy received by the interrogation space during the time of illumination is about 3 microJoule. In some embodiments, the combination of laser power and time of illumination is such that the total energy received by the interrogation space during the time of illumination is about 5 microJoule. In some embodiments, the combination of laser power and time of illumination is such that the total energy received by the interrogation space during the time of illumination is about 10 microJoule. In some embodiments, the combination of laser power and time of illumination is such that the total energy received by the interrogation space during the time of illumination is about 15 microJoule. In some embodiments, the combination of laser power and time of illumination is such that the total energy received by the interrogation space during the time of illumination is about 20 microJoule. In some embodiments, the combination of laser power and time of illumination is such that the total energy received by the interrogation space during the time of illumination is about 30 microJoule. In some embodiments, the combination of laser power and time of illumination is such that the total energy received by the interrogation space during the time of illumination is about 40 microJoule. In some embodiments, the combination of laser power and time of illumination is such that the total energy received by the interrogation space during the time of illumination is about 50 microJoule. In some embodiments, the combination of laser power and time of illumination is such that the total energy received by the interrogation space during the time of illumination is about 60 microJoule. In some embodiments, the combination of laser power and time of illumination is such that the total energy received by the interrogation space during the time of illumination is about 70 microJoule. In some embodiments, the combination of laser power and time of illumination is such that the total energy received by the interrogation space during the time of illumination is about 80 microJoule. In some embodiments, the combination of laser power and time of illumination is such that the total energy received by the interrogation space during the time of illumination is about 90 microJoule. In some embodiments, the combination of laser power and time of illumination is such that the total energy received by the interrogation space during the time of illumination is about 100 microJoule.

In some embodiments, the laser power output is set to at least about 1 mW, 2 mW, 3 mW, 4 mW, 5 mW, 6, mw, 7 mW, 8 mW, 9 mW, 10 mW, 13 mW, 15 mW, 20 mW, 25 mW, 30 mW, 40 mW, 50 mW, 60 mW, 70 mW, 80 mW, 90 mW, 100 mW, or more than 100 mW. In some embodiments, the laser power output is set to at least about 1 mW. In some embodiments, the laser power output is set to at least about 3 mW. In some embodiments, the laser power output is set to at least about 5 mW. In some embodiments, the laser power output is set to at least about 10 mW. In some embodiments, the laser power output is set to at least about 15 mW. In some embodiments, the laser power output is set to at least about 20 mW. In some embodiments, the laser power output is set to at least about 30 mW. In some embodiments, the laser power output is set to at least about 40 mW. In some embodiments, the laser power output is set to at least about 50 mW. In some embodiments, the laser power output is set to at least about 60 mW. In some embodiments, the laser power output is set to at least about 90 mW.

The time that the laser illuminates the interrogation space can be set to no less than about 1, 2, 3, 4, 5, 10, 15, 20, 30, 40, 50, 60, 70, 80, 90, 100, 150, 200, 150, 300, 350, 400, 450, 500, 600, 700, 800, 900, or 1000 microseconds. The time that the laser illuminates the interrogation space can be set to no more than about 2, 3, 4, 5, 10, 15, 20, 30, 40, 50, 60, 70, 80, 90, 100, 150, 200, 150, 300, 350, 400, 450, 500, 600, 700, 800, 900, 1000, 1500, or 2000 microseconds. The time that the laser illuminates the interrogation space can be set between about 1 and 1000 microseconds. The time that the laser illuminates the interrogation space can be set between about 5 and 500 microseconds. The time that the laser illuminates the interrogation space can be set between about 5 and 100 microseconds. The time that the laser illuminates the interrogation space can be set between about 10 and 100 microseconds. The time that the laser illuminates the interrogation space can be set between about 10 and 50 microseconds. The time that the laser illuminates the interrogation space can be set between about 10 and 20 microseconds. The time that the laser illuminates the interrogation space can be set between about 5 and 50 microseconds. The time that the laser illuminates the interrogation space can be set between about 1 and 100 microseconds. In some embodiments, the time that the laser illuminates the interrogation space is about 1 microsecond. In some embodiments, the time that the laser illuminates the interrogation space is about 5 microseconds. In some embodiments, the time that the laser illuminates the interrogation space is about 10 microseconds. In some embodiments, the time that the laser illuminates the interrogation space is about 25 microseconds. In some embodiments, the time that the laser illuminates the interrogation space is about 50 microseconds. In some embodiments, the time that the laser illuminates the interrogation space is about 100 microseconds. In some embodiments, the time that the laser illuminates the interrogation space is about 250 microseconds. In some embodiments, the time that the laser illuminates the interrogation space is about 500 microseconds. In some embodiments, the time that the laser illuminates the interrogation space is about 1000 microseconds.

For example, the time that the laser illuminates the interrogation space can be set to 1 millisecond, 250 microseconds, 100 microseconds, 50 microseconds, 25 microseconds or 10 microseconds with a laser that provides a power output of 3 mW, 4 mw, 5 mW, or more than 5 mW. In some embodiments, a label is illuminated with a laser that provides a power output of 3 mW and illuminates the label for about 1000 microseconds. In other embodiments, a label is illuminated for less than 1000 milliseconds with a laser providing a power output of not more than about 20 mW. In other embodiments, the label is illuminated with a laser power output of 20 mW for less than or equal to about 250 microseconds. In some embodiments, the label is illuminated with a laser power output of about 5 mW for less than or equal to about 1000 microseconds.

2. Capillary Flow Cell

The capillary flow cell is fluidly connected to the sample system. In one embodiment, the interrogation space 314 of an analyzer system, is determined by the cross sectional area of the corresponding beam 311 and by a segment of the beam within the field of view of the detector 309. In one embodiment of the analyzer system, the interrogation space 314 has a volume, as defined herein, of between about between about 0.01 and 500 pL, or between about 0.01 pL and 100 pL, or between about 0.01 pL and 10 pL, or between about 0.01 pL and 1 pL, or between about 0.01 pL and 0.5 pL, or between about 0.02 pL and about 300 pL, or between about 0.02 pL and about 50 pL or between about 0.02 pL and about 5 pL or between about 0.02 pL and about 0.5 pL or between about 0.02 pL and about 2 pL, or between about 0.05 pL and about 50 pL, or between about 0.05 pL and about 5 pL, or between about 0.05 pL and about 0.5 pL, or between about 0.05 pL and about 0.2 pL, or between about 0.1 pL and about 25 pL. In some embodiments, the interrogation space has a volume between about 0.01 pL and 10 pL. In some embodiments, the interrogation space 314 has a volume between about 0.01 pL and 1 pL. In some embodiments, the interrogation space 314 has a volume between about 0.02 pL and about 5 pL. In some embodiments, the interrogation space 314 has a volume between about 0.02 pL and about 0.5 pL. In some embodiments, the interrogation space 314 has a volume between about 0.05 pL and about 0.2 pL. In some embodiments, the interrogation space 314 has a volume of about 0.1 pL. Other useful interrogation space volumes are as described herein. It should be understood by one skilled in the art that the interrogation space 314 can be selected for maximum performance of the analyzer. Although very small interrogation spaces have been shown to minimize the background noise, large interrogation spaces have the advantage that low concentration samples can be analyzed in a reasonable amount of time. In embodiments in which two interrogation spaces 370 and 371 are used, volumes such as those described herein for a single interrogation space 314 may be used.

In one embodiment of the present invention, the interrogation spaces are large enough to allow for detection of particles at concentrations ranging from about 1000 femtomolar (fM) to about 1 zeptomolar (zM). In one embodiment of the present invention, the interrogation spaces are large enough to allow for detection of particles at concentrations ranging from about 1000 fM to about 1 attomolar (aM). In one embodiment of the present invention, the interrogation spaces are large enough to allow for detection of particles at concentrations ranging from about 10 fM to about 1 attomolar (aM). In many cases, the large interrogation spaces allow for the detection of particles at concentrations of less than about 1 fM without additional pre-concentration devices or techniques. One skilled in the art will recognize that the most appropriate interrogation space size depends on the brightness of the particles to be detected, the level of background signal, and the concentration of the sample to be analyzed.

The size of the interrogation space 314 can be limited by adjusting the optics of the analyzer. In one embodiment, the diameter of the beam 311 can be adjusted to vary the volume of the interrogation space 314. In another embodiment, the field of view of the detector 309 can be varied. Thus, the source 301 and the detector 309 can be adjusted so that single particles will be illuminated and detected within the interrogation space 314. In another embodiment, the width of aperture 306 (FIG. 1A) that determine the field of view of the detector 309 is variable. This configuration allows for altering the interrogation space, in near real time, to compensate for more or less concentrated samples, ensuring a low probability of two or more particles simultaneously being within an interrogation space. Similar alterations for two or more interrogation spaces, 370 and 371, may performed.

In another embodiment, the interrogation space can be defined through the use of a calibration sample of known concentration that is passed through the capillary flow cell prior to the actual sample being tested. When only one single particle is detected at a time in the calibration sample as the sample is passing through the capillary flow cell, the depth of focus together with the diameter of the beam of the electromagnetic radiation source determines the size of the interrogation space in the capillary flow cell.

Figure 2B:
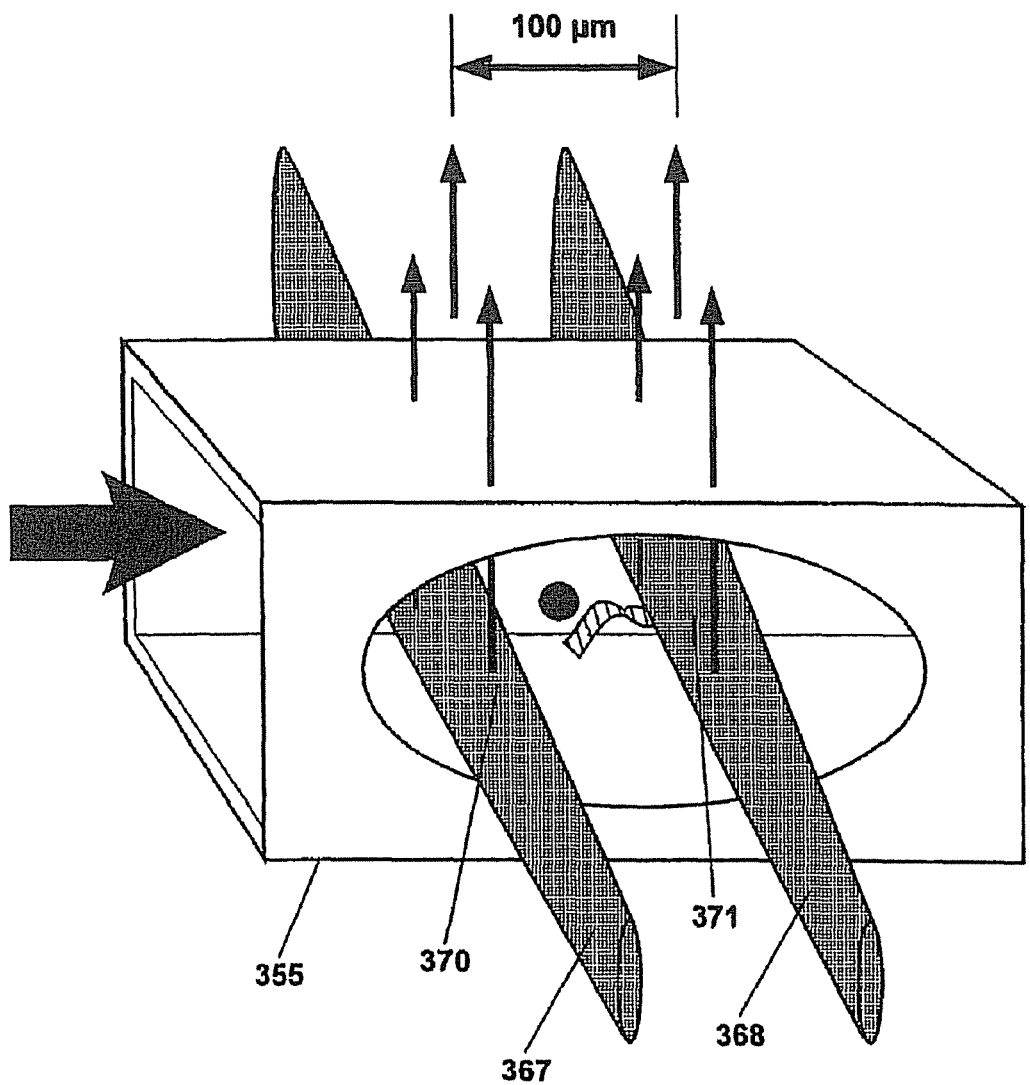

Physical constraints to the interrogation spaces can also be provided by a solid wall. In one embodiment, the wall is one or more of the walls of a flow cell 313 (FIG. 2A), when the sample fluid is contained within a capillary. In one embodiment, the cell is made of glass, but other substances transparent to light in the range of about 200 to about 1,000 nm or higher, such as quartz, fused silica, and organic materials such as Teflon, nylon, plastics, such as polyvinylchloride, polystyrene, and polyethylene, or any combination thereof, may be used without departing from the scope of the present invention. Although other cross-sectional shapes (e.g., rectangular, cylindrical) may be used without departing from the scope of the present invention, in one embodiment the capillary flow cell 313 has a square cross section. In another embodiment, the interrogation space may be defined at least in part by a channel (not shown) etched into a chip (not shown). Similar considerations apply to embodiments in which two interrogation spaces are used (370 and 371 in FIG. 2B).

The interrogation space is bathed in a fluid. In one embodiment, the fluid is aqueous. In other embodiments, the fluid is non-aqueous or a combination of aqueous and non-aqueous fluids. In addition the fluid may contain agents to adjust pH, ionic composition, or sieving agents, such as soluble macroparticles or polymers or gels. It is contemplated that valves or other devices may be present between the interrogation spaces to temporarily disrupt the fluid connection. Interrogation spaces temporarily disrupted are considered to be connected by fluid.

In another embodiment of the invention, an interrogation space is the single interrogation space present within the flow cell 313 which is constrained by the size of a laminar flow of the sample material within a diluent volume, also called sheath flow. In these and other embodiments, the interrogation space can be defined by sheath flow alone or in combination with the dimensions of the illumination source or the field of view of the detector. Sheath flow can be configured in numerous ways, including: The sample material is the interior material in a concentric laminar flow, with the diluent volume in the exterior; the diluent volume is on one side of the sample volume; the diluent volume is on two sides of the sample material; the diluent volume is on multiple sides of the sample material, but not enclosing the sample material completely; the diluent volume completely surrounds the sample material; the diluent volume completely surrounds the sample material concentrically; the sample material is the interior material in a discontinuous series of drops and the diluent volume completely surrounds each drop of sample material.

In some embodiments, single molecule detectors of the invention comprise no more than one interrogation space. In some embodiments, multiple interrogation spaces are used. Multiple interrogation spaces have been previously disclosed and are incorporated by reference from U.S. patent application Ser. No. 11/048,660. One skilled in the art will recognize that in some cases the analyzer will contain 2, 3, 4, 5, 6 or more distinct interrogation spaces.

3. Motive Force

In one embodiment of the analyzer system, the particles are moved through the interrogation space by a motive force. In some embodiments, the motive force for moving particles is pressure. In some embodiments, the pressure is supplied by a pump, and air pressure source, a vacuum source, a centrifuge, or a combination thereof. In some embodiments, the motive force for moving particles is an electrokinetic force. The use of an electrokinetic force as a motive force has been previously disclosed in a prior application and is incorporated by reference from U.S. patent application Ser. No. 11/048,660.

In one embodiment, pressure can be used as a motive force to move particles through the interrogation space of the capillary flow cell. In a further embodiment, pressure is supplied to move the sample by means of a pump. Suitable pumps are known in the art. In one embodiment, pumps manufactured for HPLC applications, such as those made by Scivax, Inc. can be used as a motive force. In other embodiments, pumps manufactured for microfluidics applications can be used when smaller volumes of sample are being pumped. Such pumps are described in U.S. Pat. Nos. 5,094,594, 5,730,187, 6,033,628, and 6,533,553, which discloses devices which can pump fluid volumes in the nanoliter or picoliter range. Preferably all materials within the pump that come into contact with sample are made of highly inert materials, e.g., polyetheretherketone (PEEK), fused silica, or sapphire.

A motive force is necessary to move the sample through the capillary flow cell to push the sample through the interrogation space for analysis. A motive force is also required to push a flushing sample through the capillary flow cell after the sample has been passed through. A motive force is also required to push the sample back out into a sample recovery vessel, when sample recovery is employed. Standard pumps come in a variety of sizes, and the proper size may be chosen to suit the anticipated sample size and flow requirements. In some embodiments, separate pumps are used for sample analysis and for flushing of the system. The analysis pump may have a capacity of approximately 0.000001 mL to approximately 10 mL, or approximately 0.001 mL to approximately 1 mL, or approximately 0.01 mL to approximately 0.2 mL, or approximately 0.005, 0.01, 0.05, 0.1, or 0.5 mL. Flush pumps may be of larger capacity than analysis pumps. Flush pumps may have a volume of about 0.01 mL to about 20 mL, or about 0.1 mL to about 10 mL, or about 0.1 mL to about 2 mL, or about or about 0.05, 0.1, 0.5, 1, 5, or 10 mL. These pump sizes are illustrative only, and those of skill in the art will appreciate that the pump size may be chosen according to the application, sample size, viscosity of fluid to be pumped, tubing dimensions, rate of flow, temperature, and other factors well known in the art. In some embodiments, pumps of the system are driven by stepper motors, which are easy to control very accurately with a microprocessor.

In preferred embodiments, the flush and analysis pumps are used in series, with special check valves to control the direction of flow. The plumbing is designed so that when the analysis pump draws up the maximum sample, the sample does not reach the pump itself. This is accomplished by choosing the ID and length of the tubing between the analysis pump and the analysis capillary such that the tubing volume is greater than the stroke volume of the analysis pump.

4. Detectors

In one embodiment, light (e.g., light in the ultra-violet, visible or infrared range) emitted by a fluorescent label after exposure to electromagnetic radiation is detected. The detector 309 (FIG. 1A), or detectors (364, 365, FIG. 1B), is capable of capturing the amplitude and duration of photon bursts from a fluorescent moiety, and further converting the amplitude and duration of the photon burst to electrical signals. Detection devices such as CCD cameras, video input module cameras, and Streak cameras can be used to produce images with contiguous signals. In another embodiment, devices such as a bolometer, a photodiode, a photodiode array, avalanche photodiodes, and photomultipliers which produce sequential signals may be used. Any combination of the aforementioned detectors may also be used. In one embodiment, avalanche photodiodes are used for detecting photons.

Using specific optics between an interrogation space 314 (FIG. 2A) and its corresponding detector 309 (FIG. 1A), several distinct characteristics of the emitted electromagnetic radiation can be detected including: emission wavelength, emission intensity, burst size, burst duration, and fluorescence polarization. In some embodiments, the detector 309 is a photodiode that is used in reverse bias. A photodiode set in reverse bias usually has an extremely high resistance. This resistance is reduced when light of an appropriate frequency shines on the P/N junction. Hence, a reverse biased diode can be used as a detector by monitoring the current running through it. Circuits based on this effect are more sensitive to light than ones based on zero bias.

In one embodiment of the analyzer system, the photodiode can be an avalanche photodiode, which can be operated with much higher reverse bias than conventional photodiodes, thus allowing each photo-generated carrier to be multiplied by avalanche breakdown, resulting in internal gain within the photodiode, which increases the effective responsiveness (sensitivity) of the device. The choice of photodiode is determined by the energy or emission wavelength emitted by the fluorescently labeled particle. In some embodiments, the photodiode is a silicon photodiode that detects energy in the range of 190-1100 nm; in another embodiment the photodiode is a germanium photodiode that detects energy in the range of 800-1700 nm; in another embodiment the photodiode is an indium gallium arsenide photodiode that detects energy in the range of 800-2600 nm; and in yet other embodiments, the photodiode is a lead sulfide photodiode that detects energy in the range of between less than 1000 nm to 3500 mm. In some embodiments, the avalanche photodiode is a single-photon detector designed to detect energy in the 400 nm to 1100 nm wavelength range. Single photon detectors are commercially available (for example Perkin Elmer, Wellesley, Mass.).

In some embodiments the detector is a avalanche photodiode detector that detects energy between 300 nm and 1700 nm. In one embodiment, silicon avalanche photodiodes can be used to detect wavelengths between 300 nm and 1100 nm. Indium gallium arsenic photodiodes can be used to detect wavelengths between 900 nm and 1700 mm. In some embodiments, an analyzer system can comprise at least one detector; in other embodiments, the analyzer system can comprise at least two detectors, and each detector can be chosen and configured to detect light energy at a specific wavelength range. For example, two separate detectors can be used to detect particles that have been tagged with different labels, which upon excitation with an EM source, will emit photons with energy in different spectra. In one embodiment, an analyzer system can comprise a first detector that can detect fluorescent energy in the range of 450-700 nm such as that emitted by a green dye (e.g. Alexa 546); and a second detector that can detect fluorescent energy in the range of 620-780 nm such as that emitted by a far-red dye (e.g. Alexa 647). Detectors for detecting fluorescent energy in the range of 400-600 nm such as that emitted by blue dyes (e.g. Hoechst 33342), and for detecting energy in the range of 560-700 nm such as that emitted by red dyes (Alexa 546 and Cy3) can also be used.

A system comprising two or more detectors can be used to detect individual particles that are each tagged with two or more labels that emit light in different spectra. For example, two different detectors can detect an antibody that has been tagged with two different dye labels. Alternatively, an analyzer system comprising two detectors can be used to detect particles of different types, each type being tagged with a different dye molecules, or with a mixture of two or more dye molecules. For example, two different detectors can be used to detect two different types of antibodies that recognize two different proteins, each type being tagged with a different dye label or with a mixture of two or more dye label molecules. By varying the proportion of the two or more dye label molecules, two or more different particle types can be individually detected using two detectors. It is understood that three or more detectors can be used without departing from the scope of the invention.

It should be understood by one skilled in the art that one or more detectors can be configured at each interrogation space, whether one or more interrogation spaces are defined within a flow cell, and that each detector may be configured to detect any of the characteristics of the emitted electromagnetic radiation listed above. The use of multiple detectors, e.g., for multiple interrogation spaces, has been previously disclosed in a prior application and is incorporated by reference here from U.S. patent application Ser. No. 11/048,660. Once a particle is labeled to render it detectable (or if the particle possesses an intrinsic characteristic rendering it detectable), any suitable detection mechanism known in the art may be used without departing from the scope of the present invention, for example a CCD camera, a video input module camera, a Streak camera, a bolometer, a photodiode, a photodiode array, avalanche photodiodes, and photomultipliers producing sequential signals, and combinations thereof. Different characteristics of the electromagnetic radiation may be detected including: emission wavelength, emission intensity, burst size, burst duration, fluorescence polarization, and any combination thereof.

C. Sampling System

In a further embodiment, the analyzer system may include a sampling system to prepare the sample for introduction into the analyzer system. The sampling system included is capable of automatically sampling a plurality of samples and providing a fluid communication between a sample container and a first interrogation space.

In some embodiments, the analyzer system of the invention includes a sampling system for introducing an aliquot of a sample into the single particle analyzer for analysis. Any mechanism that can introduce a sample may be used. Samples can be drawn up using either a vacuum suction created by a pump or by pressure applied to the sample that would push liquid into the tube, or by any other mechanism that serves to introduce the sample into the sampling tube. Generally, but not necessarily, the sampling system introduces a sample of known sample volume into the single particle analyzer; in some embodiments where the presence or absence of a particle or particles is detected, precise knowledge of the sample size is not critical. In preferred embodiments the sampling system provides automated sampling for a single sample or a plurality of samples. In embodiments where a sample of known volume is introduced into the system, the sampling system provides a sample for analysis of more than about 0.0001, 0.001, 0.01, 0.1, 1, 2, 5, 10, 20, 30, 40, 50, 60, 70, 80, 90, 100, 150, 200, 500, 1000, 1500, or 2000 µl. In some embodiments the sampling system provides a sample for analysis of less than about 2000, 1000, 500, 200, 100, 90, 80, 70, 60, 50, 40, 30, 20, 10, 5, 2, 1, 0.1, 0.01, or 0.001 µl. In some embodiments the sampling system provides a sample for analysis of between about 0.01 and 1500 µl, or about 0.1 and 1000 µl, or about 1 and 500 µl, or about 1 and 100 µl, or about 1 and 50 µl, or about 1 and 20 µl. In some embodiments, the sampling system provides a sample for analysis between about 5 µl and 200 µl, or about 5 µl and about 1000 µl, or about 5 µl and 50 µl. In some embodiments, the sampling system provides a sample for analysis between about 10 µl and 200 µl, or between about 10 µl and 100 ul, or between about 1 0 µl and 50 µl. In some embodiments, the sampling system provides a sample for analysis between about 0.5 µl and about 50 µl.

In some embodiments, the sampling system provides a sample size that can be varied from sample to sample. In these embodiments, the sample size may be any one of the sample sizes described herein, and may be changed with every sample, or with sets of samples, as desired.

Sample volume accuracy, and sample to sample volume precision of the sampling system, is required for the analysis at hand. In some embodiments, the precision of the sampling volume is determined by the pumps used, typically represented by a CV of less than about 50, 40, 30, 20, 10, 5, 4, 3, 2, 1, 0.5, 0.1, 0.05, or 0.01% of sample volume. In some embodiments, the sample to sample precision of the sampling system is represented by a CV of less than about 50, 40, 30, 20, 10, 5, 4, 3, 2, 1, 0.5, 0.1, 0.05, or 0.01%. In some embodiments, the intra-assay precision of the sampling system is represented by a CV of less than about 10, 5, 1, 0.5, or 0.1%. In some embodiments, the intra-assay precision of the sampling system shows a CV of less than about 5%. In some embodiments, the interassay precision of the sampling system is represented by a CV of less than about 10, 5, or 1%. In some embodiments, the interassay precision of the sampling system shows a CV of less than about 5%.

In some embodiments, the sampling system provides low sample carryover, advantageous in that an additional wash step is not required between samples. Thus, in some embodiments, sample carryover is less than about 1, 0.5, 0.1, 0.05, 0.04, 0.03, 0.02, 0.01, 0.005, or 0.001%. In some embodiments, sample carryover is less than about 0.02%. In some embodiments, sample carryover is less than about 0.01%.

In some embodiments the sampler provides a sample loop. In these embodiments, multiple samples are drawn into tubing sequentially and each is separated from the others by a "plug" of buffer. The samples typically are read one after the other with no flushing in between. Flushing is done once at the end of the loop. In embodiments where a buffer "plug" is used, the plug may be recovered ejecting the buffer plug into a separate well of a microtiter plate.

The sampling system may be adapted for use with standard assay equipment, for example, a 96-well microtiter plate, or, preferably, a 384-well plate. In some embodiments the system includes a 96 well plate positioner and a mechanism to dip the sample tube into and out of the wells, e.g., a mechanism providing movement along the X, Y, and Z axes. In some embodiments, the sampling system provides multiple sampling tubes from which samples may be stored and extracted from, when testing is commenced. In some embodiments, all samples from the multiple tubes are analyzed on one detector.

In other embodiments, multiple single molecule detectors may be connected to the sample tubes. Samples may be prepared by steps that include operations performed on sample in the wells of the plate prior to sampling by the sampling system, or sample may be prepared within the analyzer system, or some combination of both.

D. Sample Preparation System

Sample preparation includes the steps necessary to prepare a raw sample for analysis. These steps can involve, by way of example, one or more steps of: separation steps such as centrifugation, filtration, distillation, chromatography; concentration, cell lysis, alteration of pH, addition of buffer, addition of diluents, addition of reagents, heating or cooling, addition of label, binding of label, cross-linking with illumination, separation of unbound label, inactivation and/or removal of interfering compounds and any other steps necessary for the sample to be prepared for analysis by the single particle analyzer. In some embodiments, blood is treated to separate out plasma or serum. Additional labeling, removal of unbound label, and/or dilution steps may also be performed on the serum or plasma sample.

In some embodiments, the analyzer system includes a sample preparation system that performs some or all of the processes needed to provide a sample ready for analysis by the single particle analyzer. This system may perform any or all of the steps listed above for sample preparation. In some embodiments samples are partially processed by the sample preparation system of the analyzer system. Thus, in some embodiments, a sample may be partially processed outside the analyzer system first. For example, the sample may be centrifuged first. The sample may then be partially processed inside the analyzer by a sample preparation system. Processing inside the analyzer includes labeling the sample, mixing the sample with a buffer and other processing steps that will be known to one in the art. In some embodiments, a blood sample is processed outside the analyzer system to provide a serum or plasma sample, which is introduced into the analyzer system and further processed by a sample preparation system to label the particle or particles of interest and, optionally, to remove unbound label. In other embodiments preparation of the sample can include immunodepletion of the sample to remove particles that are not of interest or to remove particles that can interfere with sample analysis. In yet other embodiments, the sample can be depleted of particles that can interfere with the analysis of the sample. For example, sample preparation can include the depletion of heterophilic antibodies, which are known to interfere with immunoassays that use non-human antibodies to directly or indirectly detect a particle of interest. Similarly, other proteins that interfere with measurements of the particles of interest can be removed from the sample using antibodies that recognize the interfering proteins.

In some embodiments, the sample can be subjected to solid phase extraction prior to being assayed and analyzed. For example, a serum sample that is assayed for cAMP can first be subjected to solid phase extraction using a c18 column to which it binds. Other proteins such as proteases, lipases and phosphatases are washed from the column, and the cAMP is eluted essentially free of proteins that can degrade or interfere with measurements of cAMP. Solid phase extraction can be used to remove the basic matrix of a sample, which can diminish the sensitivity of the assay. In yet other embodiments, the particles of interest present in a sample may be concentrated by drying or lyophilizing a sample and solubilizing the particles in a smaller volume than that of the original sample.

In some embodiments the analyzer system provides a sample preparation system that provides complete preparation of the sample to be analyzed on the system, such as complete preparation of a blood sample, a saliva sample, a urine sample, a cerebrospinal fluid sample, a lymph sample, a BAL sample, a biopsy sample, a forensic sample, a bioterrorism sample, and the like. In some embodiments the analyzer system provides a sample preparation system that provides some or all of the sample preparation. In some embodiments, the initial sample is a blood sample that is further processed by the analyzer system. In some embodiments, the sample is a serum or plasma sample that is further processed by the analyzer system. The serum or plasma sample may be further processed by, e.g., contacting with a label that binds to a particle or particles of interest; the sample may then be used with or without removal of unbound label.

In some embodiments, sample preparation is performed, either outside the analysis system or in the sample preparation component of the analysis system, on one or more microtiter plates, such as a 96-well plate. Reservoirs of reagents, buffers, and the like can be in intermittent fluid communication with the wells of the plate by means of tubing or other appropriate structures, as are well-known in the art. Samples may be prepared separately in 96 well plates or tubes. Sample isolation, label binding and, if necessary, label separation steps may be done on one plate. In some embodiments, prepared particles are then released from the plate and samples are moved into tubes for sampling into the sample analysis system. In some embodiments, all steps of the preparation of the sample are done on one plate and the analysis system acquires sample directly from the plate. Although this embodiment is described in terms of a 96-well plate, it will be appreciated that any vessel for containing one or more samples and suitable for preparation of sample may be used. For example, standard microtiter plates of 384 or 1536 wells may be used. More generally, in some embodiments, the sample preparation system is capable of holding and preparing more than about 5, 10, 20, 30, 40, 50, 60, 70, 80, 90, 100, 200, 300, 500, 1000, 5000, or 10,000 samples. In some embodiments, multiple samples may be sampled for analysis in multiple analyzer systems. Thus, in some embodiments, 2 samples, or more than about 2, 3, 4, 5, 7, 10, 15 20, 50, or 100 samples are sampled from the sample preparation system and run in parallel on multiple sample analyzer systems.

Microfluidics systems may also be used for sample preparation and as sample preparation systems that are part of analyzer systems, especially for samples suspected of containing concentrations of particles high enough that detection requires smaller samples. Principles and techniques of microfluidic manipulation are known in the art. See, e.g., U.S. Pat. Nos. 4,979,824; 5,770,029; 5,755,942; 5,746,901; 5,681, 751; 5,658,413; 5,653,939; 5,653,859; 5,645,702; 5,605,662; 5,571,410; 5,543,838; 5,480,614, 5,716,825; 5,603,351; 5,858,195; 5,863,801; 5,955,028; 5,989,402; 6,041,515; 6,071,478; 6355,420; 6,495,104; 6,386,219; 6,606,609; 6,802,342; 6,749,734; 6,623,613; 6,554,744; 6,361,671; 6,143,152; 6,132,580; 5,274,240; 6,689,323; 6,783,992; 6,537,437; 6,599,436; 6,811,668 and published PCT patent application no. WO9955461(A1). Samples may be prepared in series or in parallel, for use in a single or multiple analyzer systems.

Preferably, the sample comprises a buffer. The buffer may be mixed with the sample outside the analyzer system, or it may be provided by the sample preparation mechanism. While any suitable buffer can be used, the preferable buffer has low fluorescence background, is inert to the detectably labeled particle, can maintain the working pH and, in embodiments wherein the motive force is electrokinetic, has suitable ionic strength for electrophoresis. The buffer concentration can be any suitable concentration, such as in the range from about 1 to about 200 mM. Any buffer system may be used as long as it provides for solubility, function, and delectability of the molecules of interest. Preferably, for application using pumping, the buffer is selected from the group consisting of phosphate, glycine, acetate, citrate, acidulate, carbonate/bicarbonate, imidazole, triethanolamine, glycine amide, borate, MES, Bis-Tris, ADA, aces, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, and CABS. The buffer can also be selected from the group consisting of Gly-Gly, bicine, tricine, 2-morpholine ethanesulfonic acid (MES),4-morpholine propanesulfonic acid (MOPS) and 2-amino-2-methyl-1-propanol hydrochloride (AMP). A useful buffer is 2 mM Tris/borate at pH 8.1, but Tris/glycine and Tris/HCl are also acceptable. Other buffers are as described herein.

Buffers useful for electrophoresis are disclosed in a prior application and are incorporated by reference herein from U.S. patent application Ser. No. 11/048,660.

E. Sample Recovery

One highly useful feature of embodiments of the analyzers and analysis systems of the invention is that the sample can be analyzed without consuming it. This can be especially important when sample materials are limited. Recovering the sample also allows one to do other analyses or reanalyze it. The advantages of this feature for applications where sample size is limited and/or where the ability to reanalyze the sample is desirable, e.g., forensic, drug screening, and clinical diagnostic applications, will be apparent to those of skill in the art.

Thus, in some embodiments, the analyzer system of the invention further provides a sample recovery system for sample recovery after analysis. In these embodiments, the system includes mechanisms and methods by which the sample is drawn into the analyzer, analyzed and then returned, e.g., by the same path, to the sample holder, e.g., the sample tube. Because no sample is destroyed and because it does not enter any of the valves or other tubing, it remains uncontaminated. In addition, because all the materials in the sample path are highly inert, e.g., PEEK, fused silica, or sapphire, there is little contamination from the sample path. The use of the stepper motor controlled pumps (particularly the analysis pump) allows precise control of the volumes drawn up and pushed back out. This allows complete or nearly complete recovery of the sample with little if any dilution by the flush buffer. Thus, in some embodiments, more than about 50%, 60%, 70%, 80%, 85%, 90%, 95%, 96%, 97%, 98%, 99%, 99.5%, or 99.9% of the sample is recovered after analysis. In some embodiments, the recovered sample is undiluted. In some embodiments, the recovered sample is diluted less than about 1.5-fold, 1.4-fold, 1.3-fold, 1.2-fold, 1.1-fold, 1.05-fold, 1.01-fold, 1.005-fold, or 1.001-fold.

For sampling and/or sample recovery, any mechanism for transporting a liquid sample from a sample vessel to the analyzer may be used. In some embodiments the inlet end of the analysis capillary has attached a short length of tubing, e.g., PEEK tubing that can be dipped into a sample container, e.g. a test tube or sample well, or can be held above a waste container. When flushing, to clean the previous sample from the apparatus, this tube is positioned above the waste container to catch the flush waste. When drawing a sample in, the tube is put into the sample well or test tube. Typically the sample is drawn in quickly, and then pushed out slowly while observing particles within the sample. Alternatively, in some embodiments, the sample is drawn in slowly during at least part of the draw-in cycle; the sample may be analyzed while being slowly drawn in. This can be followed by a quick return of the sample and a quick flush. In some embodiments, the sample may be analyzed both on the inward (draw-in) and outward (pull out) cycle, which improves counting statistics, e.g., of small and dilute samples, as well as confirming results, and the like. If it is desired to save the sample, it can be pushed back out into the same sample well it came from, or to another. If saving the sample is not desired, the tubing is positioned over the waste container.

VI. Methods using Highly Sensitive Analysis of Molecules

The systems, system kits, and methods of the present invention make possible measurement of molecules in samples at concentrations far lower than previously measured. The high sensitivity of the instruments, kits, and methods of the invention allows the establishment of markers, e.g., biological markers, that have not previously been possible because of a lack of sensitivity of detection. The invention also includes the use of the compositions and methods described herein for the discovery of new markers.

There are numerous markers currently available which, while potentially of use in determining a biological state, are not currently of practical use because their lower ranges are unknown. In some cases, abnormally high levels of the marker are detectable by current methodologies, but normal ranges have not been established. In some cases, upper normal ranges of the marker are detectable, but not lower normal ranges, or levels below normal. In some cases, for example, markers specific to tumors, or markers of infection, any level of the marker indicates the potential presence of the biological state, and enhancing sensitivity of detection is an advantage for early diagnosis. In some cases, the rate of change, or lack of change, in the concentration of the marker over multiple timepoints provides the most useful information, but present methods of analysis do not permit determination of levels of the marker at timepoint sampling in the early stages of a condition, when it is typically at its most treatable. In many cases, the marker may be detected at clinically useful levels only through the use of cumbersome methods that are not practical or useful in a clinical setting, such as methods that require complex sample treatment and time-consuming analysis.

In addition, there are potential markers of biological states that exist in sufficiently low concentrations that their presence remains extremely difficult or impossible to detect by current methods.

The analytical methods and compositions of the present invention provide levels of sensitivity and precision that allow the detection of markers for biological states at concentrations at which the markers have been previously undetectable, thus allowing the "repurposing" of such markers from confirmatory markers, or markers useful only in limited research settings, to diagnostic, prognostic, treatment-directing, or other types of markers useful in clinical settings and/or in large-scale clinical settings such as clinical trials. Such methods allow, e.g., the determination of normal and abnormal ranges for such markers.

The markers thus repurposed can be used for, e.g., detection of normal state (normal ranges), detection of responder/non-responder (e.g., to a treatment, such as administration of a drug); early disease or pathological occurrence detection (e.g., detection of cancer in its earliest stages, early detection of cardiac ischemia); disease staging (e.g., cancer); disease monitoring (e.g., diabetes monitoring, monitoring for recurrence of cancer after treatment); study of disease mechanism; and study of treatment toxicity, such as toxicity of drug treatments (e.g., cardiotoxicity).

A. Methods

The invention thus provides methods and compositions for the sensitive detection of markers, and further methods of establishing values for normal and abnormal levels of the markers. In further embodiments, the invention provides methods of diagnosis, prognosis, and/or treatment selection based on values established for the markers. The invention also provides compositions for use in such methods, e.g., detection reagents for the ultrasensitive detection of markers.

In some embodiments, the invention provides a method of establishing a marker for a biological state, by establishing a range of concentrations for the marker in biological samples obtained from a first population by measuring the concentrations of the marker the biological samples by detecting single molecules of the marker (e.g., by detecting a label that has been attached to a single molecule of the marker). In some embodiments, the marker is a polypeptide or small molecule. The samples may be any sample type described herein, e.g., blood, plasma, or serum; or urine.

The method may utilize samples from a first population where the population is a population that does not exhibit the biological state. In the case where the biological state is a disease state, the first population may be a population that does not exhibit the disease, e.g., a "normal" population. In some embodiments the method may further comprise establishing a range of range of levels for the marker in biological samples obtained from a second population, where the members of the second population exhibit the biological state, by measuring the concentrations of the marker the biological samples by detecting single molecules of the marker. In some embodiments, e.g., cross-sectional studies, the first and second populations are different. In some embodiments, at least one member of the second population is a member of the first population, or at least one member of said the population is a member of the second population. In some embodiments, e.g., longitudinal studies, substantially all the members of the second population are members of the first population who have developed the biological state (e.g., a disease or pathological state).

The detecting of single molecules of the marker is performed using a method as described herein, e.g., a method with a limit of detection for said marker of less than about 1000, 100, 50, 20, 10, 5, 1, 0.5, 0.1, 0.05, 0.01, 0.005, or 0.001 femtomolar of the marker in the samples, by detecting single molecules of the marker.

The biological state may be a phenotypic state; a condition affecting the organism; a state of development; age; health; pathology; disease; disease process; disease staging; infection; toxicity; or response to chemical, environmental, or drug factors (such as drug response phenotyping, drug toxicity phenotyping, or drug effectiveness phenotyping).

In some embodiments, the biological state is a pathological state, including but not limited to inflammation, abnormal cell growth, and abnormal metabolic state. In some embodiments, the state is a disease state. Disease states include, but are not limited to, cancer, cardiovascular disease, inflammatory disease, autoimmune disease, neurological disease, infectious disease and pregnancy related disorders. In some embodiments the state is a disease stage state, e.g., a cancer disease stage state.

The methods may also be used for determination of a treatment response state. In some embodiments, the treatment is a drug treatment. The response may be a therapeutic effect or a side effect, e.g., an adverse effect. Markers for therapeutic effects will be based on the disease or condition treated by the drug. Markers for adverse effects typically will be based on the drug class and specific structure and mechanism of action and metabolism. A common adverse effect is drug toxicity. An example is cardiotoxicity, which can be monitored by the marker cardiac troponin. In some embodiments one or more markers for the disease state and one or more markers for one or more adverse effects of a drug are monitored, typically in a population that is receiving the drug. Samples may be taken at intervals and the respective values of the markers in the samples may be evaluated over time.

The detecting of single molecules of the marker may comprise labeling the marker with a label comprising a fluorescent moiety capable of emitting at least about 200 photons when simulated by a laser emitting light at the excitation wavelength of the moiety, where the laser is focused on a spot not less than about 5 microns in diameter that contains the moiety, and wherein the total energy directed at the spot by the laser is no more than about 3 microJoules. In some embodiments, the fluorescent moiety comprises a molecule that comprises at least one substituted indolium ring system in which the substituent on the 3-carbon of the indolium ring contains a chemically reactive group or a conjugated substance. In some embodiments, the fluorescent moiety may comprise a dye selected from the group consisting of AlexaFluor 488, AlexaFluor 532, AlexaFluor 647, AlexaFluor 680 or AlexaFluor 700. In some embodiments, the moiety comprises AlexaFluor 647. In some embodiments, the label further comprises a binding partner for the marker, e.g., an antibody specific for said marker, such as a polyclonal antibody or a monoclonal antibody. Binding partners for a variety of markers are described herein.

The method may further include establishing a threshold level for the marker based on the first range, or the first and second ranges, where the presence of marker in a biological sample from an individual at a level above or below the threshold level indicates an increased probability of the presence of the biological state in said individual. An example of a threshold determined for a normal population is the suggested threshold for cardiac troponin of greater than the 99th percentile value in a normal population. See Example 3. Other threshold levels may be determined empirically, i.e., based on data from the first and second populations regarding marker levels and the presence, absence, severity, rate of progression, rate of regression, and the like, of the biological state being monitored. It will be appreciated that threshold levels may be established at either end of a range, e.g., a minimum below which the concentration of the marker in a sample indicates an increased probability of a biological state, and/or a maximum above which the concentration of the marker in a sample indicates an increased probability of a biological state. In some embodiments, a risk stratification may be produced in which two or more ranges of marker concentrations correspond to two or more levels of risk. Other methods of analyzing data from two populations and for markers and producing clinically-relevant values for use by, e.g., physicians and other health care professionals, are well-known in the art.

For some biological markers, the presence of any marker at all is an indication of a disease or pathological state, and the threshold is essentially zero. An example is the use of prostate specific antigen (PSA) to monitor cancer recurrence after removal of the prostate gland. As PSA is produced only by the prostate gland, and as the prostate gland and all tumor are presumed to be removed, PSA after removal is zero. Appearance of PSA at any level signals a possible recurrence of the cancer, e.g., at a metastatic site. Thus, the more sensitive the method of detection, the earlier an intervention may be made should such recurrence occur.

Other evaluations of marker concentration may also be made, such as in a series of samples, where change in value, rate of change, spikes, decrease, and the like may all provide useful information for determination of a biological state. In addition, panels of markers may be used if it is found that more than one marker provides information regarding a biological state. If panels of markers are used, the markers may be measured separately in separate samples (e.g., aliquots of a common sample) or simultaneously by multiplexing. Examples of panels of markers and multiplexing are given in, e.g., U.S. patent application Ser. No. 11/048,660.

The establishment of such markers and, e.g., reference ranges for normal and/or abnormal states, allow for sensitive and precise determination of the biological state of an organism. Thus, in some embodiments, the invention provides a method for detecting the presence or absence of a biological state of an organism, comprising i) measuring the concentration of a marker in a biological sample from the organism, wherein said marker is a marker established through establishing a range of concentrations for said marker in biological samples obtained from a first population by measuring the concentrations of the marker the biological samples by detecting single molecules of the marker; and ii) determining the presence of absence of said biological state based on said concentration of said marker in said organism.

In some embodiments, the invention provides a method for detecting the presence or absence of a biological state in an organism, comprising i) measuring the concentrations of a marker in a plurality of biological samples from said organism, wherein said marker is a marker established through establishing a range of concentrations for said marker in biological samples obtained from a first population by measuring the concentrations of the marker the biological samples by detecting single molecules of the marker; and ii) determining the presence of absence of said biological state based on said concentrations of said marker in said plurality of samples. In some embodiments, the samples are of different types, e.g., are samples from different tissue types. In this case, the determining is based on a comparison of the concentrations of said marker in said different types of samples. More commonly, the samples are of the same type, and the samples are taken at intervals. The samples may be any sample type described herein, e.g., blood, plasma, or serum; or urine. Intervals between samples may be minutes, hours, days, weeks, months, or years. In an acute clinical setting, the intervals may be minutes or hours. In settings involving the monitoring of an individual, the intervals may be days, weeks, months, or years.

In many cases, the biological state whose presence or absence is to be detected is a disease phenotype. Thus, in one embodiment, a phenotypic state of interest is a clinically diagnosed disease state. Such disease states include, for example, cancer, cardiovascular disease, inflammatory disease, autoimmune disease, neurological disease, respiratory disease, infectious disease and pregnancy related disorders.

Cancer phenotypes are included in some aspects of the invention. Examples of cancer herein include, but are not limited to: breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, non-small cell lung carcinoma gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wili's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fingoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Cardiovascular disease may be included in other applications of the invention. Examples of cardiovascular disease include, but are not limited to, congestive heart failure, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, congestive heart failure, myocardial ischemia, myocardial infarction, cardiac tamponade, myocarditis, pericarditis, arrhythmogenic right ventricular dysplasia, hypertrophic cardiomyopathy, Williams syndrome, heart valve diseases, endocarditis, bacterial, pulmonary atresia, aortic valve stenosis, Raynaud's disease, Raynaud's disease, cholesterol embolism, Wallenberg syndrome, Hippel-Lindau disease, and telangiectasis.

Inflammatory disease and autoimmune disease may be included in other embodiments of the invention. Examples of inflammatory disease and autoimmune disease include, but are not limited to, rheumatoid arthritis, non-specific arthritis, inflammatory disease of the larynx, inflammatory bowel disorder, psoriasis, hypothyroidism (e.g., Hashimoto thyroidism), colitis, Type 1 diabetes, pelvic inflammatory disease, inflammatory disease of the central nervous system, temporal arteritis, polymyalgia rheumatica, ankylosing spondylitis, polyarteritis nodosa, Reiter's syndrome, scleroderma, systemic lupus and erythematosus.

The methods and compositions of the invention can also provide laboratory information about markers of infectious disease including markers of Adenovirus, Bordella pertussis, Chlamydia pneumoiea, Chlamydia trachomais, Cholera Toxin, Cholera Toxin β, Campylobacter jejuni, Cytomegalovirus, Diptheria Toxin, Epstein-Barr NA, Epstein-Barr EA, Epstein-Barr VCA, Helicobacter Pylori, Hepatitis B virus (HBV) Core, Hepatitis B virus (HBV) Envelope, Hepatitis B virus (HBV) Survace (Ay), Hepatitis C virus (HCV) Core, Hepatitis C virus (HCV) NS3, Hepatitis C virus (HCV) NS4, Hepatitis C virus (HCV) NS5, Hepititis A, Hepititis D, Hepatitis E virus (HEV) orf2 3 KD, Hepatitis E virus (HEV) orf2 6 KD, Hepatitis E virus (HEV) orf3 3 KD, Human immunodeficiency virus (HIV)-1 p24, Human immunodeficiency virus (HIV)-1 gp4 1, Human immunodeficiency virus (HIV)-1 gp120, Human papilloma virus (HPV), Herpes simplex virus HSV-1/2, Herpes simplex virus HSV-1 gD, Herpes simplex virus HSV-2 gG, Human T-cell leukemia virus (HTLV)-1/2, Influenza A, Influenza A H3N2, Influenza B, Leishmanina donovani, Lyme disease, Mumps, *M. pneumoniae*, M. teberculosis, Parainfluenza 1, Parainfluenza 2, Parainfluenza 3, Polio Virus, Respiratory syncytial virus (RSV), Rubella, Rubeola, Streptolysin O, Tetanus Toxin, *T. pallidum* 15 kd, T. pallidum p47, *T. cruzi, Toxoplasma*, and Varicella Zoater.

B. Exemplary Markers

The instruments, labels, and methods of the invention have been used to establish ranges for markers in, e.g., serum and urine, at levels 10- to 100-fold lower than previous levels, or lower. The markers are indicative of a wide variety of biological states, e.g., cardiac disease and cardiotoxicity (troponin), infection (TREM-1), inflammation and other conditions (LTE4, IL-6 and IL-8), asthma (LTE4), cancer (Akt1, TGF-beta, Fas ligand), and allograft rejection and degenerative disease (Fas ligand).

Markers include protein and non-protein markers. The markers are described briefly here and procedures and results given in the Examples.

1. Cardiac Damage

Cardiac troponin is an example of a marker that is currently detectable only in abnormally high amounts. Cardiac troponin is a marker of cardiac damage, useful in diagnosis, prognosis, and determination of method of treatment in a number of diseases and conditions, e.g., acute myocardial infarct. In addition, cardiac troponin is a useful marker of cardiotoxicity due to treatment, e.g., drug treatment.

The troponin complex in muscle consists of troponin I, C and T. Troponin C exists as two isoforms, one from cardiac and slow-twitch muscle and one from fast-twitch muscle; because it is found in virtually all striated muscle, its use as a specific marker is limited. In contrast, troponin I and T are expressed as different isoforms in slow-twitch, fast-twitch and cardiac muscle. The unique cardiac isoforms of troponin I and T allow them to be distinguished immunologically from the other troponins of skeletal muscle. Therefore, the release into the blood of cardiac troponin I and T is indicative of damage to cardiac muscle, and provides the basis for their use as diagnostic or prognostic markers, or to aid in determination of treatment.

Currently used markers for cardiac damage suffer disadvantages that limit their clinical usefulness. Cardiac enzyme assays have formed the basis for determining whether or not there is damage to the cardiac muscle. Unfortunately, the standard creatine kinase-MB (CK-MB) assay is not reliable in excluding infarction until 10 to 12 hours after the onset of chest pain. Earlier diagnosis would have very specific advantages with regard to fibrinolytic therapy and triage.

Because the level of troponin found in the circulation of healthy individuals is very low, and cardiac specific troponins do not arise from extra-cardiac sources, the troponins are very sensitive and specific markers of cardiac injury. In addition to cardiac infarct, a number of other conditions can cause damage to the heart muscle, and early detection of such damage would prove useful to clinicians. However, present methods of detection and quantitation of cardiac troponin do not possess sufficient sensitivity to detect the release of cardiac troponin into the blood until levels have reached abnormally high concentrations, e.g., 0.1 ng/ml or greater.

The methods and compositions of the invention thus include methods and compositions for the highly sensitive detection and quantitation of cardiac troponin, and compositions and methods for diagnosis, prognosis, and/or determination of treatment based on such highly sensitive detection and quantitation. A standard curve for cardiac troponin I was established with a limit of detection less than about 1 pg/l (Example 1). Levels of cardiac troponin I were established in normal individuals, and a threshold value at the $99^{th}$ percentile of normal established (Example 3). Serial samples from individuals who suffered acute myocardial infarct were analyzed, and time courses for cardiac troponin I concentrations, including deviations from baseline, were determined (Example 4). Thus, cardiac troponin I serves as an example of a marker that can be detected by the systems and methods of the invention at levels to provide diagnostic and prognostic information of use in clinical and research settings. See also U.S. patent application Ser. No. 11/784,213, entitled "Highly Sensitive System and Methods for Analysis of Troponin," filed on even date herewith, which is incorporated by reference herein in its entirety.

2. Infection

TREM-1 is a marker of bacterial or fungal infections. Assays of the invention suggest that TREM-1 may routinely be measured at a concentration of 100 fM

3. Cytokines

The normal level of many cytokines, chemokines and growth factors is not known primarily because of the inability of existing technology to detect levels that are below those found in samples from diseased patients. For example, the basal level of other cytokines such as IL-10, TNF-alpha, IL-4, IL-1beta, IL-2, IL-12 and IFN-gamma cannot be detected by routine assays that are performed in a clinical setting, whereas the analyzer systems of the invention can readily determine the level of these and other cytokines. Knowing the level of cytokines and growth factors aids clinicians with the diagnosis, prognosis and treatment of a variety of diseases including cancer, and respiratory, infectious, and cardiovascular diseases. Early cytokine detection to monitor normal and disease states in clinical specimens can be achieved using the analyzer systems of the invention to analyze samples such as plasma, serum, and urine as well as other fluid samples to provide for better translational medicine. For example, determining levels of cytokines for which a normal range of concentration is not known, would aid clinicians with diagnosis and treatment of the following conditions and diseases. Bone Morphogenetic Proteins would be useful to monitor the treatment for fractures, spinal fusions, orthopedic surgery, and oral surgery; Interleukin-10 (IL-10) would be useful for detecting and monitoring for the presence of cancers including non-Hodgkin's lymphoma, multiple myeloma, melanoma, and ovarian cancer, as well as for detecting and monitoring the effect of anti-inflammatory therapy, organ transplantation, immunodeficiencies, and parasitic infections; Interleukin-11 (IL-11) is useful for the detection and monitoring for the presence of cancers such as breast cancer; Interleukin-12 (IL-12) for cancer and HIV infections; TNFα, an inflammatory cytokine, alone or in combination with IL-6, can be used as a good predictor of sepsis, acute pancreatitis, tuberculosis, and autoimmune disease such as rheumatoid arthritis and lupus.

Alternatively, databases may already exist for normal and abnormal values but present methods may not be practical for screening individuals on a routine basis to determine with sufficient sensitivity whether the value of the individual for the marker is within the normal range. For example, most present methods for the determination of IL-6 concentration in a sample are capable of detecting IL-6 only down to a concentration of about 5 pg/ml; the normal range of IL-6 values is about 1 to about 10 pg/ml; hence, present methods are able to detect IL-6 only in the upper part of normal ranges. In contrast, the analyzers and analyzer systems of the invention allow the detection of IL-6 down to a concentration below about 0.1 pg/ml, or less than one-tenth of normal range values. The lower limit of quantitation (LLOQ) is about 0.01 pg/ml. Thus, the analyzers and analyzer systems of the invention allow a far broader and more nuanced database to be produced for a biomarker, e.g., for IL-6, and also allow screening for that biomarker both within and outside of the normal range, allowing earlier detection.

Thus, the analyzers and analyzer systems of the invention allow a far broader and more nuanced database to be produced for a biomarker, e.g., for IL-6, and also allow screening for that biomarker both within and outside of the normal range, allowing earlier detection of conditions in which IL-6 is implicated. IL-6-related disorders include but are not limited to sepsis, peripheral arterial disease, and chronic obstructive pulmonary disease. Interleukin-6 mediated inflammation is also the common causative factor and therapeutic target for atherosclerotic vascular disease and age-related disorders including osteoporosis and type 2 diabetes. In addition, IL-6 can be measured in combination with other cytokines, for example TNFα to diagnose additional diseases such as septic shock.

4. Inflammatory Markers

Other cytokines that can be useful in detecting early onset of inflammatory disease include markers and panels of markers of inflammation as described herein. Examples of cytokines that can be used to detect an inflammatory disorders are Leukotriene 4 (LTE4), which can be an early marker of asthma and TGFβ, which can be used to detect and monitor the status of inflammatory disorders including fibrosis, sclerosis. Some markers can be used to detect more than one disorder, for example TGFβ can also be used to detect the presence of cancer.

Leukotriene E4 Cysteinyl leukotrienes ($LTC_4$, $LTD_4$, $LTE_4$) play an important role in the pathogenesis of asthma. Leukotrienes are produced by mast cells, eosinophils, and other airway inflammatory cells and increase vascular permeability, constrict bronchial smooth muscle, and mediate bronchial hyperresponsiveness. Levels of urinary $LTE_4$, the stable metabolite of $LTC_4$ and $LTD_4$, are increased in children and adults with asthma compared with healthy controls and in asthmatics after bronchial challenge with antigen, after oral challenge with aspirin in aspirin sensitive asthmatic subjects, and during exercise induced bronchospasm. The importance of leukotrienes in the pathology of asthma has been further demonstrated in large clinical trials with agents that block the actions of leukotrienes. For example, montelukast, a potent leukotriene receptor antagonist taken orally once daily, significantly improves asthma control in both children (aged 2-14 years) and adults and attenuates exercise induced bronchoconstriction.

Activation of the leukotriene pathways is accompanied by rises in urinary levels of LTE4, and acute exacerbations of asthma are accompanied by increased levels of LTE4 in urine followed by a significant decrease during resolution. The degree of airflow limitation correlates with levels of urinary LTE4 during the exacerbation and follow up periods, thus indicating that the leukotriene pathway is activated during acute asthma. In addition, inhalation of bronchoconstricting doses of LTC4 or LTE4 alter urinary LTE4 excretion in a dose-dependent manner thus indicating that urinary LTE4 can be used as a marker of sulphidopeptide leukotriene synthesis in the lungs of patients with asthma.

The methods of the invention can be used to detect changes in LTE4 in biological samples such as urinary samples (Examples). Measurements of subnanogram levels of LTE4 can be useful as a references for detecting and monitoring sulphidopeptide leukotriene synthesis in the lungs of patients with chronic or acute asthma.

6. TGFβ

The methods of the invention can also be performed to detect the early onset of diseases for which TGFβ is a marker. Examples of TGFβ-related diseases include fibrotic diseases. Fibrosis refers to the excessive and persistent formation of scar tissue, which is responsible for morbidity and mortality associated with organ failure in a variety of chronic diseases affecting the lungs, kidneys, eyes, heart, liver, and skin. TGFβ is well known for its role as a mediator of chronic fibrotic effects. For example, TGFβ is implicated in promoting fibroblastic proliferation and matrix accumulation in fibrotic lung disease. Inhibition of TGFβ has been proposed as a potential therapeutic avenue for the management of lung fibrosis. TGFβ not only stimulates the synthesis of many extracellular matrix molecules, including fibronectin and type I collagen and their receptors, but also decreases matrix degradation via differential effects on the expression of proteases and their inhibitors, strongly promoting generation of extracellular matrix. Thus the analyzer systems of the invention can detect abnormal levels of TGFβ, e.g., associated with fibrotic diseases, including but not limited to idiopathic pulmonary fibrosis, diabetic nephropathy, progressive nephropathies including glomerulosclerosis and IgA nephropathy (causes of kidney failure and the need for dialysis and retransplant); diabetic retinopathy and advanced macular degeneration (fibrotic diseases of the eye and leading causes of blindness); cirrhosis and biliary atresia (leading causes of liver fibrosis and failure); and congestive heart failure, myocardiopathy associated with progressive fibrosis in Chagas disease; lung fibrosis; and scleroderma.

TGFβ is also a marker for cancers including prostate cancer, cervical cancer, lung carcinoma, and Hodgkin's disease. Plasma levels of TGFβ in patients with lung cancer are often elevated. It has been shown that in patients with an elevated plasma TGF beta 1 level at diagnosis, monitoring this level may be useful in detecting both disease persistence and recurrence after radiotherapy.

Transforming growth factor-beta (TGF-beta) is a multipotent growth factor affecting development, homeostasis, and tissue repair. In addition, increased expression of TGF-beta has been reported in different malignancies, suggesting a role for this growth factor in tumorigenesis. In particular, it has been demonstrated that the presence of TGF-beta in the endothelial and perivascular layers of small vessels in the tumor stroma of osteosarcomas suggests an angiogenic activity of this growth factor, and that increased expression of TGF-beta isoforms have been suggested to play a role in the progression of osteosarcoma (Kloen et al., Cancer, 80:2230-9 (1997)). TGFβ is one of the few known proteins that can inhibit cell growth, however, although the notion is controversial, some researchers believe that some human malignancies such as breast cancer subvert TGFβ for their own purposes. In a paradox that is not understood, these cancers make TGFβ and steadily increase its expression until it becomes a marker of advancing metastasis and decreased survival. For example, levels of plasma TGFβ are markedly elevated in men with prostate cancer metastatic to regional lymph nodes and bone. In men without clinical or pathologic evidence of metastases, the preoperative plasma TGF-β level is a strong predictor of biochemical progression after surgery, presumably because of an association with occult metastatic disease present at the time of radical prostatectomy.

Other markers of abnormal cell growth that are detected by the methods of the invention include Akt1, Fas ligand and IL-6.

Diagnosis of cancers often depends on the use of crude measurements of tumor growth, such as visualization of the tumor itself, that are either inaccurate or that must reach high levels before they become detectable, e.g., in a practical clinical setting by present methods. At the point of detection, the tumor has often grown to sufficient size that intervention is unlikely to occur before metastasis. For example, detection of lung cancer by X-ray requires a tumor of >1 cm in diameter, and by CT scan of >2-3 mm. Alternatively, a biomarker of tumor growth may be used, but, again, often the tumor is well-advanced by the time the biomarker is detectable at levels accessible to current clinical technology. Furthermore, after intervention (e.g., surgery, chemotherapy, or radiation to shrink or remove the tumor or tumors), it is often not possible to measure the tumor marker with sufficient sensitivity to determine if there has been a recurrence of the cancer until residual disease has progressed to the point where further intervention is unlikely to be successful. Using the analyzers, systems, and methods of the present invention, it is possible to both detect onset of tumor growth and return of tumor growth at a point where intervention is more likely to be successful, e.g., due to lower probability of metastasis. Markers for cancer that can be detected at levels not previously shown include markers disclosed above. Examples of assays for the detection of markers that can be repurposed to diagnostic markers include TGFβ discussed above, Akt1, Fas ligand and IL-6, which are given in Examples.

7. Akt1

Akt1 is v-akt murine thymoma viral oncogene homolog 1 and is a serine-threonine protein kinase encoded by the AKT1gene. Akt kinases have been implicated in disparate cell responses, including inhibition of apoptosis and promotion of cell proliferation, angiogenesis, and tumor cell invasiveness.

Best known for its ability to inhibit apoptotic and non-apoptotic cell death, Akt can be monitored to predict tumor response to anticancer treatment. Predicting tumor response by assessing the influence of apoptosis and nonapoptotic cell death, would allow for developing a more efficient strategy for enhancing the therapeutic effect of anticancer treatment. Anticancer treatment-induced apoptosis is regulated by the balance of proapoptotic and antiapoptotic proteins through mitochondria, and resistance to apoptosis is mediated by Akt-dependent and Bcl-2-dependent pathways. Bcl-2 partially inhibits nonapoptotic cell death as well as apoptosis, whereas Akt inhibits both apoptotic and nonapoptotic cell death through several target proteins. Since drug sensitivity is likely correlated with the accumulation of apoptotic and non-apoptotic cell deaths, which may influence overall tumor response in anticancer treatment. the ability to predict overall tumor response from the modulation of several important cell death-related proteins may result in a more efficient strategy for improving the therapeutic effect.

Akt1 is also involved in Epithelial-mesenchymal transition (EMT), which is an important process during development and oncogenesis by which epithelial cells acquire fibroblast-like properties and show reduced intercellular adhesion and increased motility. AKT is activated in many human carcinomas, and the AKT-driven EMT may confer the motility required for tissue invasion and metastasis. Thus future therapies based on AKT inhibition may complement conventional treatments by controlling tumor cell invasion and metastasis. Akt is constitutively activated in most melanoma cell lines and tumor samples of different progression stages, and activation of AKT has been linked to the expression of invasion/metastasis-related melanoma cell adhesion molecule (Mel-CAM), which in turn is strongly associated with the acquisition of malignancy by human melanoma. Akt1 is also activated in pancreatic cancer, and AKT activation has been shown to correlate with higher histologic tumor grade. Thus, AKT activation is associated with tumor grade, an important prognostic factor. Akt1 is also upregulated in prostate cancer and that expression is correlated with tumor progression. Thus, Akt1 could be targeted for therapeutic intervention of cancer while at its earliest stages. In some embodiments, the analyzer systems of the invention provide a method for providing an early diagnosis of a cancer by determining the presence or concentration of Akt1 in a sample from a patient when the level of Akt 1 is less than about 100, 50, or 25 pg/ml. See Example 6.

8. Fas Ligand

Fas Ligand (FasL), also known as CD95L, is a member of the TNF family and induces apoptosis via binding to Fas (CD95). The protein exists in two forms; either membrane FasL or soluble FasL, which migrate at molecular weight of 45 kDa and 26 kDa, respectively. FasL is expressed on a variety of cells including activated lymphocytes, natural killer cells and monocytes. Interaction of FasL and Fas plays an important role in physiological apoptotic processes. Malfunction of the Fas-FasL system causes hyperplasia in peripheral lymphoid organs and accelerates autoimmune disease progression and tumorigenesis. There are limited data about the levels of soluble apoptotic factors in general, and more specifically about their modulation with therapeutic regimens.

The systems and methods of the invention can detect concentrations of Fas ligand that are as low as 2.4 pg/ml. Thus, in some embodiments, the analyzer systems and methods of the invention provide for the detection of Fas ligand to identify pathological conditions such as abnormal levels of apoptosis. Measurements of Fas in patient samples can be used to diagnose conditions such as polycystic ovarian syndrome, tumors such as testicular germ cell tumors, bladder cancer, lung cancer, and rare tumors such as follicular dendritic cell tumors. In addition, Fas measurements of Fas ligand can be used t diagnose allograft rejection; and degenerative disease such as osteoarthritis. Thus, in some embodiments, the analyzer systems and methods of the invention can be used to determine the concentration of Fas ligand in a sample from a patient suspected of suffering from Fas ligand related disorder to diagnose the disorder, or the concentration of Fas ligand can be used to monitor the progress or status of a Fas ligand related disorder in a patient undergoing therapy for the disorder. In some embodiments, the assay is capable of determining the level of Fas ligand in the sample at a concentration less than about 100, 50, 25, 10, or 5 pg/ml. See Example 8.

C. Business Methods

The present invention relates to systems and methods (including business methods) for establishing markers that can be used for diagnosing a biological state or a condition in an organism, preparing diagnostics based on such markers, and commercializing/marketing diagnostics and services utilizing such diagnostics In one embodiment, the business methods herein comprise: establishing one or more markers using a method comprising: establishing a range of concentrations for said marker or markers in biological samples obtained from a first population by measuring the concentrations of the marker or markers in the biological samples by detecting single molecules of the marker or markers; and commercializing the one or more markers identified in the above step, e.g., in a diagnostic product. The biomarkers identified are preferably polypeptides or small molecules. Such polypeptides can be previously known or unknown. The diagnostic product herein can include one or more antibodies that specifically binds to the marker (e.g., polypeptide).

In one embodiment, the business methods herein comprise: establishing one or more markers using a system comprising: establishing a range of concentrations for said marker in biological samples obtained from a first population by measuring the concentrations of the marker the biological samples by detecting single molecules of the marker; and providing a diagnostic service to determine if an organism has or does not have a biological state or condition of interest. A diagnostic service herein may be provided by a CLIA approved laboratory that is licensed under the business or the business itself. The diagnostic services herein can be provided directly to a health care provider, a health care insurer, or a patient. Thus the business methods herein can make revenue from selling e.g., diagnostic services or diagnostic products.

The business methods herein also contemplate providing diagnostic services to, for example, health care providers, insurers, patients, etc. The business herein can provide diagnostic services by either contracting out with a service lab or setting up a service lab (under Clinical Laboratory Improvement Amendment (CLIA) or other regulatory approval). Such service lab can then carry out the methods disclosed herein to identify if a particular marker or pattern of markers is within a sample.

The one or more markers are polypeptides or small molecules, or new chemical entities.

Kits

The invention further provides kits. In some embodiments, kits include an analyzer system and a label, as previously described. Kits of the invention include one or more compositions useful for the sensitive detection of a molecule, such as a marker, as described herein, in suitable packaging. In some embodiments, kits of the invention provide a label, as described herein, together with other components such as instructions, reagents, or other components. In some embodiments, the kit provides the label as separate components, in separate containers, such as an antibody and a fluorescent moiety, for attachment before use by the consumer. In some embodiments kits of the invention provide binding partner pairs, e.g., antibody pairs, that are specific for a molecule, e.g., a marker, where at least one of the binding partners is a label for the marker, as described herein. In some embodiments, the binding partners, e.g., antibodies, are provided in separate containers. In some embodiments, the binding partners, e.g., antibodies, are provided in the same container. In some embodiments, one of the binding partners, e.g., antibody, is immobilized on a solid support, e.g., a microtiter plate or a paramagnetic bead. In some of these embodiments, the other binding partner, e.g., antibody, is labeled with a fluorescent moiety as described herein.

Binding partners, e.g., antibodies, solid supports, and fluorescent labels for components of the kits may be any suitable such components as described herein.

The kits may additionally include reagents useful in the methods of the invention, e.g., buffers and other reagents used in binding reactions, washes, buffers or other reagents for preconditioning the instrument on which assays will be run, filters for filtering reagents, and elution buffers or other reagents for running samples through the instrument.

Kits may include one or more standards, e.g., standards for use in the assays of the invention, such as standards of highly purified, e.g., recombinant, protein markers, or various fragments, complexes, and the like, thereof. Kits may further include instructions.

EXAMPLES

The following examples are offered by way of illustration and not by way of limiting the remaining disclosure.

Unless otherwise specified, processing samples in the Examples were analyzed in a single molecule detector (SMD) as described herein, with the following parameters: Laser: continuous wave gallium arsenite diode laser of wavelength 639 nm (Blue Sky Research, Milpitas, Calif.), focused to a spot size of approximately 2 microns (interrogation space of 0.004 pL as defined herein); flow rate=5 microliter/min through a fused silica capillary of 100 micron square ID and 300 micron square OD; non-confocal arrangement of lenses (see, e.g., FIG. 1A); focusing lens of 0.8 numerical aperture (Olympus); silicon avalanche photodiode detector (Perkin Elmer, Waltham, Mass.).

Example 1

Sandwich Assays for Biomarkers: Cardiac Troponin I (cTnI)

The assay: The purpose of this assay was to detect the presence of cardiac Troponin I (cTNI) in human serum. The assay format was a two-step sandwich immunoassay based on a mouse monoclonal capture antibody and a goat polyconal detection antibody. Ten microliters of sample were required. The working range of the assay is 0-900 pg/ml with a typical analytical limit of detection of 1-3 pg/ml. The assay required about four hours of bench time to complete.

Materials: the following materials were used in the procedure described below: Assay plate: Nunc Maxisorp, product 464718, 384 well, clear, passively coated with monoclonal antibody, BiosPacific A34440228P Lot # A0316 (5 µg/ml in 0.05 M sodium carbonate pH 9.6, overnight at room temperature); blocked with 5% sucrose, 1% BSA in PBS, and stored at 4oC. For the standard curve, Human cardiac Troponin I (BiosPacific Cat # J34000352) was used. The diluent for the standard concentrations was human serum that was immonodepleted of endogenous cTNI, aliquoted and stored at −20oC. Dilution of the standards was done in a 96 well, conical, polypropylene, (Nunc product # 249944). The following buffers and solutions were used: (a) assay buffer: BBS with 1% BSA and 0.1% TritonX-100; (b) passive blocking solution in assay buffer containing 2 mg/ml mouse IgG, (Equitech Bio); 2 mg/ml goat IgG, (Equitech Bio); and 2 mg/ml MAK33 poly, Roche# 11939661; (c) detection Antibody (Ab): Goat Polyclonal antibody affinity purified to Peptide 3, (BiosPacific G129C), which was label with a fluorescent dye AlexaFluor 647, and stored at 4oC; detection antibody diluent: 50% assay buffer, 50% passive blocking solution; wash buffer: borate buffer saline Triton Buffer (BBST) (1.0 M borate, 15.0 M sodium chloride, 10% Triton X-100, pH 8.3); elution buffer: BBS with 4M urea, 0.02% Triton X-100 and 0.001% BSA.

Preparation of AlexaFluor 647 labeled antibodies: the detection antibody G-129-C was conjugated to AlexaFluor 647 by first dissolving 100 ug of G-129-C in 400 uL of the coupling buffer (0.1M NaHCO3). The antibody solution was then concentrated to 50 ul by transferring the solution into YM-30 filter and subjecting the solution and filter to centrifugation. The YM-30 filter and antibody was then washed three times by adding 400 ul of the coupling buffer. The antibody was recovered by adding 50□l to the filter, inverting the filter, and centrifuging for 1 minute at 5,000×g. The resulting antibody solution was 1-2 ug/ul. AlexaFluor 647 NHS ester was reconstituted by adding 20 ul DMSO to one vial of AlexaFluor 647, this solution was stored at −20oC for up to one month. 3 ul of AlexaFluor 647 stock solution was added to the antibody solution, which was then mixed and incubated in the dark for one hour. After the one hour, 7.5 ul 1M tris was added to the antibody AlexaFluor 647 solution and mixed. The solution was ultrafiltered with YM-30 to remove low molecular weight components. The volume of the retentate, which contained the antibody conjugated to AlexaFluor 647, was adjusted to 200-400 □1 by adding PBS. 3 ul 10% NaN3 was added to the solution, the resulting solution was transferred to an Ultrafree 0.22 centrifugal unit and spun for 2 minutes at 12,000×g. The filtrate containing the conjugated antibody was collected and used in the assays.

Procedure: cTnI Standard and Sample Preparation and Analysis:

The standard curve was prepared as follows: working standards were prepared (0-900 pg/ml) by serial dilutions of the stock of cTnI into standard diluent or to achieve a range of cTnI concentrations of between 1.2 pg/ml–4.3 pg/ml. 1002931 10 μl passive blocking solution and 10 μl of standard or of sample were added to each well. Standards were run in quadruplicate. The plate was sealed with Axyseal sealing film, centrifuged for 1 min at 3000 RPM, and incubated for 2 hours at 25oC with shaking. The plate was washed five times, and centrifuged until rotor reached 3000 RPM in an inverted position over a paper towel. A 1nM working dilution of detection antibody was prepared, and 20 μl detection antibody were added to each well. The plate was sealed and centrifuged, and the assay incubated for 1 hour at 25oC with shaking. 30 μl elution buffer were added per well, the plate was sealed and the assay incubated for ½ hour at 25oC. The plate was either stored for up to 48 hours at 4oC prior to analysis, or the sample was analyzed immediately.

For analysis, 20 μl per well were acquired at 40 μl/minute, and 5 μl were analyzed at 5 μl/minute. The data were analyzed based on a threshold of 4 sigma. Raw signal versus concentration of the standards was plotted. A linear fit was performed for the low concentration range, and a non-linear fit was performed for the full standard curve. The limit of detection (LoD) was calculated as LOD=(3× standard deviation of zeros)/slope of linear fit. The concentrations of the samples were determined from the equation (linear or non-linear) appropriate for the sample signal.

An aliquot was pumped into the analyzer. Individually-labeled antibodies were measured during capillary flow by setting the interrogation volume such that the emission of only 1 fluorescent label was detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of DMC events/sample. The limit of detection the cTnI assay of the invention was determined by the mean +3 SD method.

Results: Data for a typical cTnI standard curve measured in quadruplicate using the assay protocol is shown in Table 3.

TABLE 3

Standard Curve for cTnI

| cTnI (pg/ml) | Signal | Standard Deviation | % CV |
|---|---|---|---|
| 0 | 233 | 25 | 10.8 |
| 1.5625 | 346 | 31 | 8.9 |
| 3.125 | 463 | 35 | 7.5 |
| 6.25 | 695 | 39 | 5.6 |
| 12.5 | 1137 | 61 | 5.3 |
| 25 | 1988 | 139 | 7.0 |
| 50 | 3654 | 174 | 4.8 |
| 100 | 5493 | 350 | 6.4 |
| 200 | 8264 | 267 | 3.2 |
| 400 | 9702 | 149 | 1.5 |
| 800 | 9976 | 50 | 0.5 |

The sensitivity of the analyzer system was tested in 15 runs and was round routinely to detect sub femtomol/l (fM) levels of calibrator, as shown by the data in Table 4. The precision was 10% at 4 and 12 pg/ml cTnI.

TABLE 4

Instrument Sensitivity

| Calibrator (fM) | Signal counts | CV |
|---|---|---|
| 0 | 11 | |
| 12 | 302 | 9 |
| 60 | 1341 | 8 |
| 300 | 4784 | 7 |

Figure 5:
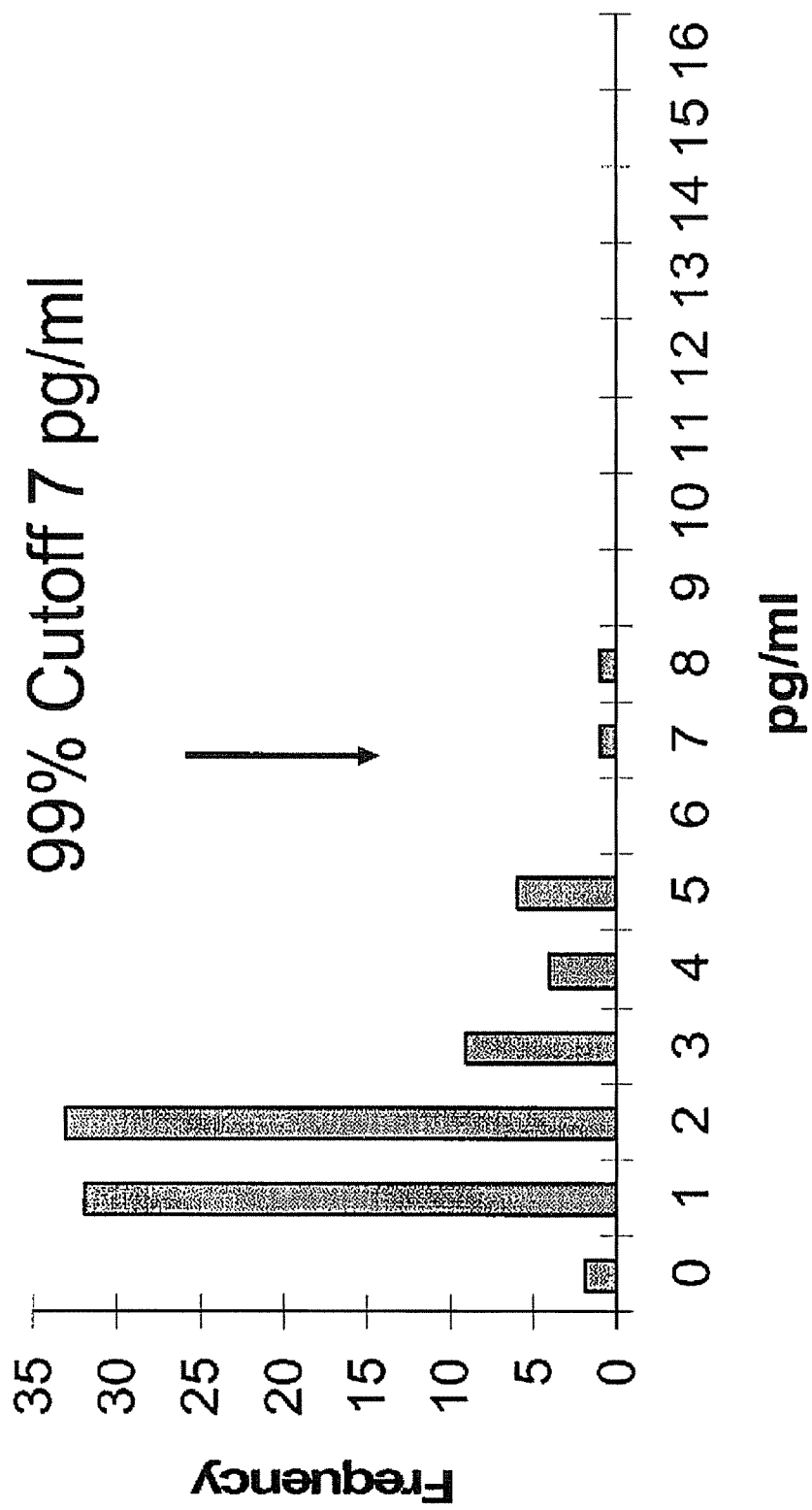
FIG. 5. Biological threshold (cutoff concentration) for cTnI is at a cTnI concentration of 7 pg/ml, as established at the 99th percentile with a corresponding CV of 10%.

Linearized standard curve for the range concentrations of cTnI are shown in FIG. 5.

The analytical limit of detection (LoD) was determined across 15 sequential assays. The LoD was the mean of the 0 std+3 SD (n=4) intra-assay determinations. The average LoD was 1.7 pg/ml (range 0.4-2.8 pg/ml).

The recovery of the sample was determined by analyzing samples of serum that had been immunodepleted of cTnI and spiked with known amounts of cTnI. Table 5 shows the data for sample recovery by the system analyzed over 3 days.

TABLE 5

Sample Recovery

| Spike (pg/ml) | Recovery (mean) | Standard Deviation | % CV |
|---|---|---|---|
| 5 | 5.7 | 0.9 | 16 |
| 15 | 13.7 | 0.2 | 2 |
| 45 | 43 | 0.6 | 2 |
| 135 | 151 | 6.2 | 4 |

The linearity of the assay was determined in pooled human serum that was spiked with cTnI and diluted with standard diluent. The results in Table 6 show the dilutions and % of the signal expected for the corresponding dilution.

TABLE 6

Assay Linearity

| Serum Dilution | % of expected |
|---|---|
| 1:2 | 79 |
| 1:4 | 87 |
| 1:8 | 96 |

These data show that the analyzer system of the invention allows for performing highly sensitive laser-induced immunoassay for sub-femtomolar concentrations of cTnI.

Example 2

Sandwich Bead-Based Assays for TnI

The assays described above use the same microtiter plate format where the plastic surface is used to immobilize target molecules. The single particle analyzer system also is compatible with assays done in solution using microparticles or beads to achieve separation of bound from unbound entities.

Materials: MyOne Streptavidin C1 microparticles (MPs) are obtained from Dynal (650.01-03, 10 mg/ml stock). Buffers use in the assay include: 10× borate buffer saline Triton Buffer (BBST) (1.0 M borate, 15.0 M sodium chloride, 10%

Triton X-100, pH 8.3); assay buffer (2 mg/ml normal goat IgG, 2 mg/ml normal mouse IgG, and 0.2 mg/ml MAB-33-IgG-Polymer in 0.1 M Tris (pH 8.1), 0.025 M EDTA, 0.15 M NaCl, 0.1% BSA, 0.1% Triton X-100, and 0.1% NaN3, stored at 4C); and elution buffer (BBS with 4 M urea, 0.02% Triton X-100, and 0.001% BSA, stored at 2-8C). Antibodies used in the sandwich bead-based assay include: Bio-Ab (A34650228P (BiosPacific) with 1-2 biotins per IgG) and Det-Ab (G-129-C (BiosPacific) conjugated to A647, 2-4 fluors per IgG). The standard is recombinant human cardiac troponin I (BiosPacific, cat #J34120352). The calibrator diluent is 30 mg/ml BSA in TBS wEDTA.

Microparticles Coating: 100 ul of the MPs stock is placed in an eppendorf tube. The MPs are washed three times with 100 ul of BBST wash buffer by applying a magnet, removing the supernatant, removing the magnet, and resuspending in wash buffer. After the washes the MPs are resuspended in 100 ul of assay buffer and 15 ug of Bio-Ab are added. The mixture is then incubated for an hour at room temperature with constant mixing. The MPs are washed five times with 1 ml wash buffer as described above. After the washes the MPs are resuspended in 15 ml of assay buffer (or 100 ul to store at 4° C.).

Preparation of Standard and Samples: the Standard is Diluted with Calibrator Diluent to Prepare Proper Standard curve (usually 200 pg/ml down to 0.1 pg/ml). Frozen serum and plasma samples need to be centrifuged 10 minutes at room temperature at 13 K rpm. Clarified serum/plasma is removed carefully to avoid taking any possible pellets or floaters and put into fresh tubes. 50 ul of each standard or sample is pippetted into appropriate wells.

Capture Target: 150 ul of MPs (after resuspension to 15 ml in assay buffer+400 mM NaCl) are added to each well. The mixture is incubated on JitterBug, 5 at room temperature for 1 hr.

Washes and Detection: The plate is placed on a magnet and the supernatant is removed after ensuring that all MPs are captured by the magnet. 250 ul of wash buffer are added after removing the plate from the magnet. The plate is then placed on the magnet and the supernatant is removed after ensuring that all MPs are captured by the magnet. 20 ul Det-Ab are added per well (Det-Ab to 500 ng/ml is diluted in assay buffer+400 mM NaCl)). The mixture is incubated on JitterBug, 5 at room temperature for 30 min.

Washes and Elution: The plate is placed on a magnet and washed three times with wash buffer. The supernatant is removed after ensuring that all MPs are captured by the magnet and 250 ul of wash buffer are added. After the washes the samples are transferred into a new 96-well plate. The new plate is then placed on the magnet and the supernatant is removed after ensuring that all MPs are captured by the magnet. 250 ul of wash buffer are then added after removing the plate from the magnet. The plate is then placed on the magnet and the supernatant is removed after ensuring that all MPs are captured by the magnet. 20 ul of elution buffer are then added and the mixture is incubated on JitterBug, 5 at room temperature for 30 min.

Filter out MPs and transfer to 384-well plate: The standard and samples are transferred into a 384-well filter plate placed on top of a 384-well assay plate. The plate is then centrifuged at room temperature at 3000 rpm with a plate rotor. The filter plate is removed and the appropriate calibrators are added. The plate is covered and is ready to be run on SMD.

SMD: An aliquot is pumped into the analyzer. Individually-labeled antibodies are measured during capillary flow by setting the interrogation volume such that the emission of only 1 fluorescent molecule is detected in a defined space following laser excitation. With each signal representing a digital event, this configuration enables extremely high analytical sensitivities. Total fluorescent signal is determined as a sum of the individual digital events. Each molecule counted is a positive data point with hundreds to thousands of DMC events/sample. The limit of detection the cTnI assay of the invention is determined by the mean +3 SD method.

Example 3

Concentration Range for cTnI in a Population of Normal Non-Diseased Subjects

A reference range or normal range for cTnI concentrations in human serum was established using serum samples from 88 apparently healthy subjects (non-diseased). A sandwich immunoassay as described in Example 1 was performed and the number of signals or events as described above were counted using the single particle analyzer system of the invention. The concentration of serum troponin I was determined by correlating the signals detected by the analyzer with the standard curve as described above. All assays were perfumed in quadruplicate.

In accordance with recommendations by the current European and American Cardiology Societies (ESC/ACC) troponin assays should quantify accurately the 99th percentile of the normal range with an assay imprecision (CV) of less than 10% in order to distinguish reliably between patients with ACS and patients without ischemic heart disease, and risk stratification for adverse cardiac events. The assay showed that the biological threshold (cutoff concentration) for TnI is at a TnI concentration of 7 pg/ml, which is established at the 99th percentile with a corresponding CV of 10% (FIG. 5). At the 10% CV level the precision profile points at a TnI concentration of 4 and 12 pg/ml.

Figure 6:
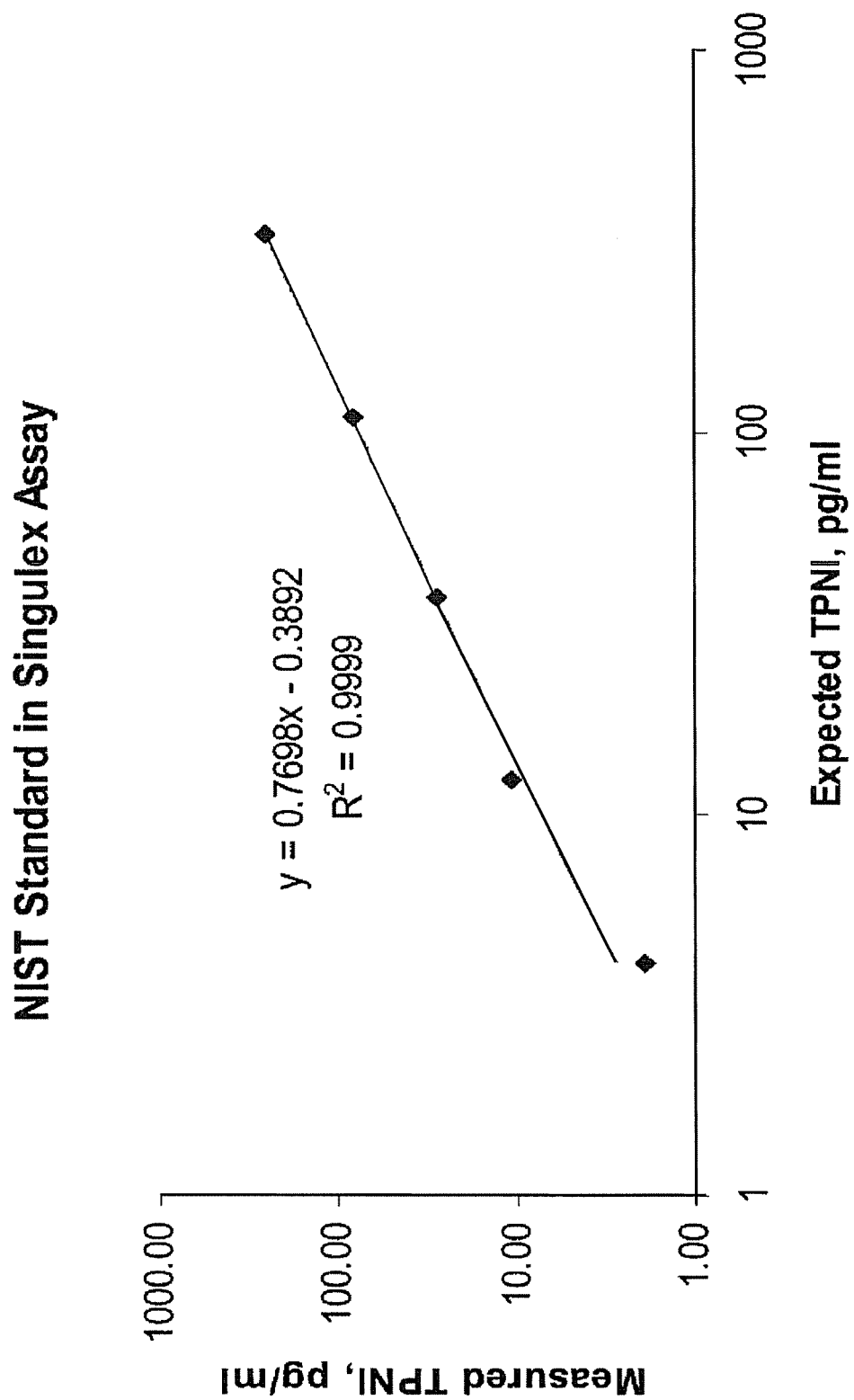
FIG. 6. Correlation of assay results of cTnI determined using the analyzer system of the invention with standard measurements provided by the National Institute of Standards and Technology (R2=0.9999).

In addition, the assay correlates well with the Troponin-I standard measurements provided by the National Institute of Standards and Technology (FIG. 6).

The assay of the invention is sufficiently sensitive and precise to fulfill the requirements of the ESC/ACC, and it is the most sensitive assay for cardiac troponin I when compared to assays such as those described by Koerbin et al.(Ann Clin Biochem, 42:19-23 (2005). The assay of the invention has a 10-20 fold greater sensitivity than that currently available assays, which has determined the biological threshold range to be 111-333 pg/ml cTnI.

Example 4

Detection of Early Release of TnI into the Circulation of Patients with Acute Myocardial Infarction (AMI)

Study 1:47 samples were obtained serially from 18 patients that presented with chest pain in the emergency department (ED). These patients all had non-ST elevated ECG were, and were diagnosed with AMI. The concentration of cTnI in the initial samples from all 18 patients was determined according to a commercial assay at the time of admission to the emergency room to be <350 pg/ml (10% cutpoint), and 12 were <100 pg/ml (99th %) percentile. These samples were tested at later times using the same commercial assay, and were determined to test positive for cTnI. The same serum samples were also assayed for TnI according to the assay of the invention as described in Examples 1 and 3, and the results compared to the results obtained using the commercial assay.

Figure 7:
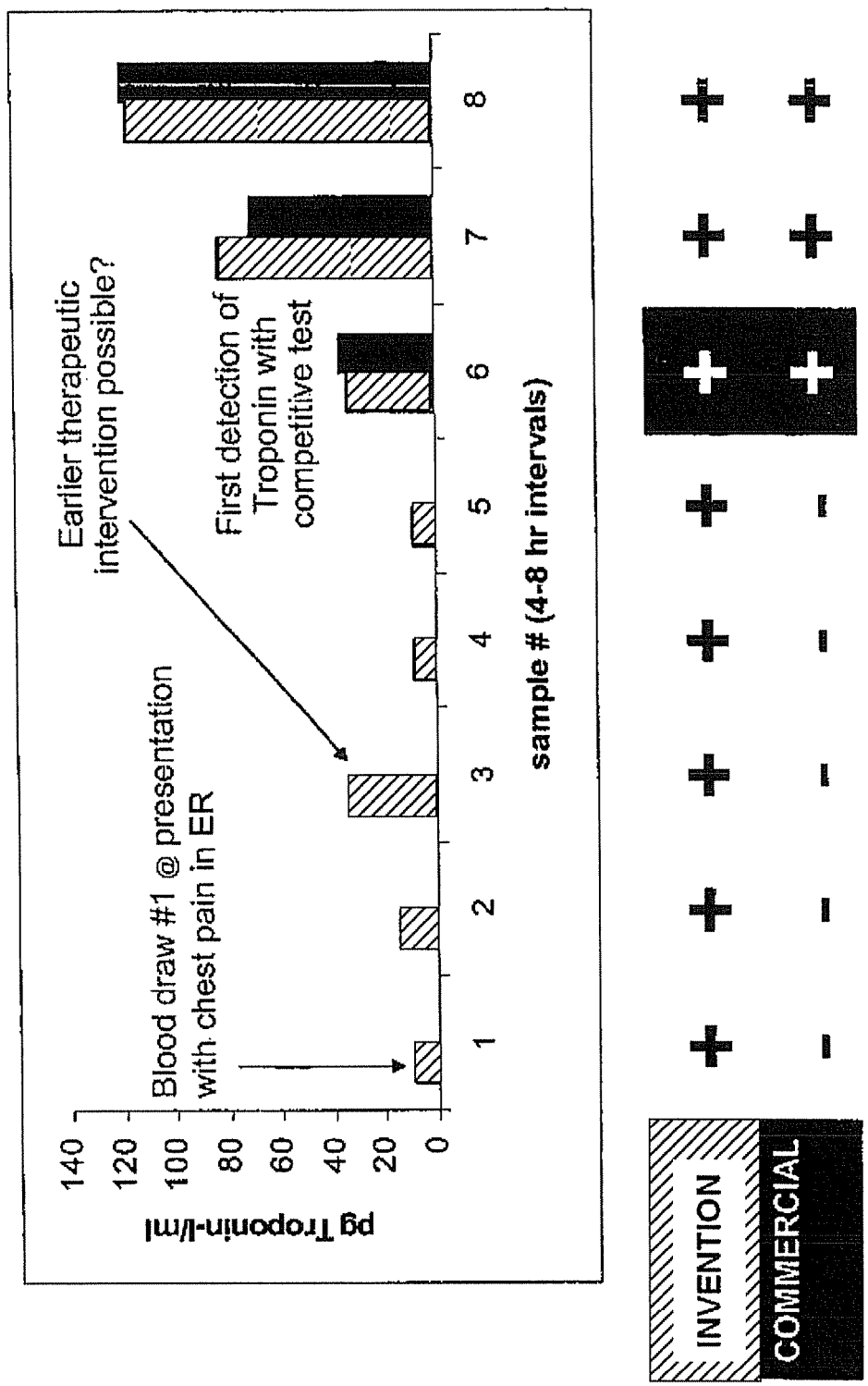
FIG. 7. Detection of cTnI in serial serum samples from patients who presented at the emergency room with chest pain. The measurements made with the analyzer system of the invention were compared to measurements made with a commercially available assay.

Blood was drawn for the first time at the time the patient presented with chest pain (sample 1), and subsequently at intervals between 4-8 hours (samples 2 at 12 hours; sample 3 at 16 hours; sample 4 at 24 hours; sample 5 at 30 hours; sample 6 at 36 hours; sample 7 at 42 hours; and sample 8 at 48 hours). The serum was analyzed by the methods of the invention and by a current commercial method, and the results obtained are shown in FIG. 7. The analyzer of the invention detected TnI at the time the patient presented with chest pain (sample 1), while the commercial assay first detected cTnI at a much later time (sample 6 at 36 hours). The concentration of TnI in sample 3 exceeded the biological threshold level that was established using the analyzer of the invention (7 pg/ml, see FIG. 5), and indicated that sample 3 is positive for TnI to suggest the incidence of a cardiac event. The biological threshold for the commercial assay lies between 111 and 333 pg/ml of TnI. Accordingly, sample 3 would not have been considered to indicate a possible cardiac event.

In addition, the methods and compositions of the present invention allow for much earlier diagnosis and possible intervention based on cardiac troponin levels, as evidenced by results for the first sample taken from the patients. In the 3 cases that had initial commercial assay cTnI values of between 100 and 350 ng/ml, all were positive for cTnI by the analytical methods of the invention (i.e., cTnI over 7 pg/ml). In the 12 cases that had initial commercial cTnI values of less than 100 pg/ml, 5 were determined to be positive for a cardiovascular event according to the assay of the invention (i.e., cTnI over 7 pg/ml). The prospective use of the assay of the invention would have detected 53% more AMI cases than the current commercial assay when the admission sample was tested.

Figure 8:
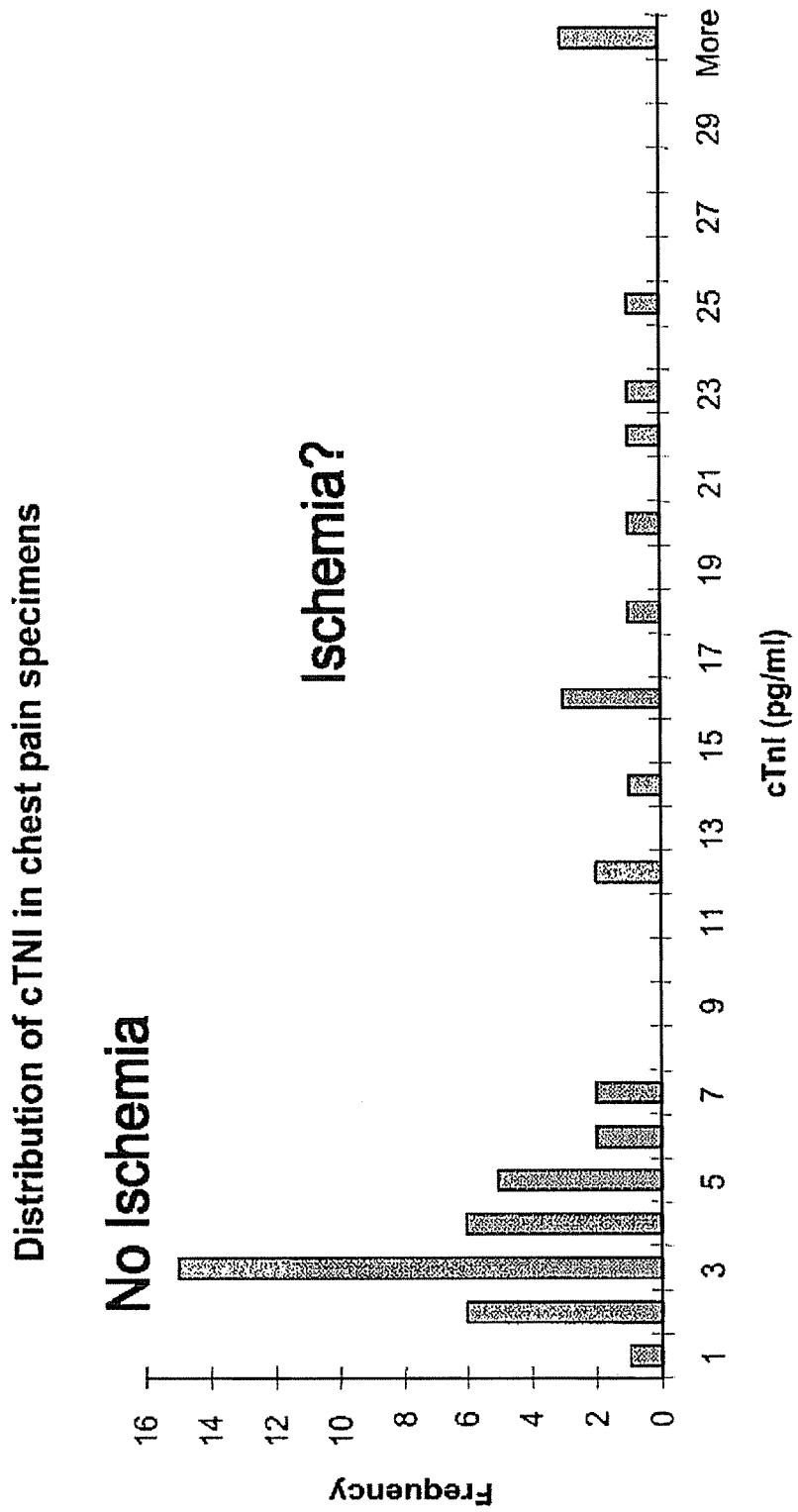
FIG. 8. Distribution of normal biological concentrations of cTnI and concentrations of cTnI in serum samples from patients presenting with chest pain FIG. 9. Competition curve for LTE4. The LOD was determined to be 1.5 pg/ml LTE4.

Study 2: 50 additional serum samples, which tested negative according to the commercial assay, were tested using the analyzer and assay of the invention. The results are shown in FIG. 8. Of the 50 samples, 36 were within the 99th % and determined to be within the normal range established by the assay of the invention. However, the remaining 14 samples that were determined to be within the commercial "normal" or non-diseased range, tested above the biological threshold established by the invention.

Therefore, the high sensitivity cTnI assay of the invention allows for the detection of myocardial damage in patients when cTnI serum levels are below threshold values by commercially available technology. The use of the highly sensitive and precise cTnI assay of the invention enables detection of AMI earlier than with existing cTnI assays, and thereby provides the opportunity for appropriate diagnosis and early medical intervention to improve the outcome.

Example 5

Detection of Leukotriene T4 (LTE4)

The assay was developed to quantify Leukotriene $E_4$ ($LTE_4$) in buffer as a preliminary assay for assays using, e.g., urine specimens. The assay format was a one-step single antibody competitive immunoassay. Fifty microliters of sample were required. The typical working range of this assay was 0-300 pg/ml with a typical limit of detection of 2-3 pg/ml (0.1-0.15 pg/sample). The assay required about four hours of bench time to complete.

The following materials were prepared and used in the procedure described below: Mouse anti-rabbit IgG coated plate provided in Cayman Chemical Leukotriene $E_4$ (EIA Kit, Catalog #520411); stock $LTE_4$ Standard (purified $LTE_4$ at 100 ng/ml in ethanol (Cayman Chemical Leukotriene $E_4$ EIA Kit, Catalog #520411)); assay buffer (10×EIA buffer concentrate (Cayman Chemical Leukotriene $E_4$ EIA Kit, Catalog #520411)) diluted 1:10 with 90 ml Nanopure water; buffer for dilution of standards (3% ethanol); anti-$LTE_4$ antibody (Leukotriene $E_4$ EIA antiserum (Cayman Chemical Leukotriene $E_4$ EIA Kit, Catalog #520411) diluted with 30 ml EIA buffer; streptavidin-Alexa detection reagent stock solution of 31 µM (streptavidin labeled with AlexaFluor™ 647); tracer ($LTE_4$-biotin conjugate) was made compatible for detection by the analyzer; wash buffer (400× concentrate (Cayman Chemical Leukotriene $E_4$ EIA Kit, Catalog #520411)) diluted 1:40; elution buffer (borate buffered saline, pH 8.3 with 4M urea, 0.02% Triton X-100 and 0.001% BSA). The matrix of the tracer and the antiserum concentrations were tested to identify the most sensitive assay conditions.

A standard curve was prepared as follows: working standards were prepared by making serial dilutions of the 100 ng/ml stock into assay buffer to achieve a range of concentrations between 0.005 pg/ml and 3000 pg/ml. 50 µl standard (or sample) were added per well of the assay plate. All standards were run in duplicate. Working tracer was prepared by diluting the tracer stock to 1 pg/ml with assay buffer. 50 ul tracer (or buffer) were added per well of the assay plate. A 10% working antiserum solution was prepared by diluting 100% stock (made according to the kit instructions) into assay buffer. 50 µl antiserum (or buffer) were added per well of the assay plate; the plate was sealed and incubated overnight at 25° C. with shaking. A working streptavidin-Alexa detection reagent was prepared by diluting stock to 140 pM with assay buffer. 15 ul of detection reagent were added to each well, and the plate was incubated for 30 min at 25° C. with shaking. The plate was washed 5 times. 50 ul of elution buffer were added to each well, and the plate was incubated for ½ hour at 25° C. with shaking. The plate was use immediately or stored for up to 48 hours at 4° C. prior to analysis.

20 µl were pumped into the analyzer at a rate of 40 µl/minute, and 5 µl of sample were analyzed at 5 µl/minute. The data files were analyzed using a threshold=4 sigma, and a cross correlation of between 0-8 msec. Raw signal versus concentration was plotted for the standards, and a linear fit was used for low range standards, while a non-linear fit was used for full standard curve. The limit of detection was calculated as LOD=80% of the maximum signal (no target control) (the concentration at which $B/B_0$=80%). The concentrations of samples were calculated from the equation (linear or non-linear) appropriate for the sample signal.

Figure 9:
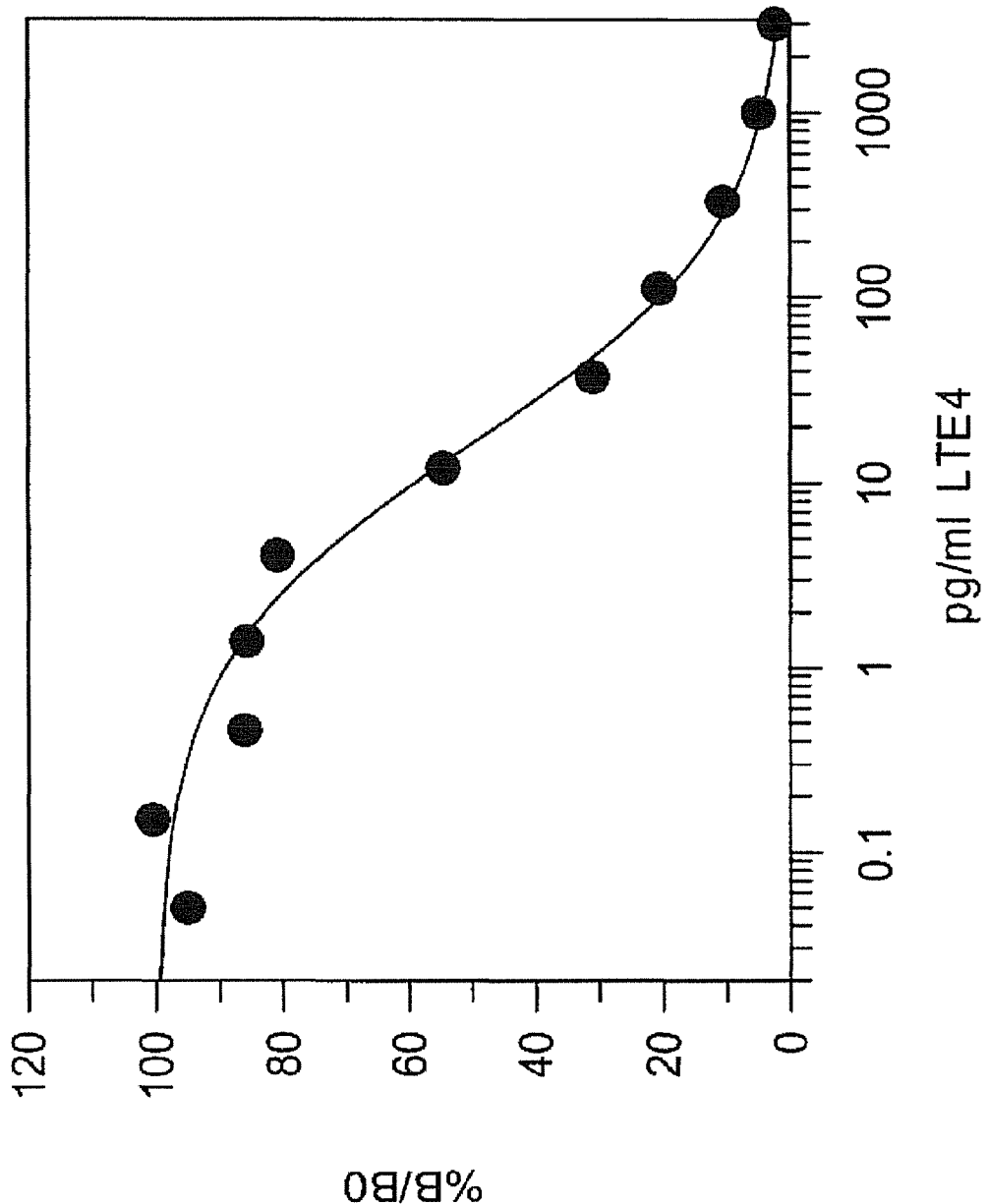

The competition curve of LTE4 is shown in FIG. 9. The LOD was calculated to be 80% $B/B_0$=1.5 pg/ml (approximately 5 pM). The LTE4 assay performed using a commercially available kit can detect LTE4 only if present at a concentration of at least 30 pg/ml.

Therefore, the analyzer system can be used to detect levels of LTE4 to indicate the presence of an LTE4-related disorder e.g. asthma at the onset of disease, and alert clinicians to the need for therapeutic intervention at an early stage of the disease to improve the clinical outcome.

Example 6

Detection of Human Akt1

A sandwich immunoassay was developed for the quantification of low levels of Akt1 in serum samples. A standard curve was generated by dilution of a concentrated standard into a buffered protein solution. Ten microliters (µl) of assay buffer and 10 µl of sample or standard were added to each well of a 384-well plate that had been coated with an antibody specific for Akt1 and incubated for two hours. More specifically antibody 841660 (R&D Systems) was coated onto Nunc Maxisorp plates @ 2.5 micrograms/ml. The plate was washed, and 20 μl of labeled detection antibody specific for Akt1, AF1775 (R&D Systems), labeled with AlexaFluor 647, 2-4 fluors/IgG, was added to each well. After one hour of incubation the plate was washed to remove unbound detection antibody. Bound detection antibody was eluted and measured in the analyzer instrument.

The following materials were used in the assay procedure described below. Coated 384 well plate; assay buffer; resuspension buffer; dilution buffer; standard diluent; Akt1 standard; detection antibody reagent for Akt1; wash buffer (10 mM Borate, 150mM NaCl, 0.1% TritonX-100, pH 8.3); elution buffer (4 M urea with 0.02% Triton X-100 and 0.001% BSA), Microplate shaker, set at "7", Microplate washer, Plate centrifuge, Axyseal sealing film, Axygen product 321-31-051, Nunc pierceable sealing tape, Nunc product 235306.

Materials
Provided Reagents
Capture antibody: 841660 (R&D Systems), coated onto Nunc Maxisorp plates @ 2.5 micrograms/ml (384 well plate)
Assay buffer
Resuspension Buffer
Dilution Buffer
Standard diluent
Akt 1 standard
Detection antibody reagent for Akt1, AF 1775 (R&D Systems), labeled with AlexaFluor 647, 2-4 fluors/IgG
Other Required Reagents
    TritonX-100 Wash buffer (10 mM Borate, 150 mM NaCl, 0.1% TritonX-100, pH 8.3)
    Elution buffer (4 M urea with 0.02% Triton X-100 and 0.001% BSA)
    Microplate shaker, set at "7"
    Microplate washer
    Plate centrifuge
    Axyseal sealing film, Axygen product 321-31-051
    Nunc pierceable sealing tape, Nunc product 235306
Procedure
Akt1 standard preparation
    Resuspend standard in 0.5 ml Resuspension Buffer, final concentration 170 ng/1 ml
    Dilute standard 1:3 in Dilution Buffer=57 ng/ml
    Dilute standard 1:19 in Standard Diluent=3 ng/ml
Do serial 3 fold dilutions down to 4.1 pg/ml in Standard Diluent
Add 10 μl Assay Buffer per well
Add 10 μl standard or sample per well
Seal plate with Axyseal sealing film
Spin 1 min at 3000 RPM
Incubate 2 hours at 25oC with shaking
Wash plate five times
Spin plate inverted on a paper towel 1 min at 3000 RPM
Add 20 μl detection antibody reagent per well
Seal plate with Axyseal sealing film
Spin plate inverted on a paper towel 1 min at 3000 RPM
Incubate 1 hour at 25oC with shaking
Wash plate five times
Spin plate inverted on a paper towel 1 min at 3000 RPM
Add 30 μl elution buffer per well
Spin 1 min at 3000 RPM
Seal with Nunc pierceable sealing tape, secure tight seal with roller
Incubate ½ hour at 25oC with shaking
The plate may be stored for up to 48 hours at 4oC prior to analysis
Analyze on Zeptx instrument The Akt1 standard curve was generated as follows. Akt1 standards were prepared to achieve a range of between 4.1 pg/ml to 170 ng/ml Akt1. 10 μl of each standard dilution (or sample) were added to the assay plate wells. The plate was sealed and incubated for 2 hours at 25° C. with shaking. The plate was washed and centrifuged dry. 20 μl detection antibody reagent was added per well and incubated for 1 hour at 25° C. with shaking. The antibody-Akt1 complex was disrupted by adding 30 μl elution buffer per well and incubating for ½ hour at 25° C. with shaking. The plate was either used immediately or stored for up to 48 hours at 4° C. prior to analysis. Eluate was pumped into the analyzer.

Figure 10:
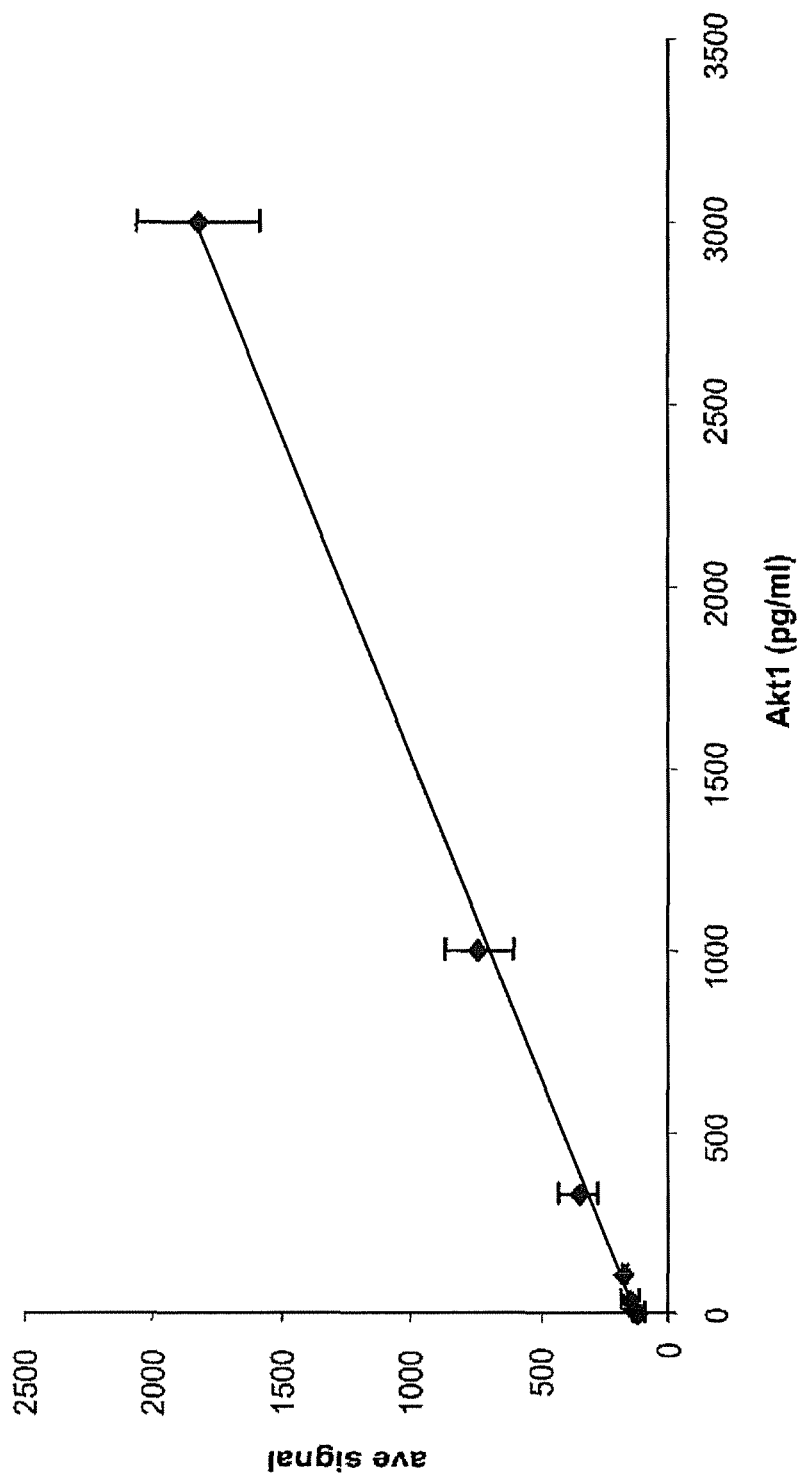
FIG. 10. Graph showing the standard curve for concentrations of Akt1. The LOD was calculated to be 25 pg/ml Akt1.

Data for a typical Akt1 standard curve measured in quadruplicate using the assay protocol is given in Table 14, and the graphed data is shown in FIG. 10.

TABLE 14

Standard curve for Akt1

| Concentration Akt1 standard (pg/ml) | Average Signal | Standard deviation | % CV |
|---|---|---|---|
| 0 | 113 | 16 | 14 |
| 4.1 | 126 | 10 | 8 |
| 12.4 | 133 | 1 | 0 |
| 37 | 151 | 34 | 22 |
| 111 | 173 | 15 | 8 |
| 333 | 350 | 74 | 21 |
| 1000 | 733 | 136 | 19 |
| 3000 | 1822 | 243 | 13 |

Intra-Assay Precision was tested using 36 replicate samples of the 1000 pg/ml standard by assaying the samples on a single plate. The average signal was 1822±243 with a % CV=13. The limit of detection of the assay (LoD) was determined by adding two standard deviations to the mean signal of thirty six zero standard replicates and calculating the corresponding Akt1 concentration from the standard curve. The LoD was calculated to be 25 pg/ml.

Therefore, the analyzer system can be used to detect levels of Akt1 to determine the presence or absence of an Akt1-related disorder, e.g. cancer.

Example 7

Detection of TGF-β

A sandwich immunoassay was developed for the quantification of low levels of TGFβ in serum. A standard curve was generated by dilution of a concentrated standard into a buffeted protein solution. Ten microliters (μl) of assay buffer and 10 μl of sample or standard were added to each well of a 384-well plate coated with an antibody specific for TGFβ and incubated for two hours. The plate was washed and 20 μl of labeled detection antibody specific for TGFβ was added to each well. After one hour of incubation the plate was washed to remove unbound detection antibody. Bound detection antibody was eluted and measured in the analyzer instrument.

The following materials were used in the assay procedure described below. Coated 384 well plate; assay buffer; standard diluent; 10 ug/ml stock solution of TGFβ standard; detection antibody reagent for TGFβ; TritonX-100 Wash buffer (10mM Borate, 150 mM NaCl, 0.1% TritonX-100, pH 8.3); elution buffer (4 M urea with 0.02% TritonX-100 and 0.001% BSA).

The TGF-β standard curve was generated as follows. TGF-β standards were prepared to achieve a range of between 100 ng/ml to 4.1 pg/ml TGFβ. 10 µl assay buffer and 10 µl standard or sample were added to each well. The plate was sealed and incubated for 2 hours at 25° C. with shaking. The plate was sealed and incubated for 2 hours at 25° C. with shaking. The plate was washed and centrifuged dry. 20 µl detection antibody reagent was added per well and incubated for 1 hour at 25° C. with shaking. The antibody-TGF-β complex was disrupted by adding 30 µl elution buffer per well and incubating for ½ hour at 25° C. with shaking. The plate was either used immediately or stored for up to 48 hours at 4° C. prior to analysis. Eluate was pumped into the analyzer.

Figure 11:
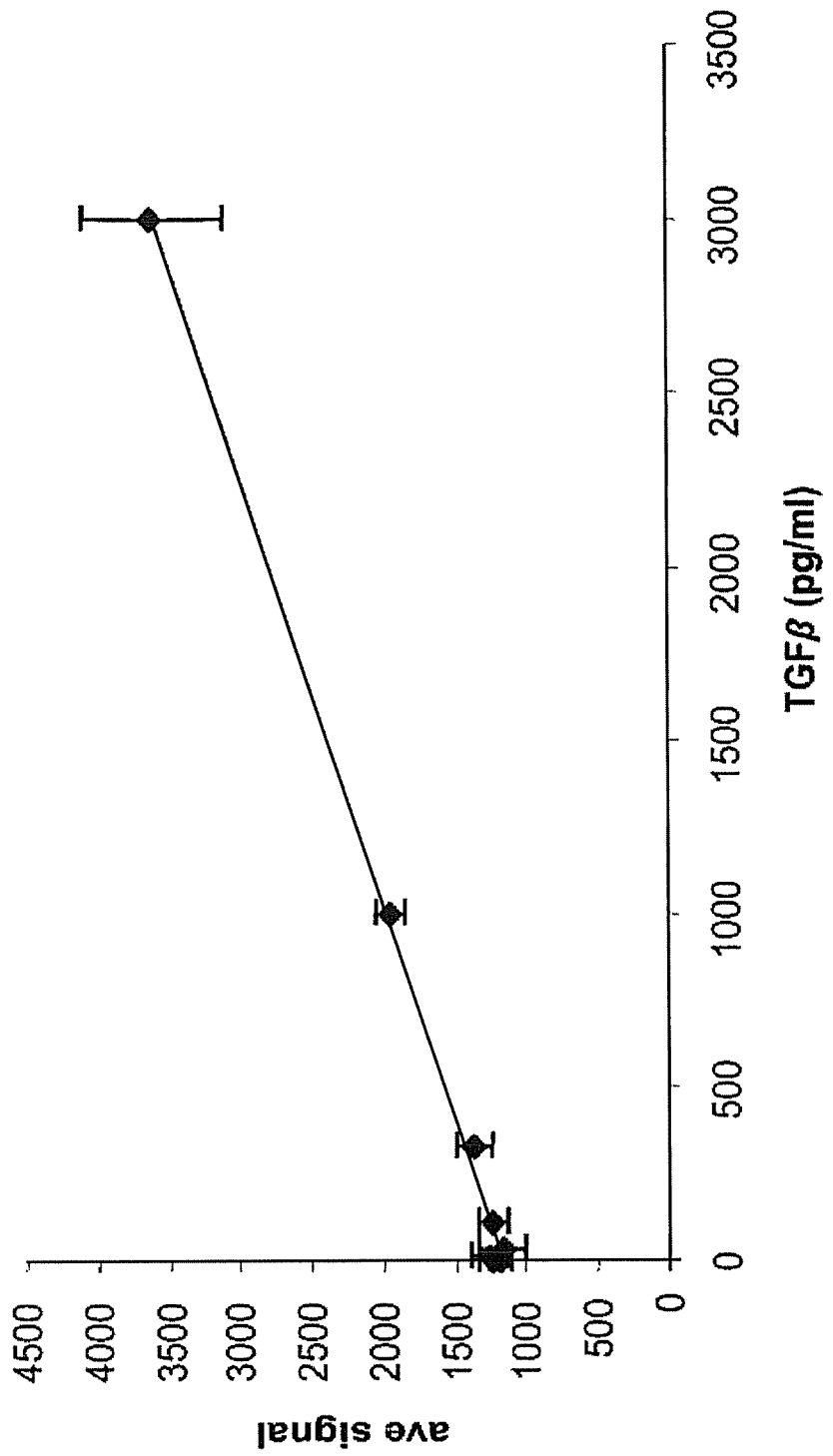
FIG. 11. Graph showing the standard curve for concentrations of TGFβ. The LOD was calculated to be 350 pg/ml Akt1.

Data for a typical TGF-β standard curve measured in quadruplicate using the assay protocol is given in Table 15, and the graphed data is shown in FIG. 11.

TABLE 15

Standard curve for TGF-β

| Concentration (pg/ml) | Average Signal | Standard deviation | % CV |
|---|---|---|---|
| 0 | 1230 | 114 | 9 |
| 4 | 1190 | 68 | 6 |
| 12 | 1261 | 132 | 10 |
| 37 | 1170 | 158 | 14 |
| 111 | 1242 | 103 | 8 |
| 333 | 1364 | 135 | 10 |
| 1000 | 1939 | 100 | 5 |
| 3000 | 3604 | 497 | 14 |

The limit of detection of the assay (LoD) was determined by adding two standard deviations to the mean signal of twenty zero standard replicates and calculating the corresponding TGFβ concentration from the standard curve. The LoD=350 pg/ml.

Therefore, the analyzer system can be used to detect levels of TGFβ to determine the presence or absence of an TGFβ-related disorder, e.g. cancer.

Example 8

Detection of Fas Ligand

A sandwich immunoassay for the quantification of low levels of Fas ligand in serum. A standard curve was generated by dilution of a concentrated standard into a buffered protein solution. Ten microliters (µl) of assay buffer and 10 µl of sample or standard were added to each well of a 384-well plate coated with an antibody specific for Fas ligand and incubated for 2 hours. The plate was washed and 20 µl of labeled detection antibody specific for Fas ligand was added to each well. After a 1 hour incubation the plate was washed to remove unbound detection antibody. Bound detection antibody was eluted and measured in the Zeptx instrument.

The Fas ligand standard curve was generated as follows. Fas ligand standards were prepared to achieve a range of between 100 ng/ml to 4.1 pg/ml Fas ligand. 10 µl assay buffer and 10 µl standard or sample were added to each well. The plate was sealed and incubated for 2 hours at 25° C. with shaking. The plate was sealed and incubated for 2 hours at 25° C. with shaking. The plate was washed and centrifuged dry. 20 µl detection antibody reagent was added per well and incubated for 1 hour at 25° C. with shaking. The antibody-Fas ligand complex was disrupted by adding 30 µl elution buffer per well and incubating for 1 hour at 25° C. with shaking. The plate was either used immediately or stored for up to 48 hours at 4° C. prior to analysis.

Data for a typical Fas ligand standard curve measured in quadruplicate using the assay protocol is given in Table 16.

TABLE 16

Standard curve for Fas ligand

| Concentration Fas ligand standard (pg/ml) | Average Signal | Standard deviation | % CV |
|---|---|---|---|
| 0 | 935 | 82 | 9 |
| 1.2 | 1007 | 44 | 4 |
| 3.4 | 1222 | 56 | 5 |
| 11 | 1587 | 70 | 4 |
| 33 | 2869 | 52 | 2 |
| 100 | 5939 | 141 | 2 |
| 300 | 9276 | 165 | 2 |
| 900 | 11086 | 75 | 1 |

Intra-Assay Precision was tested using 12 replicate samples of 3 standard concentrations by assaying the samples on a single plate. The mean, standard deviation and CV for the 12 values for each of the three points are shown in Table 17.

TABLE 17

Intra-assay precision for Fas ligand

| Concentration (pg/ml) | Average Signal | Standard deviation | % CV |
|---|---|---|---|
| 11 | 1717 | 128 | 7 |
| 33 | 3031 | 262 | 9 |
| 100 | 6025 | 257 | 4 |

The limit of detection of the assay (LoD) was determined by adding two standard deviations to the mean signal of twenty zero standard replicates and calculating the corresponding Fas ligand concentration from the standard curve. The LoD was calculated to be 2.4 pg/ml Therefore, the analyzer system of the invention can detect levels of Fas ligand to indicate the presence of a Fas ligand-related disorder e.g. cancer, allograft rejection and degenerative diseases such as osteoarthritis.

Example 9

Sandwich Assays for Biomarker TREM-1

Recent reports have established TREM-1 as a biomarker of bacterial or fungal infections (see, e.g., Bouchon et al. (2000) J. Immunol. 164:4991-5; Colonna (2003) Nat. Rev. Immunol. 3:445-53; Gibot et al. (2004) N. Engl. J. Med. 350:45 1-8; Gibot et al. (2004) Ann. Intern. Med. 141:9-15. Assays for TREM-1 have been developed using a sandwich assay format (Sandwich Assay for Detection of Individual Molecules, U.S. Provisional Patent Application No. 60/624,785). Assay reagents for TREM-1 detection are available commercially (R&D Systems, Minneapolis, Minn.). The assay was done in a 96 well plate. A monoclonal antibody was used as the capture reagent, and either another monoclonal or a polyclonal antibody was used for detection. The detection antibody was labeled with AlexaFluorA647®.

The assay protocol was as follows:
1. Coat plates with the capture antibody, washed 5×,
2. Block in 1% BSA, 5% sucrose in PBS,
3. Add the target diluted in serum, incubate, wash 5×,
4. Add the detection antibody, incubate, wash 5×
5. Add 0.1 M glycine pH 2.8 to release the bound assay components from the plate.

6. Transfer samples from the processing plate to the detection plate, bring the pH of the sample to neutral and run on the single particle analyzer system.

Figure 13:
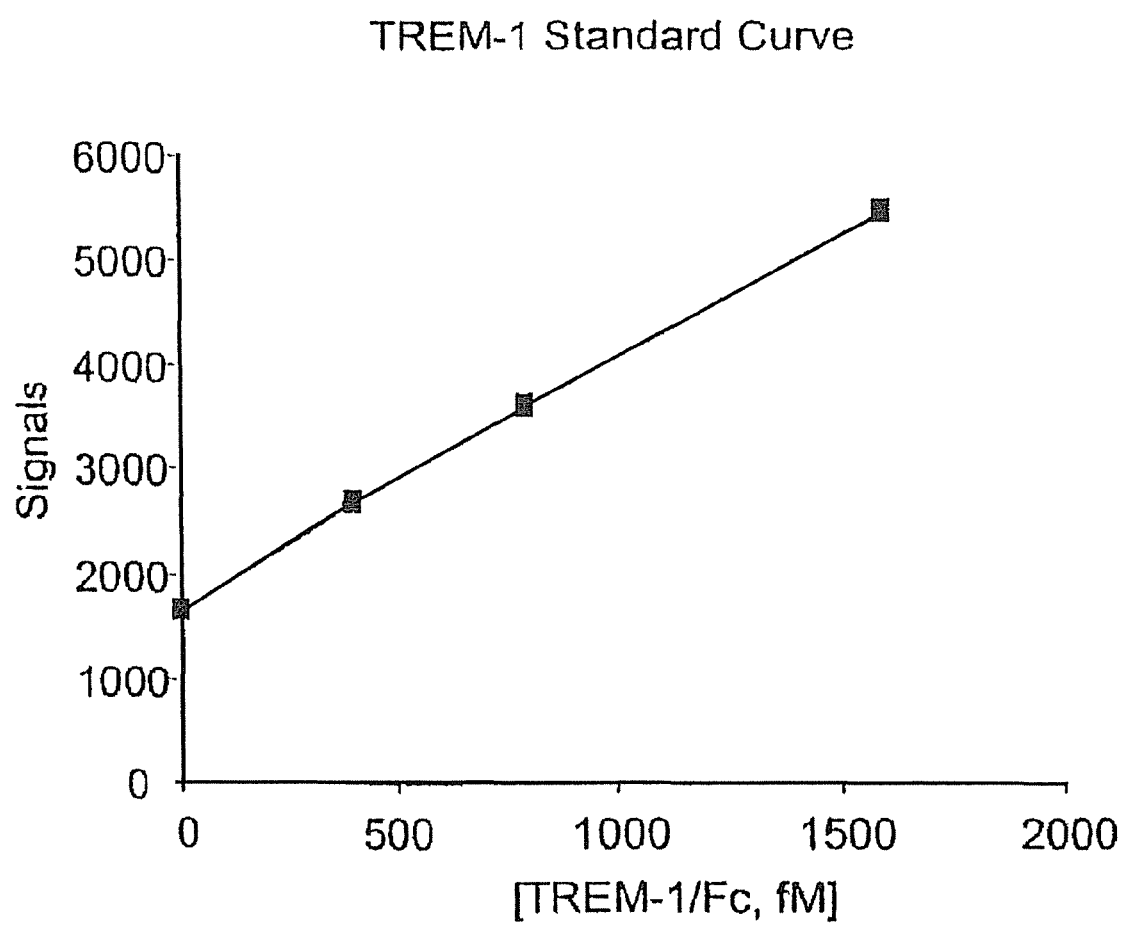
FIG. 13: Standard curve of TREM-1 measured in a sandwich molecule immunoassay developed for the single particle analyzer system. The linear range of the assay is 100-1500 fM.
Figure 15:
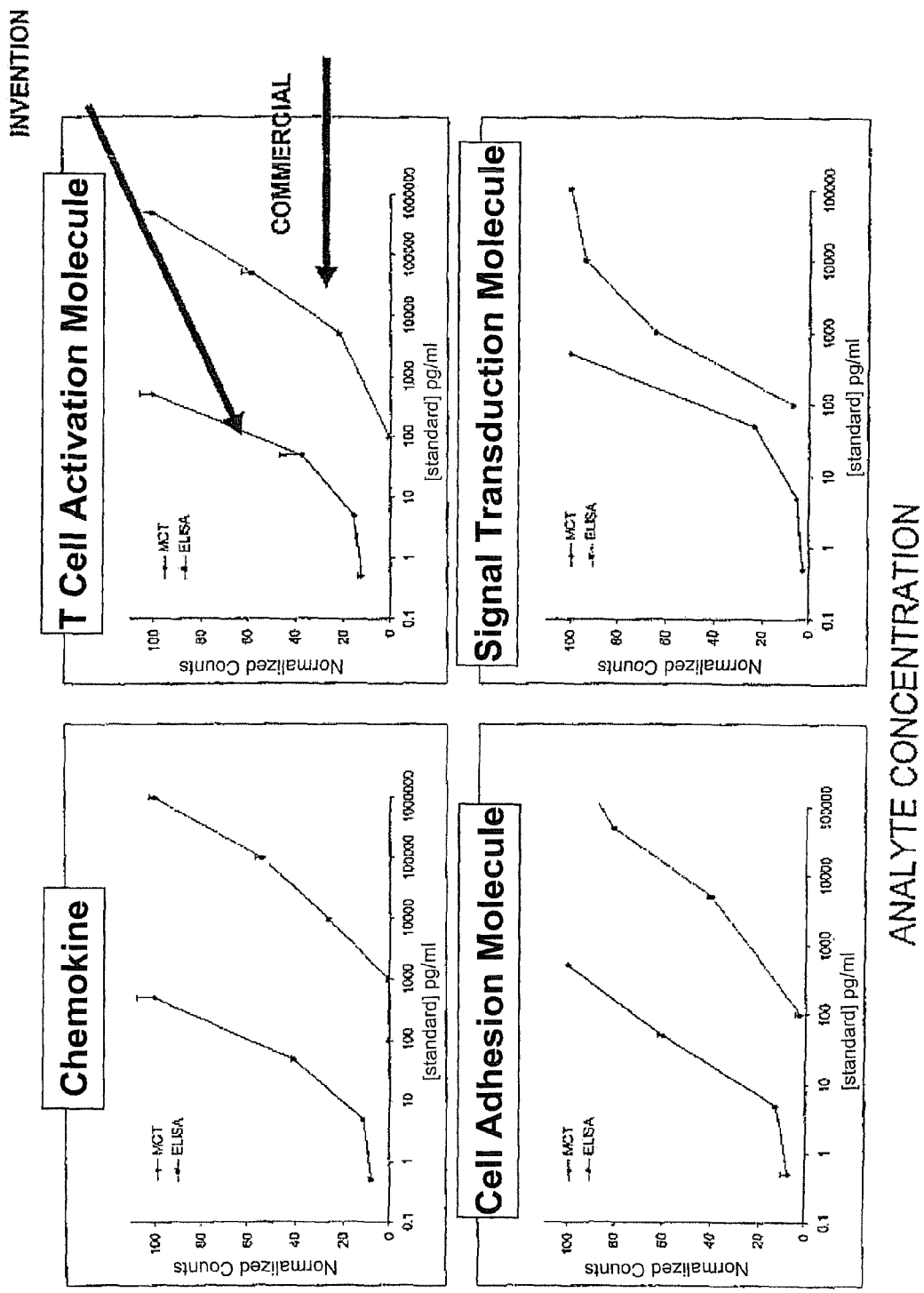
FIG. 15. Comparison of assays of the invention with conventional assays.

FIG. 13 shows a standard curve of TREM-1 generated using the assay. The assay was linear in the measured range of 100-1500 femtomolar. An ELISA assay from R&D Systems has recently been introduced. The standard curve reported for their ELISA assay is between 60-4000 pg/ml. This Example suggests we can routinely measure 100 fM (4.7 pg/ml) in a standard curve, allowing for about 10× more sensitive measurements. In addition, standard curves for chemokines, T cell activation molecules, cell adhesion molecules and signal transduction molecules have been generated (FIG. 15). The results show that the detection by the detection of analyte using the single particle analyzer is consistently between 10 and 100 fold more sensitive than detection using ELISA assays.

Example 10

Sandwich Assays for Biomarkers: IL-6 and IL-8 Levels in Serum

The assay: This protocol describes a sandwich immunoassay for the quantification of low levels of IL-6 in serum using the single particle analyzer system of the invention. A standard curve was generated by dilution of a concentrated standard into a buffered protein solution. Ten microliters (µl) of assay buffer and 10 µl of sample or standard were added to each well of a 384-well plate coated with an antibody specific for IL-6 and incubated for two hours. The plate was washed, and 20 µl of labeled detection antibody specific for IL-6 was added to each well. After one hour of incubation the plate was washed to remove unbound detection antibody. Bound detection antibody was eluted and measured in the single particle analyzer instrument.

Materials: the following materials were used in the procedure described below: coated 384 well plate; assay buffer; standard diluent; 100 ng/ml stock solution of IL-6 standard; detection antibody for IL-6 (R&D Systems) labeled with AlexaFluor 647 dye; TritonX-100 Wash buffer (10 mM Borate, 150 mM NaCl, 0.1% TritonX-100, pH 8.3); Elution buffer (4 M urea with 0.02% Triton X-100 and 0.001% BSA); Microplate shaker, set at "7"; Microplate washer; Plate centrifuge; Axyseal sealing film, Axygen product 321-31-051; and Nunc pierceable sealing tape, Nunc product 235306.

Procedure: IL-6 standard and sample preparation and analysis

A standard curve for IL-6 was prepared as follows: 100 ng/ml stock solution were thawed, and the stock solution was diluted 1:1000 to 100 pg/ml in standard diluent by doing six serial, 3 fold dilutions to obtain a range of concentration having the lowest standard concentration of 0.14 pg/ml. 10 µl assay buffer and 10 µl standard or sample were added to each well per well of the coated 384 well plate. The plate was sealed with Axyseal sealing film, and centrifuged for one minute at 3000 RPM. The assay plate was incubated for 2 hours at 25° C. with shaking; washed five times; and centrifuged while inverted on a paper towel for one minute at 3000 RPM. 20 µl detection antibody reagent was added to each well; the plate was sealed with Axyseal sealing film, and centrifuged for one minute at 3000 RPM. The assay plate was incubated for one hour at 25° C. with shaking, washed five times, and centrifuged while inverted on a paper towel for one minute at 3000 RPM. 30 µl elution buffer was added to each well; the plate was sealed with Nunc pierceable sealing tape, and a tight seal was secured using with roller. The assay plate was centrifuged for one minute at 3000 RPM, and incubated for ½ hour at 25° C. with shaking. Analysis of the assay was performed immediately. Alternatively, the plate was stored for up to 48 hours at 4° C. prior to analysis.

Samples of serum from EDTA treated whole blood of 32 blood bank donors were analyzed for IL-6.

Results: Data for a typical IL-6 standard curve measured in quadruplicate using the assay protocol is shown in Table 18.

TABLE 18

Standard Curve for IL-6

| Concentration (pg/ml) | Average Signal | Standard deviation | CV |
|---|---|---|---|
| 370 | 11035 | 206 | 2% |
| 125 | 9983 | 207 | 2% |
| 41 | 8522 | 95 | 1% |
| 14 | 5023 | 108 | 2% |
| 4.5 | 2577 | 124 | 5% |
| 1.7 | 1178 | 114 | 10% |
| 0.5 | 577 | 36 | 6% |
| 0 | 106 | 15 | 14% |

Figure 14:
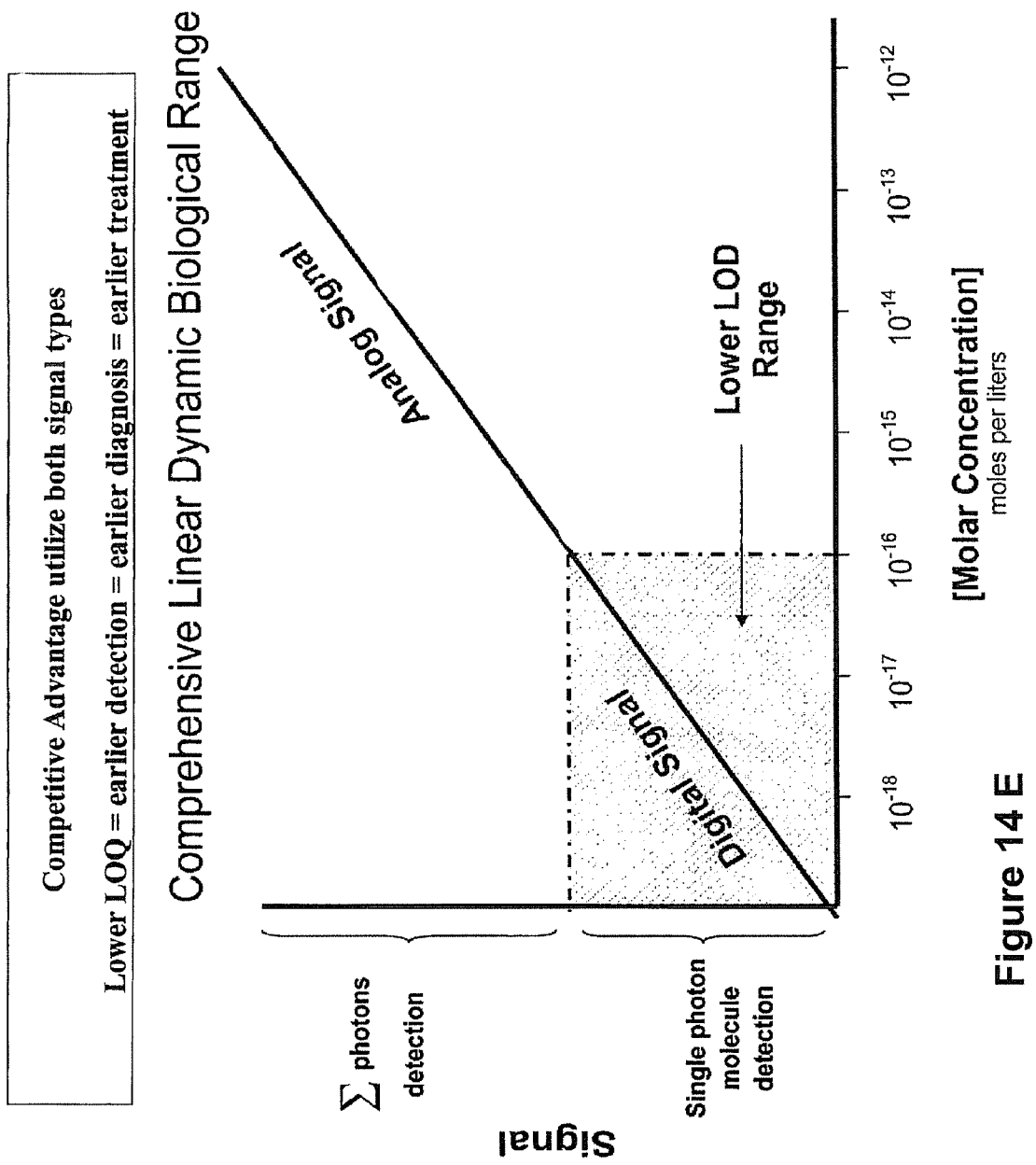
FIG. 14 A-F. Detection of IL-6 and IL-8. A-B) Standard curve for IL-6. A) IL-6 standards, diluted according to a commercially available kit (R & D Systems, Minneapolis, Minn.) gave a linear response between 0.1 and 10 pg/ml. B) IL-6 standard curve below 1 pg/ml. C) Distribution of IL-6 and IL-8 identified in blood bank donor EDTA specimens. D) Range of detection at low concentrations of any analyte can be extended to higher concentrations by switching the detection of the analyzer from counting molecules (digital signal) to detecting the sum of photons (analog signal) that are generated at the higher concentrations of analyte. The single particle analyzer has an expanded linear dynamic range of 6 logs. E) Six-log range of detection based on switching from digital to analog detection. F) Non-linearized standard curve showing range of low concentrations of IL-6 (0.1 fg/ml-10 fg/ml) determined by counting photons emitted by individual particles (digital signal), and higher range of concentrations of IL-6 (10 fg/ml-1 pg/ml).
Figure 14:
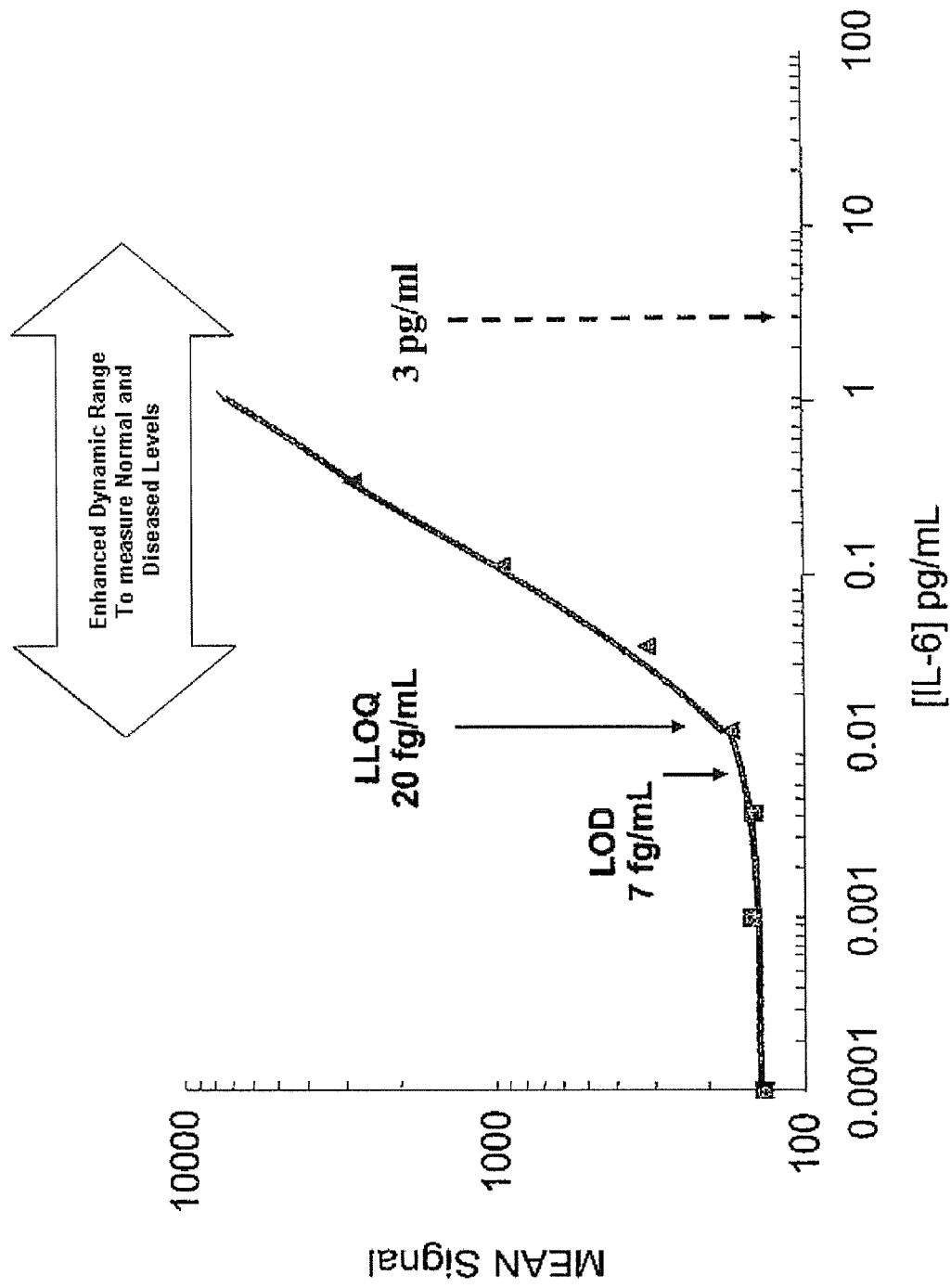

Linearized standard curves for higher and low range concentrations of IL-6 are shown in FIGS. 15 A-B, respectively. The assay allowed for detection of IL-6 at less than 0.5 pg/ml (FIGS. 14 A-B). The limit of detection (LoD) was calculated to be 0.06 pg/ml. The limit of detection of the assay (LoD) was determined by adding two standard deviations to the mean signal of the zero standard replicates and calculating the corresponding IL-6 concentration from the standard curve. This level of sensitivity is excellent for detection of even normal levels of IL-6 which range between 0.5 and 10 pg/ml.

Assays to detect IL-6 and IL-8 in serum of blood samples from blood bank donors were performed, and the results of the analysis are shown in FIGS. 14 C and D. IL-6 was quantified in 100% of the samples (32/32). The average concentration of IL-6 was 2.3 pg/ml, and the range of concentration was 0.2 to >26 pg/ml (FIG. 14 C). The same samples were also assayed for IL-8 essentially using the procedure described for IL-6. IL-8 standards and IL-8 specific antibodies were used. A standard curve for IL-8 was established (not shown) and used to determine the concentration of IL-8 in the samples (FIG. 14D). IL-8 was quantified in 100% (32/32) samples. The average concentration for IL-8 was 7.3 pg/ml, and the range of concentration was 1.2 to >26 pg/ml.

Measurements of IL-6 or any particle of interest can be measured at low and higher concentrations (FIGS. 14 A and B) by switching the detection of the analyzer from counting molecules (digital signal) to detecting the sum of photons (analog signal) that are generated at the higher concentrations of analyte. This is shown in a general way in FIG. 14E. The single particle analyzer has an expanded linear dynamic range of 6 logs. The ability to increase the dynamic range for detecting the concentration of a particle in a sample allows for the determination of the concentration of a particle for normal (lower concentration range) and disease levels (higher concentration range). The range of detection for normal and disease levels of IL-6 is shown in FIG. 15F.

What is claimed is:

1. A system for detecting a single protein molecule in a sample, the system comprising an analyzer and at least one label comprising a fluorescent moiety and a binding partner for said protein molecule, and wherein said analyzer comprises:

a) an electromagnetic radiation source for stimulating said fluorescent moiety, b) a capillary flow cell for passing said label;
c) a source of motive force of moving said label in said capillary flow cell;
d) an interrogation space within said capillary flow cell for receiving electromagnetic radiation emitted from said electromagnetic radiation source, wherein the interrogation space is defined by the focused spot of a beam from the electromagnetic radiation source wherein the spot has a diameter of 1-10 microns; and
e) an electromagnetic radiation detector operably connected to said interrogation space for measuring an electromagnetic characteristic of said stimulated fluorescent moiety;
wherein said fluorescent moiety emits at least about 200 photons when stimulated at the excitation wavelength of the moiety and the total energy directed at the interrogation space by the electromagnetic radiation source is no more than about 15 micro Joules.

2. The system of claim 1, wherein the electromagnetic radiation source has a power output greater than 0.5 mW.

3. The system of claim 1, wherein the analyzer comprises not more than one interrogation space.

4. The system of claim 1, wherein the fluorescent moiety comprises a fluorescent molecule.

5. The system of claim 4, wherein the fluorescent molecule comprises a dye molecule.

6. The system of claim 5, wherein the dye molecule comprises at least one substituted indolium ring system in which the substituent on the 3-carbon of the indolium ring contains a chemically reactive group or a conjugated group.

7. The system of claim 1, wherein the fluorescent moiety is a quantum dot.

8. The system of claim 1, wherein the fluorescent moiety comprises a dye selected from the group consisting of AlexaFluor 488, AlexaFluor 532, AlexaFluor 647, AlexaFluor 680 or AlexaFluor 700.

9. The system of claim 1, wherein the electromagnetic radiation source is a continuous wave electromagnetic radiation source.

10. The system of claim 9, wherein the continuous wave electromagnetic radiation source is a light-emitting diode or a continuous wave laser.

11. The system of claim 1, wherein the electromagnetic radiation source is a laser having a power output of at least about 3, 5, 10, or 20 mW.

12. The system of claim 1, wherein the source of motive force comprises a pressure source.

13. The system of claim 12, wherein the pressure source comprises a pump, a vacuum source, a centrifuge, or a combination thereof.

14. The system of claim 1, wherein a limit of detection of the protein molecule in the sample is less than about 100 femtomolar.

15. The system of claim 1, wherein the limit of detection of the protein molecule in the sample is less than about 10 femtomolar.

16. The system of claim 1, wherein the interrogation space has a volume between about 0.05 pL and about 50 pL.

17. The system of claim 1, wherein the interrogation space has a volume between about 0.1 pL and about 25 pL.

18. The system of claim 1, wherein the volume of the interrogation space is adjustable.

19. The system of claim 1, wherein the electromagnetic radiation detector is an avalanche photodiode.

20. The system of claim 1, further comprising a data analysis system that analyzes the electromagnetic characteristic and reports the results of the analysis.

21. The system of claim 1, wherein the analyzer is capable of detecting a difference of less than 20% in concentration of an analyte between a first sample and a second sample, when the first sample and the second sample are introduced into the analyzer, the volume of the first sample and the second sample introduced into the analyzer is less than 5 µl, and wherein the analyte is present at a concentration of less than 50 femtomolar in the first and second samples.

22. A system for detecting a single protein molecule in a sample, comprising: a label comprising a fluorescent moiety and a binding partner for the protein molecule and an analyzer comprising:
(a) an electromagnetic radiation source for emitting electromagnetic radiation, wherein said fluorescent moiety emits at least about 200 photons when stimulated at the excitation wavelength of the moiety and the total energy directed at the interrogation space by the electromagnetic radiation source is no more than about 15 micro Joules;
(b) a first interrogation space positioned to receive electromagnetic radiation emitted from the electromagnetic radiation source wherein the interrogation space is defined by the focused spot of a beam from the electromagnetic radiation source wherein the spot has a diameter of 1-10 microns;
(c) a second interrogation space positioned to receive electromagnetic radiation emitted from the electromagnetic radiation source, wherein the second interrogation space is in fluid communication with the first interrogation space and wherein a motive source provides a motive force between the first interrogation space and the second interrogation space such that a particle comprising at least the label can be moved between the first interrogation space and the second interrogation space;
(d) a first electromagnetic radiation detector operably connected to the first interrogation space to measure a first electromagnetic characteristic of the particle in the first interrogation space;
(e) a second electromagnetic radiation detector operably connected to the second interrogation space to measure at least one of a second electromagnetic characteristic of the particle in the second interrogation space and the first electromagnetic characteristic of the particle.

23. A system for detecting a single protein molecule in a sample, comprising:
(a) a sampling system providing a fluid communication between a sample container and a first interrogation space, wherein the interrogation space is defined by the focused spot of a beam from an electromagnetic radiation source wherein the spot has a diameter of 1-10 microns and the total energy directed at the interrogation space by an electromagnetic radiation source is no more than about 15 micro Joules;
(b) a single particle analyzer comprising the first interrogation space and a second interrogation space wherein the second interrogation space is in fluid communication with the first interrogation space and wherein a pressure source provides a motive force between the first interrogation space and the second interrogation space such that a particle can be moved between the first interrogation space and the second interrogation space;
(c) a detector operably connected to at least one of the first or the second interrogation spaces, wherein the detector is located for detecting a detectable characteristic of the particle, if present, and wherein the interrogation spaces are defined by the field of view of the detector;

(d) a sample recovery system comprising a means for moving the sample whereby the sample can move from the sample container to the interrogation spaces and back to the sample container without contacting other components of the analyzer and with no substantial contact with clean buffer within the analyzer; and
(e) a data analyzer that receives input from the detector, analyzes the presence or absence of the particle, and reports a result based on the presence or absence.

\* \* \* \* \*